United States Patent
Pan

(10) Patent No.: US 12,343,408 B2
(45) Date of Patent: Jul. 1, 2025

(54) AAV-MEDIATED SUBCELLULAR TARGETING OF HETEROLOGOUS RHODOPSINS IN RETINAL GANGLION CELLS

(71) Applicant: Wayne State University, Detroit, MI (US)

(72) Inventor: Zhuo-Hua Pan, Troy, MI (US)

(73) Assignee: Wayne State University, Detroit, MI (US)

( * ) Notice: Subject to any disclaimer, the term of this patent is extended or adjusted under 35 U.S.C. 154(b) by 914 days.

(21) Appl. No.: 17/195,288

(22) Filed: Mar. 8, 2021

(65) Prior Publication Data

US 2022/0040326 A1 Feb. 10, 2022

Related U.S. Application Data

(63) Continuation of application No. 15/978,290, filed on May 14, 2018, now abandoned, which is a continuation of application No. 15/236,152, filed on Aug. 12, 2016, now Pat. No. 9,968,689, which is a continuation of application No. 13/696,252, filed as application No. PCT/US2011/035266 on May 4, 2011, now Pat. No. 9,453,241.

(60) Provisional application No. 61/331,125, filed on May 4, 2010.

(51) Int. Cl.
| | |
|---|---|
| A61K 48/00 | (2006.01) |
| A61K 38/00 | (2006.01) |
| A61P 27/02 | (2006.01) |
| C07K 14/47 | (2006.01) |
| C07K 14/705 | (2006.01) |
| C12N 15/861 | (2006.01) |

(52) U.S. Cl.
CPC ........ *A61K 48/005* (2013.01); *C07K 14/4702* (2013.01); *C07K 14/705* (2013.01); *C12N 15/8616* (2013.01); *A61K 38/00* (2013.01); *A61P 27/02* (2018.01); *C07K 2319/01* (2013.01); *C12N 2750/14143* (2013.01)

(58) Field of Classification Search
CPC .............. A61K 48/005; C07K 14/4702; C07K 14/705; C07K 2319/01; C12N 15/8616; C12N 2750/14143; C12N 15/861
USPC ....... 435/320.1, 455, 456; 514/44; 424/93.2, 424/93.21
See application file for complete search history.

(56) References Cited

U.S. PATENT DOCUMENTS

| | | |
|---|---|---|
| 4,498,919 A | 2/1985 | Mann |
| 4,554,101 A | 11/1985 | Hopp |
| 5,827,702 A | 10/1998 | Cuthbertson |
| 6,610,287 B1 | 8/2003 | Breakefield |
| 7,144,733 B2 | 12/2006 | Miesenbock |
| 7,186,699 B2 | 3/2007 | Harding |
| 7,427,138 B2 | 9/2008 | Ellenbogen |
| 7,824,869 B2 | 11/2010 | Hegemann |
| 8,470,790 B2 | 6/2013 | Pan |
| 9,453,241 B2 * | 9/2016 | Pan ..................... A61K 48/005 |
| 9,968,689 B2 | 5/2018 | Pan |
| 2004/0022766 A1 | 2/2004 | Acland |
| 2005/0202398 A1 | 9/2005 | Hegemann |
| 2005/0208022 A1 | 9/2005 | Masland |
| 2010/0015095 A1 | 1/2010 | Pan |
| 2014/0121265 A1 | 5/2014 | Pan |
| 2015/0044181 A1 | 2/2015 | Pan |

FOREIGN PATENT DOCUMENTS

| | | |
|---|---|---|
| WO | 1998048027 A2 | 10/1998 |
| WO | 0015822 A1 | 3/2000 |
| WO | 0183692 A2 | 11/2001 |
| WO | 2005044096 A2 | 5/2005 |
| WO | 2007024391 A2 | 3/2007 |
| WO | WO 2007131180 A2 * | 11/2007 |
| WO | 2011140279 A1 | 11/2011 |
| WO | 2012032103 A1 | 3/2012 |
| WO | 2013134295 A1 | 9/2013 |

OTHER PUBLICATIONS

Santos, AH et al., "Preservation of the Inner Retina in Retinitis Pigmentosa," Arch. Ophthalmol. vol. 115: 511-515 (1997).
Sineshchekov et al., "Two rhodopsins mediate phototaxis to low- and high-intensity light in Chlamydomonas reinhardtii," Proceedings of the National Academy of Sciences of the United States of America, vol. 99: 8689-8694 (2002).

(Continued)

*Primary Examiner* — Christopher M Babic
*Assistant Examiner* — Jennifer S Spence
(74) *Attorney, Agent, or Firm* — KDW Firm PLLC

(57) ABSTRACT

Microbial type rhodopsins, such as the light-gated cation-selective membrane channel, channelrhodopsin-2 (Chop2/ChR2) or the ion pump halorhodopsin (HaloR) are expressed in retinal ganglion cells upon transduction using recombinant AAV vectors. Selective targeting of these transgenes for expression in discrete subcellular regions or sites is achieved by including a sorting motif in the vector that can target either the central area or surround (off-center) area of these cells. Nucleic acid molecules comprising nucleotide sequences encoding such rhodopsins and sorting motifs and their use in methods of differential expression of the transgene are disclosed. These compositions and methods provide significant improvements for restoring visual perception and various aspects of vision, particular in patients with retinal disease.

18 Claims, 32 Drawing Sheets

Specification includes a Sequence Listing.

(56) References Cited

OTHER PUBLICATIONS

Sung et al., "Rhodopsin mutations in autosomal dominant retinitis pigmentosa," Proceedings of the National Academy of Sciences of the United States of America, vol. 88: 6481-6485 (1991).
Takahashi, M. et al., "Rescue from Photoreceptor Degeneration in the rd Mouse by Human Immunodeficiency Virus Vector-Mediated Gene Transfer," J Virol. vol. 73, 1999, pp. 7812-7816.
Tomita et al., "Channelrhodopsins provide a breakthrough insight into strategies for curing blindness," Journal of Genetics, 88:409-415 (2009).
Thyagarajan et al., "Visual Function in Mice with Photoreceptor Degeneration and Transgenic Expression of Channelrhodopsin 2 in Ganglion Cells," J Neurosci 2010; 30: 8745-5.
Tomomura et al., "Purification of Purkinje cells by fluorescence-activated cell sorting from transgenic mice that express green fluorescent protein," European Journal of Neuroscience, vol. 14: 57-63 (2001).
Ueda et al., "The mGluR6 5 upstream transgene sequence directs a cell-specific and developmentally regulated expression in retinal cord and ON-type cone bipolar cells," Journal of Neuroscience, vol. 17: 3014-3023 (1997).
Ullrich et al., "Degradation of Channelopsin-2 in the Absence of Retinal and Degradation Resistance in Certain Mutants", Biological Chemistry, vol. 394, No. 2, Feb. 1, 2013, pp. 271-280.
Veraart et al., "Vision Rehabilitation in the case of Blindness," Expert Rev. Medical Devices 1 (1):139-153 (2004)—Abstract.
Walther et al., "Viral Vectors for Gene Transfer a Review of Their Use in the Treatment of Human Diseases," Drugs, vol. 60: 249-271 (2000).
Wassle, "Parrallel Processing in the Mammalian Retina," Nature Reviews Neuroscience, vol. 5: 747-757 (2004).
Xue et al., "Multiple-color optical activation, silencing, and desynchronization of neural activity, with single-spike temporal resolution," PLOS ONE 2007 Lnkdpubmed: 17375185, vol. 2, No. 3, 2007, p. e299.
Zemelman et al., "Selective Photostimulation of Genetically Charged Neurons," Neuron, vol. 33: 15-22 (2002).
Zhang et al., "Multimodal fast optical interrogation of neural circuitry," Nature, vol. 446: 633-639 (2007).
Zrenner et al., "Will Retinal Implants Restore Vision" Science, vol. 295(1): 022-025 (2002).
International Preliminary Report on Patentability and Written Opinion of the International Searching Authority for Application No. PCT/US2007/068263, dated Nov. 4, 2008, 6 pages.
International Search Report issued by the International Searching Authority for Application No. PCT/US2007/068263, dated May 15, 2008, 4 pages.
International Preliminary Report on Patentability and Written Opinion of the International Searching Authority for Application No. PCT/US2011/035266, dated Nov. 6, 2012, 5 pages.
International Search Report of the International Searching Authority for Application No. PCT/US2011/035266, dated Jul. 27, 2011, 4 pages.
Communication Pursuant to Article 94(3) EPC issued by the European Patent Office for Application No. EP07797340.2, dated Sep. 25, 2014, 5 pages.
Office Action issued by the United States Patent and Trademark Office for U.S. Appl. No. 12/299,574, dated Aug. 28, 2012, 15 pages.
Office Action issued by the United States Patent and Trademark Office for U.S. Appl. No. 12/299,574, dated Jan. 12, 2012, 10 pages.
Office Action issued by the United States Patent and Trademark Office for U.S. Appl. No. 13/899,198, dated Jul. 21, 2014, 20 pages.
Acland et al., "Gene Therapy Restores Vision in Canine Model of Childhood Blindness," Nature Genetics, vol. 28:92-95 (2001).
Ali et al., "Restoration of Photoreceptor Ultrastructure and Function in Retinal Degeneration Slow Mice by Gene Therapy," Nature Genetics, vol. 25: 306-310 (2000).
Banghart et al., "Light-activated ion channels for remote control of neuronal firing," Nature Neuroscience, vol. 7, Issue 12: 1381-1386 (2004).
Baylor, "How Photons Start Vision," Proceedings of the National Academy of Sciences of the United States of America, vol. 93: 560-565 (1996).
Bennett et al., "Stable transgene expression in rod photoreceptors after recombinant adeno-associated virus-mediated gene transfer to monkey retina," Proceedings of National Academy of Sciences of the United States of America, vol. 96; 9920-9925 (1999).
Bennett et al., "Adenovirus-mediated delivery of rhodopsin-promoted bcl-2 results in a delay in photoreceptor cell death in the rd/rd mouse," Gene Therapy, vol. 5: 1156-1164 (1998).
Bennet et al., "Photoreceptor cell rescue in retinal degeneration (rd) mice by in vivo gene therapy," Nature Medicine, vol. 2: 649-654 (1996)—Abstract.
Berson, "Phototransduction in Ganglion-Cell Photoreceptors," European Journal of Physiology, vol. 454: 849-855 (2007).
Berndt et al., "High-efficiency channelrhodopsins for fast neuronal stimulation at low light levels," Proceedings of the National Academy of Sciences of the United States of America, vol. 108(18): 7595-7600 (2011).
Bi et al., "Ectopic expression of a microbial-type rhodopsin restores visual responses in mice with photoreceptor degeneration," Neuron, vol. 50: 23-33 (2006).
Borras, "Recent Developments in Ocular Gene Therapy," Experimental Eye Research, vol. 76: 643-652 (2003)—Abstract.
Casini et al., "Developmental Expression of Neurokinin-1 and Neurokinin-3 Receptors in the Rat Retina," The Journal of Comparative Neurology, vol. 421: 275-287 (2000)—Abstract.
Chang et al., "Retinal degeneration mutants in the mouse," Vision Research, vol. 42: 517-525 (2002).
Flannery et al., "Looking Within for Vision," Neuron, vol. 50(1): 1-3 (2006).
Flannery et al., "Efficient photoreceptor-targeted gene expression in vivo by recombinant adeno-associated virus," Proceedings of the National Academy of Sciences of the United States of America, vol. 94: 6916-6921 (1997).
Greenberg et al., "In vivo Transgene Expression in ON-Type Retinal Ganglion Cells: Applications to Retinal Disease," ARVO (2007)—Abstract.
Hankins et al., "Melanopsin: An Exciting Photopigment," Trends Neuroscience, vol. 31(1): 27-36 (2007)—Abstract.
Hauswirth et al., "Ocular Gene Therapy: Quo Vadis?," Investigative Ophthalmology & Visual Science, vol. 41(1): 2821-2826 (2000).
Hauswirth, "Consortium Project to Treat RPE65 Deficiency in Humans," Retina, vol. 25: 60 (2005).
Haverkamp et al., "Immunocytochemical Description of Five Bipolar Cell Types of the Mouse Retina," Journal of Comparative Neurology, vol. 455: 463-476 (2003).
Hossain et al., "Artificial Means for Restoring Vision," British Medical Journal, vol. 330: 30-33 (2005).
Humphries et al., "On the molecular genetics of retinitis pigmentosa," Science, vol. 256: 804-808 (1992).
Ishizuka et al., "Kinetic Evaluation of Photosensitivity in Genetically Engineered Neurons Expressing Green Algae Light-Gated Channels," Neuroscience Research, vol. 54: 85-94 (2005).
Jacobson, S., Protocol #0410-677, National Institutes of Health Recombinant DNA Advisory Committee (RAC), 47 pages, (2005).
Kay et al., "Viral Vectors for Gene Therapy: The Art of Turning Infectious Agents into Vehicles of Therapeutics," Nature Medicine, vol. 7: 33-40 (2001)—Abstract.
Kleinlogel et al., "Ultra light-Sensitive and Fast Neuronal Activation with the Ca2+—Permeable Channelrhodopsin CatCh," Nature Neuroscience, vol. 14(4): 513-518 (2011).
Kumar-Singh et al,. "Encapsidated adenovirus mini-chromosome-mediated delivery of genes to the retina: application to the rescue of photoreceptor degeneration," Hum. Mol. Genet., vol. 7: 1893-1900 (1998).
Lanyi, JK., "Halorhodopsin, a Light-Driven Electrogenic Chloride-Transport System," Physiol Rev. vol. 70, No. 2, 1990, pp. 319-330.
Lanyi, JK, "Bacteriorhodopsin ." Annu Rev Physiol. vol. 66, 2004, pp. 665-688—Abstract.

(56) References Cited

OTHER PUBLICATIONS

Lau et al., "Retinal Degeneration Is Slowed in Transgenic Rats by AAV-Mediated Delivery of FGF-2," Invest. Ophthalmol. Vis. Sci. vol. 41 , 2000, pp. 3622-3633.

Lavail et al., "Multiple growth factors, cytokines, and neurotrophins rescue photoreceptors from the damaging effects of constant light," Proceedings of the National Academy of Sciences of the United States of America, vol. 89: 11249-11253 (1992).

Lavail, MM et al. , "Ribozyme rescue of photoreceptor cells in P23H transgenic rats: Long-term survival and late-stage therapy," Proc Natl Acad Sci USA vol. 97, 2000, pp. 11488-11493.

Lewin, AS et al., "Ribozyme Rescue of Photoreceptor Cells in a Transgenic Rat Model of Autosomal Dominant Retinitis Pigmentosa," Nat. Med. vol. 4, 1998, pp. 967-971.

Lin et al., "Restoration of Visual Function in Retinal Degeneration Mice by Ectopic Expression of Melanopsin," Proceedings of the National Academy of Sciences of the United States of America, vol. 105; 16009-16014 (2008).

McFarland et al., "Gene Therapy for Proliferative Ocular Diseases." Exp. Opin. Bioi. Ther.4.7(2004) :1 053-1058—Abstract.

Medeiros et al. "Preservation of Ganglion Cell Layer Neurons in Age-Related MacularDegeneration ." Invest. Ophthal. Vis. Sci. 42.3(2001 ) :795-803.

Melyan et al., "Addition of human melanopsin renders mammalian cells photoresponsive," Nature, vol. 433: 741-745 (2005).

Milam, AH et al., "Histopathology of the Human Retina in RetinitisPigmentosa," Prog. Retin. Eye Res. vol. 17, 1998, pp. 175-205.

Nagel et al., "Channelrhodopsin-1: A light-Gated Proton Channel in Green Algae," Science, vol. 296: 2395-2398 (2002).

Nagel et al., "Channelrhodopsin-2, a Directly Light-Gated Cation-Selective Membrane Channel," Proceedings of the National Academy of Sciences of the United States of America, vol. 100(24): 13940-13945 (2003).

Nakajima et al., "Molecular Characterization of a Novel Retinal Metabotropic Glutamate Receptor mGluR6 with a High Agonist Selectivity for L-2-Amino-4-phosphonobutyrate," Journal of Biological Chemistry, vol. 268: 11868-11873 (1993).

Oesterhelt et al., "Functions of a New Photoreceptor Membrane," Proceedings of the National Academy of Sciences of the United States of America, vol. 70: 2853-2857 (1973).

Oesterhelt, "The structure and mechanism of the family of retinal proteins from halophilic archaea," Current Opinion in Structural Biology, vol. 8: 489-500 (1998).

Olshevskaya, EV et al. , "The Y99C Mutation in Guanylyl Cyclase-Activating Protein 1 Increases Intracellular Ca2 and Causes Photoreceptor Degeneration in Transgenic Mice," J. Neurosci. vol. 24, 2004, pp. 6078-6085.

Pan et al., "Functional expression of a directly light-gated membrane channel in mammalian retinal neurons: A potential strategy for restoring light sensitivity to the retina after photoreceptor degeneration" Investigative Ophthalmology & Visual Science 46:E—Abstract 4631 (2005)—Abstract.

Panda et al., "Illumination of the Melanopsin Signaling Pathway," Science, vol. 307: 600-604 (2005).

Prigge, M. et al., "Color-Tuned Channelrhodopsins for Multiwavelength Optogenetics", Journal of Biological Chemistry, vol. 287, No. 38, 27, Jul. 2012, pp. 31804-31812.

Qiu et al., "Induction of photosensitivity by heterologous expression of melanopsin," Nature, vol. 433: 745-749 (2005).

Rein , Martin L. et al., "The Optogenetic (r)evolution", Molecular Genetics and Genomics, vol. 287, No. 2, Dec. 20, 2011 , pp. 95-109.

Reutsky et al. "Patterned Optical Activation of Channelrhodopsin II Expressing RetinalGanglion Cells." Proc. 3rd Int. IEEE EMBS Cont. Neural Engin. (2007) :50-52.

* cited by examiner

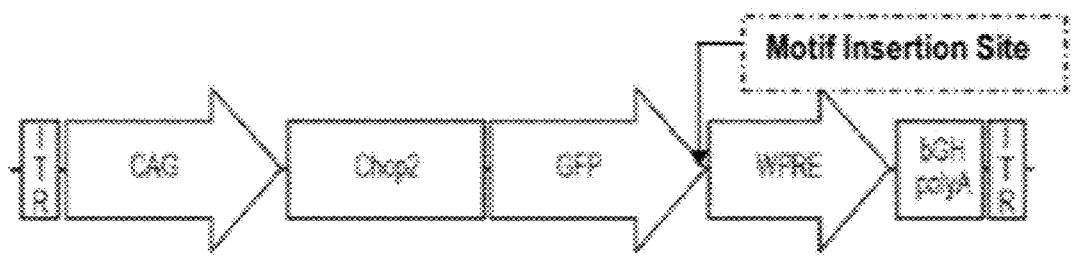

←start AAV2 ITR
cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac tagggggttcc tgcggccgca cgcgtgatat CCTAGTTATT AATAGTAATC
　　　　　　end AAV2 ITR→↑　　　　　　　　　　　　　　　↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGGTG TCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA

```
                                                      end CAG promoter/enhancer → ↓
CAGGGCCGGG TTCGGCTTCT GGCGTGTGAC CGGCGGCTCT AGCAGCCTCT GCTAaccatg
ttcatgcctt cttcttttc ctacagctcc tggcaacgt gctggtatt gtgctgtctc
                                                              ↓ ← start ChR2
atcattttgg caaagaatta agcttgagct cgcgatccgc agcc ATG GAT TAT GGA
GGC GCC CTG AGT GCC CTT GGG CGC GAG CTG CTA TTT GTA ACG AAC CCA
GTA GTC GTC AAT GGC TCT GTA CTT GTG CCT GAG GAC CAG TGT TAC TGC
GCG GGC TGG ATT GAG TCG CGT GGC ACA AAC GGT GCC CAA ACG GCG TCG
AAC GTG CTG CAA TGG CTT GCT GCT GGC TTC TCC ATC CTA CTG CTT ATG
TTT TAC GCC TAC CAA ACA TGG AAG TCA ACC TGC GGC TGG GAG GAG ATC
TAT GTG TGC GCT ATC GAG ATG GTC AAG GTG ATT CTT GAG TTC TTC TTC
GAG TTT AAG AAC CCG TCC ATG CTG TAT CTA GCC ACA GGC CAC CGC GTC
CAG TGG TTC CGT TAC GCC GAG TGG CTT CTC ACC TGC CCG GTC ATT CTC
ATT CAC CTG TCA AAC CTG ACG GGC TTG TCC AAC GAC TAC AGC AGG CGC
ACT ATG GGT CTC CTT GTG TCT GAT ATT GGC ACA ATT GTG TGG GGC GCC
ACT TCC GCT ATG GCC ACC GGA TAC GTC AAG GTC ATC TTC TTC TGC CTG
GGT CTG TGT TAT GGT GCT AAC ACG TTC TTT CAC GCT GCC AAG GCC TAC
ATC GAG GGT TAC CAT ACC GTG CCC AAG GGC CGG TGT CGC CAG GTG GTG
ACT GGC ATG GCT TGG CTC TTC TTC GTA TCA TGG GGT ATG TTC CCC ATC
CTG TTC ATC CTC GGC CCC GAG GGC TTC GGC GTC CTG AGC GTG TAC GGC
TCC ACC GTC GGC CAC ACC ATC ATT GAC CTG ATG TCG AAG AAC TGC TGG
GGT CTC CTC GGC CAC TAC CTG CGC GTG CTG ATC CAC GAG CAT ATC CTC
ATC CAC GGC GAC ATT CGC AAG ACC ACC AAA TTG AAC ATT GGT GGC ACT
GAG ATT GAG GTC GAG ACG CTG GTG GAG GAC GAG GCC GAG GCT GGC GCG
GTC AAC AAG GGC ACC GGC AAG gaattcggag gcggaggtgg agctagc
                    end ChR2 → ↑
↓ ← Start Kv2.1 Motif
CAG TCT CAG CCC ATC CTG AAC ACT AAG GAG ATG GCC CCT CAG AGT AAA
GCC CCT GAG GAA CTG GAA ATG AGC TCC ATG CCA TCT CCA GTG GCT CCT
CTG CCA GCT AGG ACA GAG GGC GTG ATT GAC ATG AGA AGC ATG AGT AGT
ATC GAT AGC TTC ATT TCC TGC GCC ACC GAC TTC CCC GAA GCT ACA AGG
TTT taactcgagt ctagacgtgg taccGATAAT CAACCTCTGG ATTACAAAAT
  ↑ ← end Kv2.1 Motif              ↑ ← start WPRE
TTGTGAAAGA TTGACTGGTA TTCTTAACTA TGTTGCTCCT TTTACGCTAT GTGGATACGC
TGCTTTAATG CCTTTGTATC ATGCTATTGC TTCCCGTATG GCTTTCATT TCTCCTCCTT
GTATAAATCC TGGTTGCTGT CTCTTTATGA GGAGTTGTGG CCCGTTGTCA GGCAACGTGG
CGTGGTGTGC ACTGTGTTTG CTGACGCAAC CCCCACTGGT TGGGGCATTG CCACCACCTG
TCAGCTCCTT TCCGGGACTT TCGCTTTCCC CCTCCCTATT GCCACGGCGG AACTCATCG
CCGCCTGCCT TGCCCGCTGC TGGACAGGGG CTCGGCTGTT GGGCACTGAC AATTCCGTGG
TGTTGTCCGG AAGTGACAAT CCTTTCCATG GCTGCTCGCC TGTGTTGCCA CCTGGATTC
TGCGCGGGACG TCTTTTGTAT AGTCCCTTCG GGCCTCAAT CCAGCGGACC TTCCTTCCCG
CGGCCTGCTG CCGGCTCTGC GGCCTCTTCC GCGTCTTCGC CTTCGCCCTC AGACGAGTCG
GATCTCCCTT TGGGCCGCCT CCCCGCCTGA tgcggggatc tctagagtc gagagatctA
                              end WPRE → ↑                   start bGH-polyA → ↑
CGGGTGGCAT CCCTGTGACC CCTCCCCAGT GCCTCTCCTG GCCCTGGAAG TTGCCACTCC
AGTGCCCACC AGCCTTGTCC TAATAAAATT AAGTTGCATC ATTTTGTCTG ACTAGGTGTC
CTTCTATAAT ATTATGGGGT GGAGGGGGGT GGTATGGAGC AAGGGGCAAG TTGGGAAGAC
AACCTGTAGG GCCTGCGGGG TCTATTGGGA ACCAAGCTGG AGTGCAGTGG CACAATCTTG
GCTCACTGCA ATCTCCGCCT CCTATTGGTTCA AGCGATTCTC CTGCCTCAGC CTCCCGAGTG
GTTGGGATTC CAGGCATGCA TGACCAGGCT CAGCTAATTT TTGTTTTTTT GGTAGAGACG
GGGTTTCACC ATATTGGCCA GGCTGGTCTC CAACTCCTAA TCTCAGGTGA TCTACCCACC
TTGGCCTCCC AAATTGCTGG GATTACAGGC GTGAACCACT GCTCCCTTCC CTGTCCTTCt
                                                             end bGH-polyA → ↑
gattttgtag gtaaccacgt gcggaccgag cggccgcagg aaccccTAGT GATGGAGTTG
                                      ↑ ← start AAV2 ITR
GCCACTCCCT CTCTGCGCGC TCGCTCGCTC ACTGAGGCCG GGCGACCAAA GGTCGCCCGA
CGCCCGGGCT TTGCCCGGGC GGCCTCAGTG AGCGAGCGAG CGCGCAGCTG CCTGCAGG
                                                         end AAV2 ITR → ↑
```

5'-ITR—CAG—ChR2—GFP—[NLG1 Motif]—WPRE—bGHpolyA—ITR-3'

←start AAV2 ITR
*cctgcaggca gctgcgcgct cgctcgctca ctgaggccgc ccgggcaaag cccgggcgtc*
*gggcgacctt tggtcgcccg gcctcagtga gcgagcgagc gcgcagagag ggagtggcca*
*actccatcac tagggggttcc* tgcggccgca cgcgtgatat CCTAGTTATT AATAGTAATC
         end AAV2 ITR→↑                     ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGGTCG AGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGACGGC TGCCTTCGGG GGGGACGGGG
                                          end CAG pomoter/enhancer→↓
CAGGGCGGGG TTCGGCTTCT GGCGTGTGAC CGGCGGCTCT AGCAGCCTCT GCTAaccatg
ttcatgcctt cttcttttc ctacagctcc tgggcaacgt gctggttatt gtgctgtctc
                                                                     ↓←start ChR2
atcattttgg caaagaatta agcttgagct cgcgatccgc agcc *ATG GAT TAT GGA*
*GGC GCC CTG AGT GCC GTT GGG CGC GAG CTG CTA TTT GTA ACG AAC CCA*
*GTA GTC GTC AAT GGC TCT GTA CTT GTG CCT GAG GAC CAG TGT TAC TGC*
*GCG GGC TGG ATT GAG TCG CGT GGC ACA AAC GGT GCC CAA ACG GCG TCG*
*AAC GTG CTG CAA TGG CTT GCT GCT GGC TTC TCC ATC CTA CTG CTT ATG*
*TTT TAC GCC TAC CAA ACA TGG AAG TCA ACC TGC GGC TGG GAG GAG ATC*
*TAT GTG TGC GCT ATC GAG ATG GTC AAG GTG ATT CTT GAG TTC TTC TTC*
*GAG TTT AAG AAC CCG TCC ATG CTG TAT CTA GCC ACA GGC CAC CGC GTC*
*CAG TGG TTG CGT TAC GCC GAG TGG CTT CTC ACC TGC CCG GTC ATT CTC*
*ATT CAC CTG TCA AAC CTG ACG GGC TTG TCC AAC GAC TAC AGC AGG CGC*
*ACT ATG GGT CTG CTT GTG TCT GAT ATT GGC ACA ATT GTG TGG GGC GCC*
*ACT TCC GCT ATG GCC ACC GGA TAC GTC AAG GTC ATC TTC TTC TGC CTG*
*GGT CTG TGT TAT GGT GCT AAC ACG TTC TTC CAC GCT GCC AAG GCC TAC*
*ATC GAG GGT TAC CAT ACC GTG CCG AAG GGC CGG TGT CGC CAG GTG GTG*
*ACT GGC ATG GCT TGG CTC TTC TTC GTA TCA TGG GGT ATG TTC CCC ATC*
*CTG TTC ATC CTC GGC CCC GAG GGC TTC GGC GTC CTG AGC GTG TAC GGC*
*TCC ACC GTC GGC CAC ACC ATC ATT GAC CTG ATG TCG AAG AAC TGC TGG*
*GGT CTG CTC GGC CAC TAC CTG CGC GTG CTG ATC CAC GAG CAT ATC CTC*
*ATC CAC GGC GAC ATT CGC AAG ACC ACC AAA TTG AAC ATT GGT GGC ACT*
*GAG ATT GAG GTC GAG ACG CTG GTG GAG GAC GAG GCC GAG GCT GGC GCG*
*GTC AAC AAG GGC ACC GGC AAG* gaattcggag gcggaggtgg agctagc
                      end ChR2→↑
↓←start GFP
AAA GGA GAA GAA CTC TTC ACT GGA GTT GTC CCA ATT CTT GTT GAA TTA
GAT GGT GAT GTT AAC GGC CAC AAG TTC TCT GTC AGT GGA GAG GGT GAA
GGT GAT GCA ACA TAC GGA AAA CTT ACC CTG AAG TTC ATC TGC ACT ACT

FIG. 8A

```
GGC AAA CTG CCT GTT CCA TGG CCA ACA CTA GTC ACT ACT CTG TGC TAT
GGT GTT CAA TGC TTT TCA AGA TAC CCG GAT CAT ATG AAA CGG CAT GAC
TTT TTC AAG AGT GCC ATG CCC GAA GGT TAT GTA CAG GAA AGG ACC ATC
TTC TTC AAA GAT GAC GGC AAC TAC AAG ACA CGT GCT GAA GTC AAG TTT
GAA GGT GAT ACC CTT GTT AAT AGA ATC GAG TTA AAA GGT ATT GAC TTC
AAG GAA GAT GGC AAC ATT CTG GGA CAC AAA TTG GAA TAC AAC TAT AAC
TCA CAC AAT GTA TAC ATC ATG GCA GAC AAA CAA AAG AAT GGA ATC AAA
GTG AAC TTC AAG ACC CGC CAC AAC ATT GAA GAT GGA AGC GTT CAA CTA
GCA GAC CAT TAT CAA CAA AAT ACT CCA ATT GGC GAT GGC CCT GTC CTT
TTA CCA GAC AAC CAT TAC CTG TCC ACA CAA TCT GCC CTT TCG AAA GAT
CCC AAC GAA AAG AGA GAC CAC ATG GTC CTT CTT GAG TTT GTA ACA GCT
                                                    end GFP →↓
GCT GGG ATT ACA CAT GGC ATG GAT GAA CTG TAC AAC GTG GTT CTT CGG
                                               ↑←Start NLG-1 Motif
ACC GCC TGT CCC CCA GAT TAC ACA CTA GCT ATG AGG AGG TCA CCT GAT
GAT GTT CCC TTA ATG ACA CCC AAC ACC ATT ACA ATG taactcgagt
                                      end NLG1 Motif→↑
ctagacgtgg taccGATAAT CAACCTCTGG ATTACAAAAT TTGTGAAAGA TTGACTGGTA
             ↑←start WPRE
TTCTTAACTA TGTTGCTCCT TTTACGCTAT GTGGATACGC TGCTTTAATG CCTTTGTATC
ATGCTATTGC TTCCCGTATG GCTTTCATTT TCTCCTCCTT GTATAAATCC TGGTTGCTGT
CTCTTTATGA GGAGTTGTGG CCCGTTGTCA GGCAACGTGG CGTGGTGTGC ACTGTGTTTG
CTGACGCAAC CCCCACTGGT TGGGGCATTG CCACCACCTG TCAGCTCCTT TCCGGGACTT
TCGCTTTCCC CCTCCCTATT GCCACGGCGG AACTCATCGC CGCCTGCCTT GCCCGCTGCT
GGACAGGGGC TCGGCTGTTG GGCACTGACA ATTCCGTGGT GTTGTCGGGG AAGCTGACGT
CCTTTCCATG GCTGCTCGCC TGTGTTGCCA CCTGGATTCT GCGCGGGACG TCCTTCTGCT
ACGTCCCTTC GGCCCTCAAT CCAGCGGACC TTCCTTCCCG CGGCCTGCTG CCGGCTCTGC
GGCCTCTTCC GCGTCTTCGC CTTCGCCCTC AGACGAGTCG ATCTCCCTTT GGGCCGCCT
CCCCGCCTGA Tgcggggatc tctagagtc gagagatct4 CGGGTGGCAT CCCTGTGACC
    end WPRE→↑                                 ↑←start bGH-polyA
CCTCCCCAGT GCCTCTCCTG GCCCTGGAAG TTGCCACTCC AGTGCCCACC AGCCTTGTCC
TAATAAAATT AAGTTGCATC ATTTTGTCTG ACTAGGTGTC CTTCTATAAT ATTATGGGGT
GGAGGGGGGT GGTATGGAGC AAGGGGCAAG TTGGGAAGAC AACCTGTAGG GCCTGCGGGG
TCTATTGGGA ACCAAGCTGG AGTGCAGTGG CACAATCTTG GCTCACTGCA ATCTCCGCCT
CCTGGGTTCA AGCGATTCTC CTGCCTCAGC CTCCCGAGTT GTTGGGATTC CAGGCATGCA
TGACCAGGCT CAGCTAATTT TTGTTTTTTT GGTAGAGACG GGGTTTCACC ATATTGGCCA
GGCTGGTCTC AACTCCTAA TCTCAGGTGA TCTACCCACC TTGGCCTCCC AAATTGCTGG
GATTACAGGC GTGAACCACT GCTCCCTTCC CTGTCCTTCt gattttgtag gtaaccacgt
                                      end bGH-polyA→↑
gcggaccgag cggccgcagg aaccccctagt gatggagttg ccactccct ctctgcgcgc
        ↑←start AAV2 ITR
tcgctcgctc actgaggccg gcgaccaaa ggtcgcccga cgcccgggct tgcccgggc
ggcctcagtg agcgagcgag cgcgcagctg cctgcagg
                end AAV2 ITR→↑
```

FIG. 8B

5'-ITR—CAG—ChR2—(NLG-1Motif)—WPRE—bGHpolyA—ITR-3'

←start AAV2 ITR
*cctgcaggca gctgcgcgct cgctcgctca ctgaggccgc ccgggcaaag cccgggcgtc*
*gggcgacctt tggtcgcccg gcctcagtga gcgagcgagc gcgcagagag ggagtggcca*
*actccatcac taggggttcc t*gcggccgca cgcgtgatat CCTAGTTATT AATAGTAATC
              end AAV2 ITR→↑                               ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA

FIG. 9A

```
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGCGGCGGGC GAGGGGCGGG GCGGCGGAGG GGCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                                              end CAG pomoter/enhancer→↓
CAGGGCGGGG TCGGCTTCT GGCCGTGTGAC CGGCGGCTCT AGCAGCGTCT GCTAaccatg
                                                        ↓←start ChR2
ttcatgcctt cttctttttc ctacagctcc tgggcaacgt gctgctgctctc
atcattttgg caaagaatta agcttgagct cgcgatccgc agcc ATG GAT TAT GGA
GGC GCC CTG AGT GCC GTT GGG CGC GAG CTG CTA TTT GTA ACG AAC CCA
GTA GTC GTC AAT GGC TCT GTA CTT GTG CCT GAG GAC CAG TGT TAC TGC
GCG GGC TGG ATT GAG TCG CGT GGC ACA AAC GGT GCC CAA ACG GCG TCG
AAC GTG CTG CAA TGG CTT GCT GCT GGC TTC TCC ATC CTA CTG CTT ATG
TTT TAC GCC TAC CAA ACA TGG AAG TCA ACC TGC GGC TGG GAG GAG ATC
TAT GTG TGC GCT ATC GAG ATG GTC AAG GTG ATT CTT GAG TTC TTC TTC
GAG TTT AAG AAC CCG TCC ATG CTG TAT CTA GCC ACA GGC CAC CGC GTC
CAG TGG TTG CGT TAC GCC GAG TGG CTT CTC ACC TGC CCG GTC ATT CTC
ATT CAC CTG TCA AAC CTG ACG GGC TTG TCC AAC GAC TAC AGC AGG CGC
ACT ATG GGT CTG CTT GTG TCT GAT ATT GGC ACA ATT GTG TGG GGC GCC
ACT TCC GCT ATG GCC ACC GGA TAC GTC AAG GTC ATC TTC TTC TGC CTG
GGT CTG TGT TAT GGT GCT AAC ACG TTC TTT CAC GCT GCC AAG GCC TAC
ATC GAG GGT TAC CAT ACC GTG CCG AAG GGC CGG TGT CGC CAG GTG GTG
ACT GGC ATG GCT TGG CTC TTC TTC GTA TCA TGG GGT ATG TTC CCC ATC
CTG TTC ATC CTC GGC CCC GAG GGC TTC GGC GTC CTG AGC GTG TAC GGC
TCC ACC GTC GGC CAC ACC ATC ATT GAC CTG ATG TCG AAG AAC TGC TGG
GGT CTG CTC GGC CAC TAC CTG CGC GTG CTG ATC CAC GAG CAT ATC CTC
ATC CAC GGC GAC ATT CGC AAG ACC ACC AAA TTG AAC ATT GGT GGC ACT
GAG ATT GAG GTC GAG ACG CTG GTG GAG GAC GAG GCC GAG GCT GGC GCG
GTC AAC AAG GGC ACC GGC AAG gaattcggag gcggaggtgg agctagc
                   end ChR2→↑
GTG GTT CTT CGG ACC GCC TGT CCC CCA GAT TAC ACA CTA GCT ATG AGG
↑←Start NLG-1 Motif
AGG TCA CCT GAT GAT GTT CCC TTA ATG ACA CCC AAC ACC ATT ACA ATG
                                                       end NLG1 Motif→↑
taactcgagt ctagacgtgg taccGATAAT CAACCTCTGG ATTACAAAAT TTGTGAAAGA
            ↑←start WPRE
TTGACTGGTA TTCTTAACTA TGTTGCTCCT TTTACGCTAT GTGGATACGC TGCTTTAATG
CCTTTGTATC ATGCTATTGC TTCCCGTATG GCTTTCATTT TCTCCTCCTT GTATAAATCC
TGGTTGCTGT CTCTTTATGA GGAGTTGTGG CCCGTTGTCA GGCAACGTGG CGTGGTGTGC
ACTGTGTTTG CTGACGCAAC CCCCACTGGT TGGGGCATTG CCACCACCTG TCAGCTCCTT
TCCGGGACTT TCGCTTTCCC CCTCCCTATT GCCACGGCGG AACTCATCGC CGCCTGCCTT
GCCCGCTGCT GGACAGGGGC TCGGCTGTTG GGCACTGACA ATTCCGTGGT GTTGTCGGGG
AAGCTGACGT CCTTTCCATG GCTGCTCGCC TGTGTTGCCA CCTGGATTCT GCGCGGGACG
TCCTTCTGCT ACGTCCCTTC GGCCCTCAAT CCAGCGGACC TTCCTTCCCG CGGCCTGCTG
CCGGCTCTGC GGCCTCTTCC GCGTCTTCGC CTTCGCCCTC AGACGAGTCG GATCTCCCTT
TGGGCCGCCT CCCCGCCTGA TgcggggatC ctctagagtc gagagatctA CGGGTGGCAT
            end WPRE→↑                                ↑←start bGH-polyA
CCCTGTGACC CCTCCCCAGT GCCTCTCCTG GCCCTGGAAG TTGCCACTCC AGTGCCCACC
AGCCTTGTCC TAATAAAATT AAGTTGCATC ATTTTGTCTG ACTAGGTGTC CTTCTATAAT
ATTATGGGGT GGAGGGGGGT GGTATGGAGC AAGGGGCAAG TTGGGAAGAC AACCTGTAGG
GCCTGCGGGG TCTATTGGGA ACCAAGCTGG AGTGCAGTGG CACAATCTTG GCTCACTGCA
ATCTCCGCCT CCTGGGTTCA AGCGATTCTC CTGCCTCAGC CTCCCGAGTT GTTGGGATTC
CAGGCATGCA TGACCAGGCT CAGCTAATTT TTGTTTTTTT GGTAGAGACG GGGTTTCACC
ATATTGGCCA GGCTGGTCTC CAACTCCTAA TCTCAGGTGA TCTACCCACC TTGGCCTCCC
AAAATGCTGG GATTACAGGC GTGAACCACT GCTCCCTTCC CTGTCCTTCt gattttgtag
                                              end bGH-polyA→↑
gtaaccacgt gcggaccgag cggccgcagg aaccccctagt gatggagttg gccactcccc
                                ↑←start AAV2 ITR
ctctgcgcgc tcgctcgctc actgaggccg ggcgaccaaa ggtcgcccga cgcccgggct
ttgcccgggc ggcctcagtg agcgagcgag cgcgcagcta cctgcagg
                                         end AAV2 ITR→↑
```

FIG. 9B

5'-ITR—CAG—ChR2—GFP—(MLPH Motif)—WPRE—bGHpolyA—ITR-3'

←start AAV2 ITR
<u>cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac tagggg̲ttcc</u> tgcggccgca cgcgtgatat CCTAGTTATT AATAGTAATC
    end AAV2 ITR→↑            ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGGTCG AGGTGA
GCCCCACGTT CTGCTTCACT CTCCCCATCT CCCCCCCCTC CCCACCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                 end CAG pomoter/enhancer→↓
CAGGGCGGGG TTCGGCTTCT GGCGTGTGAC CGGCGGCTCT AGCAGCCTCT GCTAaccatg
ttcatgcctt cttcttttc ctacagctcc tgggcaacgt gctggttatt gtgctgtctc
                       ↓←start ChR2
atcattttgg caaagaatta agcttgagct cgcgatccgc agcc ATG GAT TAT GGA
GGC GCC CTG AGT GCC GTT GGG CGC GAG CTG CTA TTT GTA ACG AAC CCA
GTA GTC GTC AAT GGC TCT GTA CTT GTG CCT GAG GAC CAG TGT TAC TGC
GCG GGC TGG ATT GAG TCG CGT GGC ACA AAC GGT GCC CAA ACG GCG TCG
AAC GTG CTG CAA TGG CTT GCT GCT GGC TTC TCC ATC CTA CTG CTT ATG
TTT TAC GCC TAC CAA ACA TGG AAG TCA ACC TGC GGC TGG GAG GAG ATC
TAT GTG TGC GCT ATC GAG ATG GTC AAG GTG ATT CTT GAG TTC TTC TTC
GAG TTT AAG AAC CCG TCC ATG CTG TAT CTA GCC ACA GGC CAC CGC GTC
CAG TGG TTG CGT TAC GCC GAG TGG CTT CTC ACC TGC CCG GTC ATT CTC
ATT CAC CTG TCA AAC CTG ACG GGC TTG TCC AAC GAC TAC AGC AGG CGC
ACT ATG GGT CTG CTT GTG TCT GAT ATT GGC ACA ATT GTG TGG GGC GCC
ACT TCC GCT ATG GCC ACC GGA TAC GTC AAG GTC ATC TTC TTC TGC CTG
GGT CTG TGT TAT GGT GCT AAC ACG TTC TTT CAC GCT GCC AAG GCC TAC
ATC GAG GGT TAC CAT ACC GTG CCG AAG GGC CGG TGT CGC CAG GTG GTG
ACT GGC ATG GCT TGG CTC TTC TTC GTA TCA TGG GGT ATG TTC CCC ATC
CTG TTC ATC CTC GGC CCC GAG GGC TTC GGC GTC CTG AGC GTG TAC GGC
TCC ACC GTC GGC CAC ACC ATC ATT GAC CTG ATG TCG AAG AAC TGC TGG
GGT CTG CTC GGC CAC TAC CTG CGC GTG CTG ATC CAC GAG CAT ATC CTC
ATC CAC GGC GAC ATT CGC AAG ACC ACC AAA TTG AAC ATT GGT GGC ACT
GAG ATT GAG GTC GAG ACG CTG GTG GAG GAC GAG GCC GAG GCT GGC GCG

FIG. 10A

```
GTC AAC AAG GGC ACC GGC AAG   gaattcggag gcggaggtgg agctagc
                  end ChR2→↑
↓←start GFP
AAA GGA GAA GAA CTC TTC ACT GGA GTT GTC CCA ATT CTT GTT GAA TTA
GAT GGT GAT GTT AAC GGC CAC AAG TTC TCT GTC AGT GGA GAG GGT GAA
GGT GAT GCA ACA TAC GGA AAA CTT ACC CTG AAG TTC ATC TGC ACT ACT
GGC AAA CTG CCT GTT CCA TGG CCA ACA CTA GTC ACT ACT CTG TGC TAT
GGT GTT CAA TGC TTT TCA AGA TAC CCG GAT CAT ATG AAA CGG CAT GAC
TTT TTC AAG AGT GCC ATG CCC GAA GGT TAT GTA CAG GAA AGG ACC ATC
TTC TTC AAA GAT GAC GGC AAC TAC AAG ACA CGT GCT GAA GTC AAG TTT
GAA GGT GAT ACC CTT GTT AAT AGA ATC GAG TTA AAA GGT ATT GAC TTC
AAG GAA GAT GGA AAC ATT CTG GGA CAC AAA TTG GAA TAC AAC TAT AAC
TCA CAC AAT GTA TAC ATC ATG GCA GAC AAA CAA AAG AAT GGA ATC AAA
GTG AAC TTC AAG ACC CGC CAC AAC ATT GAA GAT GGA AGC GTT CAA CTA
GCA GAC CAT TAT CAA CAA AAT ACT CCA ATT GGC GAT GGC CCT GTC CTT
TTA CCA GAC AAC CAT TAC CTG TCC ACA CAA TCT GCC CTT TCG AAA GAT
CCC AAC GAA AAG AGA GAC CAC ATG GTC CTT CTT GAG TTT GTA ACA GCT
                                                     end GFP→↓
GCT GGG ATT ACA CAT GGC ATG GAT GAA CTG TAC AAC AGG GAC CAG CCT
                                               ↑←Start MLPH Motif
CTG AAC AGC AAA AAG AAA AAG AGG CTC CTG AGC TTC AGG GAC GTG GAC
TTC GAG GAG GAC AGC GAC taactcgagt ctagacgtgg taccGATAAT CAACCTCTGG
   end MLPH Motif→↑                                ↑←start WPRE
ATTACAAAAT TTGTGAAAGA TTGACTGGTA TTCTTAACTA TGTTGCTCCT TTTACGCTAT
GTGGATACGC TGCTTTAATG CCTTTTGTATC ATGCTATTGC TTCCCGTATG GCTTTCATTT
TCTCCTCCTT GTATAAATCC TGGTTGCTGT CTCTTTATGA GGAGTTGTGG CCCGTTGTCA
GGCAACGTGG CGTGGTGTGC ACTGTGTTTG CTGACGCAAC CCCCACTGGT TGGGGCATTG
CCACCACCTG TCAGCTCCTT TCCGGGACTT TCGCTTTCCC CCTCCCTATT GCCACGGCGG
AACTCATCGC CGCCTGCCTT GCCCGCTGCT GGACAGGGGC TCGGCTGTTG GGCACTGACA
ATTCCGTGGT GTTGTCGGGG AAGCTGACGT CCTTTCCATG GCTGCTCGCC TGTGTTGCCA
CCTGGATTCT GCGCGGGACG TCCTTCTGCT ACGTCCCTTC GGCCCTCAAT CCAGCGGACC
TTCCTTCCCG CGGCCTGCTG CCGGCTCTGC GGCCTCTTCC GCGTCTTCGC CTTCGCCCTC
AGACGAGTCG GATCTCCCTT TGGGCCGCCT CCCCGCCTGA Tgcggggatc ctctagagtc
                                    end WPRE→↑
gagagatctA CGGGTGGCAT CCCTGTGACC CCTCCCCAGT GCCTCTCCTG GCCCTGGAAG
         ↑←start bGH-polyA
TTGCCACTCC AGTGCCCACC AGCCTTGTCC TAATAAAATT AAGTTGCATC ATTTTGTCTG
ACTAGGTGTC CTTCTATAAT ATTATGGGGT GGAGGGGGGT GGTATGGAGC AAGGGGCAAG
TTGGAAGAC AACCTGTAGG GCCTGCGGGG TCTATTGGGA ACCAAGCTGG AGTGCAGTGG
CACAATCTTG GCTCACTGCA ATCTCCGCCT CCTGGGTTCA AGCGATTCTC CTGCCTCAGC
CTCCCGAGTT GTTGGGATTC CAGGCATGCA TGACCAGGCT CAGCTAATTT TTGTTTTTTT
GGTAGAGACG GGGTTTCACC ATATTGGCCA GGCTGGTCTC AACTCCTAA TCTCAGGTGA
TCTACCCACC TTGGCCTCCC AAATTGCTGG GATTACAGGC GTGAACCACT GCTCCCTTCC
CTGTCCTTct gattttgtag gtaaccacgt gcggaccgag cggccgcagg aaccccctagt
         ↑←end bGH-polyA                           ↑←start AAV2 ITR
gatggagttg gccactccct ctctgcgcgc tcgctcgctc actgaggccg ggcgaccaaa
ggtcgcccga cgcccgggct ttgcccgggc ggcctcagtg agcgagcgag cgcgcagctg
cctgcagg
   ↑←end AAV2 ITR
```

FIG. 10B

5'-ITR—CAG—ChR2—(MLPH-Motif)—WPRE—bGHpolyA—ITR-3'

←start AAV2 ITR
cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac taggggttcc tgcggccgca cgcgtgatat CCTAGTTATT AATAGTAATC
            end AAV2 ITR→↑                    ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGGTCG AGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                                    end CAG pomoter/enhancer→↓
CAGGGCGGGG TTCGGCTTCT GGCGTGTGAC CGGCGGCTCT AGCAGCCTCT GCTAaccatg
ttcatgcctt cttctttttc ctacagctcc tgggcaacgt gctggttatt gtgctgtctc
                                                        ↓←start ChR2
atcattttgg caaagaatta agcttgagct cgcgatccgc agcc ATG GAT TAT GGA
GGC GCC CTG AGT GCC GTT GGG CGC GAG CTG CTA TTT GTA ACG AAC CCA
GTA GTC GTC AAT GGC TCT GTA CTT GTG CCT GAG GAC CAG TGT TAC TGC
GCG GGC TGG ATT GAG TCG CGT GGC ACA AAC GGC GCC CAA ACG GCG TCG
AAC GTG CTG CAA TGG CTT GCT GCT GGC TTC TCC ATC CTA CTG CTT ATG
TTT TAC GCC TAC CAA ACA TGG AAG TCA ACC TGC GGC TGG GAG GAG ATC
TAT GTG TGC GCT ATC GAG ATG GTC AAG GTG ATT CTT GAG TTC TTC TTC
GAG TTT AAG AAC CCG TCC ATG CTG TAT CTA GCC ACA GGC CAC CGC GTC
CAG TGG TTG CGT TAC GCC GAG TGG CTT CTC ACC TGC CCG GTC ATT CTC
ATT CAC CTG TCA AAC CTG ACG GGT TTG TCC AAC GAC TAC AGC AGG CGC
ACT ATG GGT CTG CTT GTG TCT GAT ATT GGC ACA ATT GTG TGG GGC GCC
ACT TCC GCT ATG GCC ACC GGA TAC GTC AAG GTC ATC TTC TTC TGC CTG
GGT CTG TGT TAT GGT GCT AAC ACG TTC TTT CAC GCT GCC AAG GCC TAC
ATC GAG GGT TAC CAT ACC GTG CCG AAG GGC CGG TGT CGC CAG GTG GTG
ACT GGC ATG GCT TGG CTC TTC TTC GTA TCA TGG GGT ATG TTC CCC ATC
CTG TTC ATC CTC GGC CCC GAG GGC TTC GGC GTC CTG AGC GTG TAC GGC
TCC ACC GTC GGC CAC ACC ATC ATT GAC CTG ATG TCG AAG AAC TGC TGG
GGT CTG CTC GGC CAC TAC CTG CGC GTG CTG ATC CAC GAG CAT ATC CTC
ATC CAC GGC GAC ATT CGC AAG ACC ACC AAA TTG AAC ATT GGT GGC ACT
GAG ATT GAG GTC GAG ACG CTG GTG GAG GAC GAG GCC GAG GCT GGC GCG
GTC AAC AAG GGC ACC GGC AAG gaattcggag gcggaggtgg agctagc
            end ChR2→↑
AGG GAC CAG CCT CTG AAC AGC AAA AAG AAA AAG AGG CTC CTG AGC TTC
↑←Start MLPH Motif
AGG GAC GTG GAC TTC GAG GAG GAC AGC GAC taactcgagt ctagacgtgg
                                end MLPH Motif→↑
taccGATAAT CAACCTCTGG ATTACAAAAT TTGTGAAAGA TTGACTGGTA TTCTTAACTA
    ↑←start WPRE
TGTTGCTCCT TTTACGCTAT GTGGATACGC TGCTTTAATG CCTTTGTATC ATGCTATTGC
TTCCGTATG GCTTTCATTT TCTCCTCCTT GTATAAATCC TGGTTGCTGT CTCTTTATGA
GGAGTTGTGG CCCGTTGTCA GGCAACGTGG CGTGGTGTGC ACTGTGTTTG CTGACGCAAC
CCCCACTGGT TGGGGCATTG CCACCACCTG TCAGCTCCTT TCCGGGACTT TCGCTTTCCC
CCTCCCTATT GCCACGGCGG AACTCATCGC CGCCTGCCTT GCCCGCTGCT GGACAGGGGC
TCGGCTGTTG GGCACTGACA ATTCCGTGGT GTTGTCGGGGA AGCTGACGT CCTTTCCATG
GCTGCTCGCC TGTGTTGCCA CCTGGATTCT GCGCGGGACG TCCTTCTGCT ACGTCCCTTC
GGCCCTCAAT CCAGCGGACC TTCCTTCCCG CGGCCTGCTG CCGGCTCTGC GGCCTCTTCC
GCGTCTTCGC CTTCGCCCTC AGACGAGTCG GATCTCCCTT TGGGCCGCCT CCCCGCCTGA
Tgcgggggatc ctctagagtc gagagatct4 CGGGTGGCAT CCCTGTGACC CCTCCCCAGT
↑←end WPRE                                ↑←start bGH-polyA

FIG. 11A

```
GCCTCTCCTG GCCCTGGAAG TTGCCACTCC AGTGCCCACC AGCCTTGTCC TAATAAAATT
AAGTTGCATC ATTTTGTCTG ACTAGGTGTC CTTCTATAAT ATTATGGGGT GGAGGGGGGT
GGTATGGAGC AAGGGGCAAG TTGGGAAGAC AACCTGTAGG GCCTGCGGGG TCTATTGGGA
ACCAAGCTGG AGTGCAGTGG CACAATCTTG GCTCACTGCA ATCTCCGCCT CCTGGGTTCA
AGCGATTCTC CTGCCTCAGC CTCCCGAGTT GTTGGGATTC CAGGCATGCA TGACCAGGCT
CAGCTAATTT TTGTTTTTTT GGTAGAGACG GGGTTTCACC ATATTGGCCA GGCTGGTCTC
CAACTCCTAA TCTCAGGTGA TCTACCCACC TTGGCCTCCC AAATTGCTGG GATTACAGGC
GTGAACCACT GCTCCCTTCC CTGTCCTTCt gattttgtag gtaaccacgt gcggaccgag
            end bGH-polyA → ↑
cggccgc agg aacccctagt gatggagttg gccactccct ctctgcgcgc tcgctcgctc
        ↑ ← start AAV2 ITR
actgaggccg ggcgaccaaa ggtcgcccga cgcccgggct ttgcccgggc ggcctcagtg
agcgagcgag cgcgcagctg cctgcagg
            end AAV2 ITR → ↑
```

FIG. 11B

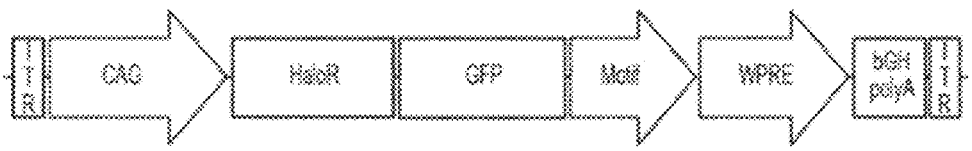

5'-ITR—CAG—HaloR—GFP—(Kv2.1Motif)—WPRE—bGHpolyA—ITR-3

```
←start AAV2 ITR
cctgcaggca gctgcgcgct cactcgctca ctgaggccgc ccgggcaaag cccgggcgtc
gggcgacctt tggtcgcccg gcctcagtga gcgagcgagc gcgcagagag ggagtggcca
actccatcac tagggggttcc tgcggccgca cgcgtgatat CCTAGTTATT AATAGTAATC
            end AAV2 ITR→ ↑                        ↑ ← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGCGAGC GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
            end CAG pomoter/enhancer → ↓
CAGGGCGGGG TTCGGCTTCT GGCGTGTGAC CGGCGGCTCT AGCAGCCTCT GCTAaccatg
ttcatgcctt cttcttttc ctacagctcc tgggcaacgt gctggttatt gtgctgtctc
            ↓ ← start HaloR
atcattttgg caaagaatta agcttgagct cgcgatccgc agcc ATG ACT GAG ACA
TTG CCA GGT GTA ACG GAA TCG GCT GTT GCG CTA CAG GCG GAG GTG ACC
CAG AGG GAG CTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG ACG ATT TTG GTG CCG GTG GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GGC GAA GAG GTA GAC GGC
```

FIG. 12A

GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
CTC TTT ACC GCC ATC ACC TTC GAC ATC GCG ATG TGT GTC ACC GGC CTC
GCA GCC GCG CTG ACG ACC TCT TCG CAC CTG ATG CGG TGG TTC TGG TAC
GCC ATC AGT TGT GCG TGT TTC CTC GTC GTC CTC TAC ATC CTG CTC GTC
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
                                                                    end HaloR→↑
gaattcggag gcggaggtgg agctagc AAA GGA GAA GAA CTC TTC ACT GGA GTT
               ↑←start GFP
GGA GTT GTC CCA ATT CTT GTT GAA TTA GAT GGT GAT GTT AAC GGC CAC
AAG TTC TCT GTC AGT GGA GAG GGT GAA GGT GAT GCA ACA TAC GGA AAA
CTT ACC CTG AAG TTC ATC TGC ACT ACT GGC AAA CTG CCT GTT CCA TGG
CCA ACA CTA GTC ACT ACT CTG TGC TAT GGT GTT CAA TGC TTT TCA AGA
TAC CCG GAT CAT ATG AAA CGG CAT GAC TTT TTC AAG AGT GCC ATG CCC
GAA GGT TAT GTA CAG GAA AGG ACC ATC TTC TTC AAA GAT GAC GGG AAC
TAC AAG ACA CGT GCT GAA GTC AAG TTT GAA GGT GAT ACC CTT GTT AAT
AGA ATC GAG TTA AAA GGT ATT GAC TTC AAG GAA GAT GGC AAC ATT CTG
GGA CAC AAA TTG GAA TAC AAC TAT AAC TCA CAC AAT GTA TAC ATC ATG
GCA GAC AAA CAA AAG AAT GGA ATC AAA GTG AAC TTC AAG ACC CGC CAC
AAC ATT GAA GAT GGA AGC GTT CAA CTA GCA GAC CAT TAT CAA CAA AAT
ACT CCA ATT GGC GAT GGC CCT GTC CTT TTA CCA GAC AAC CAT TAC CTG
TCC ACA CAA TCT GCC CTT TCG AAA GAT CCC AAC GAA AAG AGA GAC CAC
ATG GTC CTT CTT GAG TTT GTA ACA GCT GCT GGG ATT ACA CAT GGC ATG
          end GFP →↓
GAT GAA CTG TAC AAC CAG TCT CAG CCC ATC CTG AAC ACT AAG GAG ATG
                          ↑←Start Kv2.1 Motif
GCC CCT CAG AGT AAA CCC CCT GAG GAA CTG GAA ATG AGC TCC ATG CCA
TCT CCA GTG GCT CCT CTG CCA GCT AGG ACC GAG GGC GTG ATT GAC ATG
AGA AGC ATG TCT AGT ATC GAT AGC TTC ATT TCC TGC GCC ACC GAC TTC
CCC GAA GCT ACA AGG TTT taactcgagt ctagacgtgg taccGATAAT CAACCTCTGG
       end Kv2.1 Motif→↑                                  ↑←start WPRE
ATTACAAAAT TTGTGAAAGA TTGACTGGTA TTCTTAACTA TGTTGCTCCT TTTACGCTAT
GTGGATACGC TGCTTTAATG CCTTTGTATC ATGCTATTGC TTCCCGTATG GCTTTCATTT
TCTCCTCCTT GTATAAATCC TGGTTGCTGT CTCTTTATGA GGAGTTGTGG CCCGTTGTCA
GGCAACGTGG CGTGGTGTGC ACTGTGTTTG CTGACGCAAC CCCCACTGGT TGGGGCATTG
CCACCACCTG TCAGCTCCTT TCCGGGACTT TCGCTTTCCC CCTCCCTATT GCCACGGCGG
AACTCATCGC CGCCTGCCTT GCCCGCTGCT GGACAGGGGC TCGGCTGTTG GGCACTGACA
ATTCCGTGGT GTTGTCGGGG AAGCTGACGT CCTTTCCATG GCTGCTCGCC TGTGTTGCCA
CCTGGATTCT GCGCGGGACG TCCTTCTGCT ACGTCCCTTC GGCCCTCAAT CCAGCGGACC
TTCCTTCCCG CGGCCTGCTG CCGGCTCTGC GGCCTCTTCC GCGTCTTCGC CTTCGCCCTC
AGACGAGTCG GATCTCCCTT TGGGCCGCCT CCCCGCCTGA Tgcggggatc ctctagagtc
                                       end WPRE→↑
gagagatctA CGGGTGGCAT CCCTGTGACC CCTCCCCAGT GCCTCTCCTG GCCCTGGAAG
       ↑←start bGH-polyA
TTGCCACTCC AGTGCCCACC AGCCTTGTCC TAATAAAATT AAGTTGCATC ATTTTGTCTG
ACTAGGTGTC CTTCTATAAT ATTATGGGGT GGAGGGGGGT GGTATGGAGC AAGGGGCAAG
TTGGAAGAC AACCTGTAGG GCCTGCGGGG TCTATTGGGA ACCAAGCTGG AGTGCAGTGG
CACAATCTTG GCTCACTGCA ATCTCCGCCT CCTGGGTTCA AGCGATTCTC CTGCCTCAGC
CTCCCGAGTT GTTGGGATTC CAGGCATGCA TGACCAGGCT CAGCTAATTT TTGTTTTTTT
GGTAGAGACG GGGTTTCACC ATATTGGCCA GGCTGGTCTC CAACTCCTAA TCTCAGGTGA
TCTACCCACC TTGGCCTCCC AAATTGCTGG GATTACAGGC GTGAACCACT GCTCCCTTCC
CTGTCCTTCt gattttgtag gtaaccacgt gcggaccgag cggccgcagg aaccccctagt
       ↑← endbGH-polyA                                       ↑←start AAV2 ITR gatggagttg gccactccct ctctgcgcgc tcgctcgctc actgaggccg ggcgaccaaa
ggtcgcccga cgcccgggct ttgcccgggc ggcctcagtg agcgagcgag cgcgcagctg
cctgcagg
       ↑←end AAV2 ITR

FIG. 12B

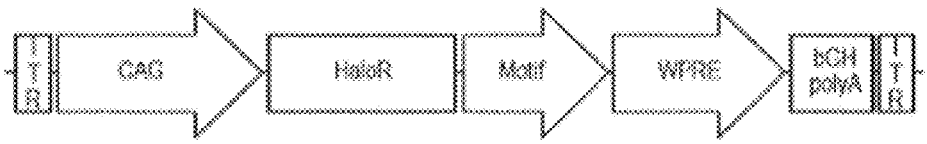

5'-ITR—CAG—HaloR—(Kv2.1Motif)—WPRE—bGHpolyA—ITR-3'

←start AAV2 ITR
*cctgcaggca gctgcgcgct tcgctcgctca ctgaggccgc ccgggcaaag cccgggcgtc*
*gggcgacctt tggtcgcccg gcctcaatga gcgagcgagc gcgcagagag ggagtggcca*
*actccatcac tagggggttcc* tgcggccgca cgcgtgatat CCTAGTTATT AATAGTAATC
     end AAV2 ITR→↑        ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                           end CAG pomoter/enhancer→↓
CAGGGCGGGG TTCGGCTTCT GGCGTGTGAC CGGCGGCTCT AGCAGCCTCT GCTAaccatg
ttcatgcctt cttcttttc ctacagctcc tgggcaacgt gctggttatt gtgctgtctc
                       ↓←start HaloR
atcattttgg caaagaatta agcttgagct cgcgatccgc agcc *ATG ACT GAG ACA*
*TTG CCA CCG GTA ACG GAA TCG GCT GTT GCG CTA CAG GCG GAG GTG ACC*
*CAG AGG GAG CTG TTC GAG TTC GTT CTC AAC GAC CCC CTC CTC GCC AGT*
*TCG CTG TAT ATT AAT ATC GCA CTG GCA GGG CTG TCG ATA CTG CTT TTC*
*GTG TTC ATG ACG CGC GGA CTC GAC GAC CCA CGG GCG AAA CTC ATC GCC*
*GTT TCG ACG ATT TTG GTG CCG GTG GTC TCT ATC GCG AGC TAC ACC GGC*
*CTT GCA TCG GGG CTC ACC ATC AGC GTC CTC GAG ATG CCA GCC GGC CAC*
*TTC GCC GAG GGG TCC TCG GTG ATG CTC GGC GGC GAA GAG GTA GAC GGC*
*GTC GTG ACG ATG TGG GGC CGC TAT CTG ACG TGG GCC CTT TCG ACA CCG*
*ATG ATA CTG CTG GCG CTT GGG CTG CTT GCT GGC TCT AAC GCC ACG AAG*
*CTC TTT ACC GCC ATC ACC TTC GAC ATC GCG ATG TGT GTC ACC GGC CTC*
*GCA GCC GCG CTG ACG ACC TCT TCG CAC CTG ATG CGG TGG TTC TGG TAC*
*GCC ATC AGT TGT GCG TGT TTC CTC GTC GTC CTC TAC ATC CTG CTC GTC*
*GAG TGG GCA CAG GAC GCC AAG GCT GCC GGT ACT GCG GAT ATG TTC AAT*
*ACG CTG AAG CTG CTG ACC GTT GTC ATG TGG CTC GGC TAC CCC ATC GTG*
*TGG GCA CTC GGC GTT GAG GGC ATC GCC GTT CTT CCG GTC GGA GTC ACG*
*TCG TGG GGA TAC AGC TTC CTC GAC ATC GTC GCG AAG TAC ATC TTC GCG*
*TTC CTG CTG CTC AAC TAC CTC ACG TCG AAC GAG AGC GTC GTC TCC GGC*
*TCG ATA CTC GAC GTG CCG TCC GCG TCG GGC ACT CCC GCT GAC GAC*
                              end HaloR→↑

FIG. 13A

```
gaattcggag gcggaggtgg agctagc CAG TCT CAG CCC ATC CTG AAC ACT AAG
                              ↑←Start Kv2.1 Motif
GAG ATG GCC CCT CAG AGT AAA CCC CCT GAG GAA CTG GAA ATG AGC TCC
ATG CCA TCT CCA GTG GCT CCT CTG CCA GCT AGG ACC GAG GGC GTG ATT
GAC ATG AGA AGC ATG TCT AGT ATC GAT AGC TTC ATT TCC TGC GCC ACC
GAC TTC CCC GAA GCT ACA AGG TTT taactcgagt ctagacgtgg taccGATAAT
                end Kv2.1 Motif→↑                         ↑←start WPRE
CAACCTCTGG ATTACAAAAT TTGTGAAAGA TTGACTGGTA TTCTTAACTA TGTTGCTCCT
TTTACGCTAT GTGGATACGC TGCTTTAATG CCTTTGTATC ATGCTATTGC TTCCCGTATG
GCTTTCATTT TCTCCTCCTT GTATAAATCC TGGTTGCTGT CTCTTTATGA GGAGTTGTGG
CCCGTTGTCA GGCAACGTGG CGTGGTGTGC ACTGTGTTTG CTGACGCAAC CCCCACTGGT
TGGGGCATTG CCACCACCTG TCAGCTCCTT TCCGGGACTT TCGCTTTCCC CCTCCCTATT
GCCACGGCGG AACTCATCGC CGCCTGCCTT GCCCGCTGCT GGACAGGGGC TCGGCTGTTG
GGCACTGACA ATTCCGTGGT GTTGTCGGGG AAGCTGACGT CCTTTCCATG GCTGCTCGCC
TGTGTTGCCA CCTGGATTCT GCGCGGGACG TCCTTCTGCT ACGTCCCTTC GGCCCTCAAT
CCAGCGGACC TTCCTTCCCG CGGCCTGCTG CCGGCTCTGC GGCCTCTTCC GCGTCTTCGC
CTTCGCCCTC AGACGAGTCG GATCTCCCTT TGGGCCGCCT CCCCGCCTGA Tgcggggatc
                                                end WPRE→↑
ctctagagtc gagagatctA CGGGTGGCAT CCCTGTGACC CCTCCCCAGT GCCTCTCCTG
           ↑←start bGH-polyA
GCCCTGGAAG TTGCCACTCC AGTGCCCACC AGCCTTGTCC TAATAAAATT AAGTTGCATC
ATTTTGTCTG ACTAGGTGTC CTTCTATAAT ATTATGGGGT GGAGGGGGGT GGTATGGAGC
AAGGGGCAAG TTGGGAAGAC AACCTGTAGG GCCTGCGGGG TCTATTGGGA ACCAAGCTGG
AGTGCAGTGG CACAATCTTG GCTCACTGCA ATCTCCGCCT CCTGGGTTCA AGCGATTCTC
CTGCCTCAGC CTCCCGAGTT GTTGGGATTC CAGGCATGCA TGACCAGGCT CAGCTAATTT
TTGTTTTTTT GGTAGAGACG GGGTTTCACC ATATTGGCCA GGCTGGTCTC CAACTCCTAA
TCTCAGGTGA TCTACCCACC TTGGCCTCCC AAATTGCTGG GATTACAGGC GTGAACCACT
GCTCCCTTCC CTGTCCTTct gattttgtag gtaaccacgt gcggaccgag
     end bGH-polyA→↑
cggccgcagg aaccccctagt gatggagttg gccactccct ctctgcgcgc tcgctcgctc
           ↑←start AAV2 ITR
actgaggccg ggcgaccaaa ggtcgcccga cgcccgggct tgcccgggc ggcctcagtg
agcgagcgag cgcgcagctg cctgcagg
               end AAV2 ITR→↑
```

FIG. 13B

5'-ITR—CAG—HaloR—GFP—(Nav1.6 Motif)—WPRE—bGHpolyA—ITR-3'

←start AAV2 ITR
*cctgcaggca gctgcgcgct cgctcgctca ctgaggccgc ccgggcaaag cccgggcgtc*
*gggcgacctt tggtcgcccg gcctcagtga gcgagcgagc gcgcagagag ggagtggcca*
*actccatcac taggggttcc* tgcggccgca cgcgtgatat CCTAGTTATT AATAGTAATC
          end AAV2 ITR→↑                           ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG

FIG. 14A

```
TGCGGGGGGA GCGGCTCGGG GCTGTCCGCG GGGGACGGC TGCCTTCGGG GGGGACGGGG
                                              end CAG pomoter/enhancer→↓
CAGGGCGGGG TTCGGCTTCT GGCGTGTGAC CGGCGGCTCT AGCAGCCTCT GCTAaccatg
ttcatgcctt cttcttttc ctacagctcc tgggcaacgt gctggttatt gtgctgtctc
                                                      ↓←start HaloR
atcattttgg caaagaatta agcttgagct cgcgatccgc agcc ATG ACT GAG ACA
TTG CCA CCG GTA ACG GAA TCG GCT GTT GCG CTA CAG GCG GAG GTG ACC
CAG AGG GAG CTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG ACG ATT TTG GTG CCG GTG GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GGC GAA GAG GTA GAC GGC
GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
CTC TTT ACC GCC ATC ACC TTC GAC ATC GCG ATG TGT GTC ACC GGC CTC
GCA GCC GCG CTG ACG ACC TCT TCG CAC CTG ATG CGG TGG TTC TGG TAC
GCC ATC AGT TGT GCG TGT TTC CTC GTC GTC CTC TAC ATC CTG CTC GTC
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
                                              end HaloR→↑
gaattcggag gcggaggtgg agctagc AAA GGA GAA GAA CTC TTC ACT GGA GTT
                              ↑←start GFP
GGA GTT GTC CCA ATT CTT GTT GAA TTA GAT GGT GAT GTT AAC GGC CAC
AAG TTC TCT GTC AGT GGA GAG GGT GAA GGT GAT GCA ACA TAC GGA AAA
CTT ACC CTG AAG TTC ATC TGC ACT ACT GGC AAA CTG CCT GTT CCA TGG
CCA ACA CTA GTC ACT ACT CTG TGC TAT GGT GTT CAA TGC TTT TCA AGA
TAC CCG GAT CAT ATG AAA CGG CAT GAC TTT TTC AAG AGT GCC ATG CCC
GAA GGT TAT GTA CAG GAA AGG ACC ATC TTC TTC AAA GAT GAC GGC AAC
TAC AAG ACA CGT GCT GAA GTC AAG TTT GAA GGT GAT ACC CTT GTT AAT
AGA ATC GAG TTA AAA GGT ATT GAC TTC AAG GAA GAT GGC AAC ATT CTG
GGA CAC AAA TTG GAA TAC AAC TAT AAC TCA CAC AAT GTA TAC ATC ATG
GCA GAC AAA CAA AAG AAT GGA ATC AAA GTG AAC TTC AAG ACC CGC CAC
AAC ATT GAA GAT GGA AGC GTT CAA CTA GCA GAC CAT TAT CAA CAA AAT
ACT CCA ATT GGC GAT GGC CCT GTC CTT TTA CCA GAC AAC CAT TAC CTG
TCC ACA CAA TCT GCC CTT TCG AAA GAT CCC AAC GAA AAG AGA GAC CAC
ATG GTC CTT CTT GAG TTT GTA ACA GCT GCT GGG ATT ACA CAT GGC ATG
            end GFP →↓
GAT GAA CTG TAC AAC ACC GTG AGG GTG CCC ATC GCC GTG GGC GAG AGC
                   ↑←Start Nav1.6 Motif→↑
GAC TTC GAG AAC CTG AAC ACC GAG GAC GTG AGC AGC GAG AGC GAC CCC
                                             end Nav1.6 Motif→↑
taactcgagt ctagacgtgg taccGATAAT CAACCTCTGG ATTACAAAAT TTGTGAAAGA
                          ↑←start WPRE
TTGACTGGTA TTCTTAACTA TGTTGCTCCT TTTACGCTAT GTGGATACGC TGCTTTAATG
CCTTTGTATC ATGCTATTGC TTCCCGTATG GCTTTCATTT TCTCCTCCTT GTATAAATCC
TGGTTGCTGT CTCTTTATGA GGAGTTGTGG CCCGTTGTCA GGCAACGTGG CGTGGTGTGC
ACTGTGTTTG CTGACGCAAC CCCCACTGGT TGGGGCATTG CCACCACCTG TCAGCTCCTT
TCCGGGACTT TCGCTTTCCC CCTCCCTATT GCCACGGCGG AACTCATCGC CGCCTGCCTT
GCCCGCTGCT GGACAGGGGC TCGGCTGTTG GGCACTGACA ATTCCGTGGT GTTGTCGGGG
AAGCTGACGT CCTTTCCATG GCTGCTCGCC TGTGTTGCCA CCTGGATTCT GCGCGGGACG
TCCTTCTGCT ACGTCCCTTC GGCCCTCAAT CCAGCGGACC TTCCTTCCCG CGGCCTGCTG
CCGGCTCTGC GGCCTCTTCC GCGTCTTCGC CTTCGCCCTC AGACGAGTCG GATCTCCCTT
TGGGCCGCCT CCCCGCCTGA Tgcggggatc tctagagtc gagagatcta CGGGTGGCAT
         end WPRE→↑                                    ↑←start bGH-polyA
```

FIG. 14B

```
CCCTGTGACC CCTCCCCAGT GCCTCTCCTG GCCCTGGAAG TTGCCACTCC AGTGCCCACC
AGCCTTGTCC TAATAAAATT AAGTTGCATC ATTTTGTCTG ACTAGGTGTC CTTCTATAAT
ATTATGGGGT GGAGGGGGGT GGTATGGAGC AAGGGGCAAG TTGGGAAGAC AACCTGTAGG
GCCTGCGGGG TCTATTGGGA ACCAAGCTGG AGTGCAGTGG CACAATCTTG GCTCACTGCA
ATCTCCGCCT CCTGGGTTCA AGCGATTCTC CTGCCTCAGC CTCCCGAGTT GTTGGGATTC
CAGGCATGCA TGACCAGGCT CAGCTAATTT TTGTTTTTTT GGTAGAGACG GGGTTTCACC
ATATTGGCCA GGCTGGTCTC AACTCCTAA TCTCAGGTGA TCTACCCACC TTGGCCTCCC
AAATTGCTGG GATTACAGGC GTGAACCACT GCTCCCTTCC CTGTCCTTCt gattttgtag
                                        end bGH-polyA→↑
gtaaccacgt gcggaccgag cggccgcagg aacccctagt gatggagttg gccactccct
                                 ↑←start AAV2 ITR
ctctgcgcgc tcgctcgctc actgaggccg gcgaccaaa ggtcgcccga cgcccggct
ttgcccgggc ggcctcagtg agcgagcgag cgcgcagctg cctgcagg
                                        end AAV2 ITR→↑
```

FIG. 14C

5'-ITR—CAG—HaloR—(Nav1.6 Motif)—WPRE—bGHpolyA—ITR-3'

```
←start AAV2 ITR
cctgcaggca gctgcgcgct cgctcgctca ctgaggccgc ccggcaaag cccggcgtc
ggcgaccttt tggtcgcccg gcctcagtga gcgagcgagc gcgcagagag ggagtggcca
actccatcac taggggattcc tgcggccgca cgcgtgatat CCTAGTTATT AATAGTAATC
     end AAV2 ITR→↑                                    ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                                                end CAG pomoter/enhancer→↓
CAGGGCGGGG TTCGGCTTCT GGCGTGTGAC CGGCGGCTCT AGCAGCCTCT GCTAaccatg
ttcatgcctt cttctttttc ctacagctcc tgggcaacgt gctggttatt gtgctgtctc
                                                        ↓←start HaloR
atcattttgg caaagaatta agcttgagct cgcgatccgc agcc ATG ACT GAG ACA
TTG CCA CCG GTA ACG GAA TCG GCT GTT GCG CTA CAG GCG GAG GTG ACC
CAG AGG GAG CTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG ACG ATT TTG GTG CCG GTG GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GGC GAA GAG GTA GAC GGC
GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
CTC TTT ACC GCC ATC ACC TTC GAC ATC GCG ATG TGT GTC ACC GGC CTC
GCA GCC GCG CTG ACG ACC TCT TCG CAC CTG ATG CGG TGG TTC TGG TAC
GCC ATC AGT TGT GCG TGT TTC CTC GTC GTC CTC TAC ATC CTG CTC GTC
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
```

FIG. 15A

```
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
                                                    end HaloR→↑
gaattcggag gcggaggtgg agctagc ACC GTG AGG GTG CCC ATC GCC GTG GGC
                       ↑← Start Nav1.6 Motif
GAG AGC GAC TTC GAG AAC CTG AAC ACC GAG GAC GTG AGC AGC GAG AGC
GAC CCC taactcgagt ctagacgtgg taccGATAAT CAACCTCTGG ATTACAAAAT
    ↑← end Nav1.6 Motif                  ↑←start WPRE
TTGTGAAAGA TTGACTGGTA TTCTTAACTA TGTTGCTCCT TTTACGCTAT GTGGATACGC
TGCTTTAATG CCTTTGTATC ATGCTATTGC TTCCCGTATG GCTTTCATTT TCTCCTCCTT
GTATAAATCC TGGTTGCTGT CTCTTTATGA GGAGTTGTGG CCCGTTGTCA GGCAACGTGG
CGTGGTGTGC ACTGTGTTTG CTGACGCAAC CCCCACTGGT TGGGGCATTG CCACCACCTG
TCAGCTCCTT TCCGGGACTT TCGCTTTCCC CCTGCCTATT GCCACGGCGG AACTCATCGC
CGCCTGCCTT GCCCGCTGCT GGACAGGGGC TCGGCTGTTG GGCACTGACA ATTCCGTGGT
GTTGTCGGGG AAGCTGACGT CCTTTCCATG GCTGCTCGCC TGTGTTGCCA CCTGGATTCT
GCGCGGGACG TCCTTCTGCT ACGTCCCTTC GGCCCTCAAT CCAGCGGACC TTCCTTCCGC
CGGCCTGCTG CCGGCTCTGC GGCCTCTTCC GCGTCTTCGC CTTCGCCCTC AGACGAGTCG
GATCTCCCTT TGGGCCGCCT CCCCGCCTGA Tgcggggatc ctctagagtc
                   end WPRE→↑
gagagatctA CGGGTGGCAT CCCTGTGACC CCTCCCCAGT GCCTCTCCTG GCCCTGGAAG
        ↑← start bGH-polyA
TTGCCACTCC AGTGCCCACC AGCCTTGTCC TAATAAAATT AAGTTGCATC ATTTTGTCTG
ACTAGGGTGT CTTCTATAAT ATTATGGGGT GGAGGGGGGT GGTATGGAGC AAGGGGCAAG
TTGGGAAGAC AACCTGTAGG GCCTGCGGGG TCTATTGGGA ACCAAGCTGG AGTGCAGTGG
CACAATCTTG GCTCACTGCA ATCTCCGCCT CCTGGGTTCA AGCGATTCTC CTGCCTCAGC
CTCCCGAGTT GTTGGGATTC CAGGCATGCA TGACCAGGCT CAGCTAATTT TTGTTTTTTT
GGTAGAGACG GGGTTTCACC ATATTGGCCA GGCTGGTCTC AACTCCTAA TCTCAGGTGA
TCTACCCACC TTGGCCTCCC AAATTGCTGG GATTACAGGC GTGAACCACT GCTCCCTTCC
        ↓←end bGH-polyA
CTGTCCTTCt gattttgtag gtaaccacgt gcggaccgag cggccgcagg aaccccctagt
                                                 ↑←start AAV2 ITR
gatggagttg gccactccct ctctgcgcgc tcgctcgctc actgaggccg gcgaccaaa
ggtcgcccga cgcccgggct ttgcccgggc ggcctcagtg agcgagcgag cgcgcagctg
cctgcagg
  ↑←end AAV2 ITR
```

FIG. 15B

5'-ITR—CAG—HaloR—GFP—(NLG-1 Motif)—WPRE—bGHpolyA—ITR-3'

```
←start AAV2 ITR
cctgcaggca actgcgcgct cgctcgctca ctgaggccgc ccgggcaaag cccggcgtc
ggcgaccttt ggtcgcccg gcctcagtga gcgagcgagc gcgcagagag ggagtggcca
actccatcac taggggttccc tgcggccgca cgcgtgatat CCTAGTTATT AATAGTAATC
          end AAV2 ITR→↑                     ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGGATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
```

FIG. 16A

CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGTGGACGGC TGCCTTCGGG GGGGACGGGG
CAGGGCGGGG TTCGGCTTCT GGCGTGTGAC CGGCGGCTCT AGCAGCCTCT GCTAaccatg
ttcatgcctt cttcttttc ctacagctcc tgggcaacgt gctggttatt gtgctgtctc
atcattttgg caaagaatta agcttgagct cgcgatccgc agcc ATG ACT GAG ACA
TTG CCA CCG GTA ACG GAA TCG GCT GTT GCG CTA CAG GCG GAG GTG ACC
CAG AGG GAG CTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG CTG ATT TTG GTG CCG GTC GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GGC GAA GAG GTA GAC GGC
GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
CTC TTT ACC GCC ATC ACC TTC GAC ATC GCA ATG TGT GTC GCC GGG CTC
GCA GCC GCG CTG ACG ACC TCT TCG CAC CTG ATG CGG TGG TTC TGG TAC
GCC ATC AGT TGT GCG TGT TTC CTC GTC GTC CTC TAC ATC CTG CTC GTC
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
                                                    end HaloR→↑
gaattcggag gcggaggtgg agctagc AAA GGA GAA GAA CTC TTC ACT GGA GTT
                ↑←start GFP
GGA GTT GTC CCA ATT CTT GTT GAA TTA GAT GGT GAT GTT AAC GGC CAC
AAG TTC TCT GTC AGT GGA GAG GGT GAA GGT GAT GCA ACA TAC GGA AAA
CTT ACC CTG AAG TTC ATC TGC ACT ACT GGC AAA CTG CCT GTT CCA TGG
CCA ACA CTA GTC ACT ACT CTG TGC TAT GGT GTT CAA TGC TTT TCA AGA
TAC CCG GAT CAT ATG AAA CGG CAT GAC TTT TTC AAG AGT GCC ATG CCC
GAA GGT TAT GTA CAG GAA AGG ACC ATC TTC TTC AAA GAT GAC GGC AAC
TAC AAG ACA CGT GCT GAA GTC AAG TTT GAA GGT GAT ACC CTT GTT AAT
AGA ATC GAG TTA AAA GGT ATT GAC TTC AAG GAA GAT GGC AAC ATT CTG
GGA CAC AAA TTG GAA TAC AAC TCA CAC AAT GTA TAC ATC ATG
GCA GAC AAA CAA AAG AAT GGA ATC AAA GTG AAC TTC AAG ACC CGC CAC
AAC ATT GAA GAT GGA AGC GTT CAA CTA GCA GAC CAT TAT CAA CAA AAT
ACT CCA ATT GGC GAT GGC CCT GTC CTT TTA CCA GAC AAC CAT TAC CTG
TCC ACA CAA TCT GCC CTT TCG AAA GAT CCC AAC GAA AAG AGA GAC CAC
ATG GTC CTT CTT GAG TTT GTA ACA GCT GCT GGG ATT ACA CAT GGC ATG
       end GFP →↓
GAT GAA CTG TAC AAC GTG GTT CTT CGG ACC GCC TGT CCC CCA GAT TAC
                    ↑←Start NLG-1 Motif
ACA CTA GCT ATG AGG AGG TCA CCT GAT GAT GTT CCC TTA ATG ACA CCC
AAC ACC ATT ACA ATG taactcgagt ctagacgtgg tacc GATAAT CAACCTCTGG
end NLG-1 Motif→↑                                  ↑←start WPRE
ATTACAAAAT TTGTGAAAGA TTGACTGGTA TTCTTAACTA TGTTGCTCCT TTTACGCTAT
GTGGATACGC TGCTTTAATG CCTTTGTATC ATGCTATTGC TTCCCGTATG GCTTTCATTT
TCTCCTCCTT GTATAAATCC TGGTTGCTGT CTCTTTATGA GGAGTTGTGG CCCGTTGTCA
GGCAACGTGG CGTGGTGTGC ACTGTGTTTG CTGACGCAAC CCCCACTGGT TGGGGCATTG
CCACCACCTG TCAGCTCCTT TCCGGGACTT TCGCTTTCCC CCTCCCTATT GCCACGGCGG
AACTCATCGC CGCCTGCCTT GCCCGCTGCT GGACAGGGGC TCGGCTGTTG GGCACTGACA
ATTCCGTGGT GTTGTCGGGG AAGCTGACGT CCTTTCCATG GCTGCTCGCC TGTGTTGCCA
CCTGGATTCT GCGCGGGACG TCCTTCTGCT ACGTCCCTTC GGCCCTCAAT CCAGCGGACC
TTCCTTCCCG CGGCCTGCTG CCGGCTCTGC GGCCTCTTCC GCGTCTTCGC CTTCGCCCTC
AGACGAGTCG GATCTCCCTT TGGGCCGCCT CCCCGCCTGA Tgcggggatc ctctagagtc
                                        end WPRE→↑
gagagatcta CGGGTGGCAT CCCTGTGACC CCTCCCCAGT GCCTCTCCTG GCCCTGGAAG
        ↑←start bGH-polyA
TTGCCACTCC AGTGCCCACC AGCCTTGTCC TAATAAAATT AAGTTGCATC ATTTTGTCTG
ACTAGGTGTC CTTCTATAAT ATTATGGGGT GGAGGGGGGT GGTATGGAGC AAGGGGCAAG
TTGGAAGAC AACCTGTAGG GCCTGCGGGG TCTATTGGGA ACCAAGCTGG AGTGCAGTGG
CACAATCTTG GCTCACTGCA ATCTCCGCCT CCTGGGTTCA AGCGATTCTC CTGCCTCAGC
CTCCCGAGTT GTTGGGATTC CAGGCATGCA TGACCAGGCT CAGCTAATTT TTGTTTTTTT
GGTAGAGACG GGGTTTCACC ATATTGGCCA GGCTGGTCTC CAACTCCTAA TCTCAGGTGA
TCTACCCACC TTGGCCTCCC AAATTGCTGG GATTACAGGC GTGAACCACT GCTCCCTTCC
         ↓←end bGH-polyA
CTGTCCTTct gattttgtag gtaaccacgt gcggaccgag cggccgcagg aaccccagt
                                                ↑←start AAV2 ITR
gatggagttg gccactccct ctctgcgcgc tcgctcgctc actgaggccg ggcgaccaaa
ggtcgcccga cgcccgggct ttgcccgggc ggcctcagtg agcgagcgag cgcgcagctg
cctgcagg
        ↑←end AAV2 ITR
                                    FIG. 16B 5'-ITR—CAG—HaloR—(NLG-1 Motif)—WPRE—bGHpolyA—ITR-3'

←start AAV2 ITR
cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac taggggttcc tgcggccgca cgcgtgatat CCTAGTTATT AATAGTAATC
           end AAV2 ITR→↑                          ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                                                        end CAG pomoter/enhancer→↓
CAGGGCGGGG TTCGGCTTCT GGCGTGTGAC CGGCGGCTCT AGCAGCCTCT GCTAaccatg
ttcatgcctt cttctttttc ctacagctcc tgggcaacgt gctggttatt gtgctgtctc
                                                     ↓←start HaloR
atcattttgg caaagaatta agcttgagct cgcgatccgc agcc ATG ACT GAG ACA
TTG CCA CCG GTA ACG GAA TCG GCT GTT GCG CTA CAG GCG GAG GTG ACC
CAG AGG GAG CTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG ACG ATT TTG GTG CCG GTG GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GGC GAA GAG GTA GAC GGC
GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
CTC TTT ACC GCC ATC ACC TTC GAC ATC GCG ATG TGT GTC ACC GGC CTC
GCA GCC GCG CTG ACG ACC TCT TCG CAC CTG ATG CGG TGG TTC TGG TAC
GCC ATC AGT TGT GCG TGT TTC CTC GTC GTC CTC TAC ATC CTG CTC GTC

FIG. 17A

```
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
                                                    end HaloR→↑
gaattcggag gcggaggtgg agctagc GTG GTT CTT CGG ACC GCC TGT CCC CCA
                   ↑←Start NLG-1 Motif
AAA AAG AGG CTC CTG AGC TTC AGG GAC GTG GAC TTC GAG GAG GAC AGC
GAT TAC ACA CTA GCT ATG AGG AGG TCA CCT GAT GAT GTT CCC TTA ATG
ACA CCC AAC ACC ATT ACA ATG taactcgagt ctagacgtgg taccGATAAT
      end NLG-1 Motif→↑                                    ↑←start WPRE
CAACCTCTGG ATTACAAAAT TTGTGAAAGA TTGACTGGTA TTCTTAACTA TGTTGCTCCT
TTTACGCTAT GTGGATACGC TGCTTTAATG CCTTTGTATC ATGCTATTGC TTCCCGTATG
GCTTTCATTT TCTCCTCCTT GTATAAATCC TGGTTGCTGT CTCTTTATGA GGAGTTGTGG
CCCGTTGTCA GGCAACGTGG CGTGGTGTGC ACTGTGTTTG CTGACGCAAC CCCCACTGGT
TGGGGCATTG CCACCACCTG TCAGCTCCTT TCCGGGACTT TCGCTTTCCC CCTCCCTATT
GCCACGGCGG AACTCATCGC CGCCTGCCTT GCCCGCTGCT GGACAGGGGC TCGGCTGTTG
GGCACTGACA ATTCCGTGGT GTTGTCGGGA AAGCTGACGT CCTTTCCATG GCTGCTCGCC
TGTGTTGCCA CCTGGATTCT GCGCGGGACG TCCTTCTGCT ACGTCCCTTC GGCCCTCAAT
CCAGCGGACC TTCCTTCCCG CGGCCTGCTG CCGGCTCTGC GGCCTCTTCC GCGTCTTCGC
CTTCGCCCTC AGACGAGTCG GATCTCCCTT TGGGCCGCCT CCCCGCCTGA Tgcggggatc
                                              end WPRE→↑
ctctagagtc gagagatctA CGGGTGGCAT CCCTGTGACC CCTCCCCAGT GCCTCTCCTG
         ↑←start bGH-poly
GCCCTGGAAG TTGCCACTCC AGTGCCCACC AGCCTTGTCC TAATAAAATT AAGTTGCATC
ATTTTGTCTG ACTAGGTGTC CTTCTATAAT ATTATGGGGT GGAGGGGGGT GGTATGGAGC
AAGGGGCAAG TTGGGAAGAC AACCTGTAGG GCCTGCGGGG TCTATTGGGA ACCAAGCTGG
AGTGCAGTGG CACAATCTTG GCTCACTGCA ATCTCCGCCT CCTGGGTTCA AGCGATTCTC
CTGCCTCAGC CTCCCGAGTT GTTGGGATTC CAGGCATGCA TGACCAGGCT CAGCTAATTT
TTGTTTTTTT GGTAGAGACG GGGTTTCACC ATATTGGCCA GGCTGGTCTC CAACTCCTAA
TCTCAGGTGA TCTACCCACC TTGGCCTCCC AAATTGCTGG GATTACAGGC GTGAACCACT
GCTCCCTTCC CTGTCCTTCt gattttgtag gtaaccacgt gcggaccgag cggccgcagg
    end bGH-polyA→↑                                    start AAV2 ITR→↑
gtaaccacgt gcggaccgag cggccgcagg aacccctagt gatggaagttg gccactcact
                ↑←start AAV2 ITR
ctctgcgcgc tcgctcgctc actgaggccg gcgaccaaa ggtcgcccga cgcccgggct
ttgcccgggc ggcctcagtg agcgagcgag cgcgcagctg cctgcagg
                              end AAV2 ITR→↑
```

FIG. 17B

5'-ITR—CAG—HaloR—GFP—(MLPH Motif)—WPRE—bGHpolyA—ITR-3'

←start AAV2 ITR
*cctgcaggca gctgcgcgct cgctcgctca ctgaggccgc ccgggcaaag cccgggcgtc*
*gggcgacctt tggtcgcccg gcctcagtga gcgagcgagc gcgcagagag ggagtggcca*
*actccatcac taggggttcc t*gcggccgca cgcgtgatat CCTAGTTATT AATAGTAATC
        end AAV2 ITR→↑                      ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGCATG GTCGAGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGCG GGGCGCGGGC CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGACGGC TGCCTTCGGG GGGGACGGGG
                                         end CAG pomoter/enhancer→↓
CAGGGCGGGG TCGGCTTCT GGCGTGTGAC CGGCGGCTCT AGCAGCCTCT GCTA*accatg*
*ttcatgcctt cttcttttc ctacagctcc tgggcaacgt gctggttatt gtgctgtctc*
                                              ↓←start HaloR
*atcattttgg caaagaatta agcttgagct cgcgatccgc agcc* ATG ACT GAG ACA
TTG CCA CCG GTA ACG GAA TCG GCT GTT GCG CTA CAG GCG GAG GTG ACC
CAG AGG GAG GTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG ACG ATT TTG GTG CCG GTG GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GAA GAG GTA GAC GAC
GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
CTC TTT ACC GCC ATC ACC TTC GAC ATC GCG ATG TGT GTC ACC GGC CTC
GCA GCC GCG GTG ACG TCT TCG CAC CTG ATG CGG TGG TTC TGG TAC
GCC ATC AGT TGT GCG TGT TTC CTC GTC GTC CTC TAC ATC CTC CTC GTC
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
                                                                                     end HaloR→↑
*gaattcggag gcggaggtgg agctagc* AAA GGA GAA GAA CTC TTC ACT GGA GTT
                                       ↑←start GFP
GGA GTT GTC CCA ATT CTT GTT GAA TTA GAT GGT GAT GTT AAC GGC CAC
AAG TTC TCT GTC AGT GGA GAG GGT GAA GGT GAT GCA ACA TAC GGA AAA
CTT ACC CTG AAG TTC ATC TGC ACT ACT GGC AAA CTG CCT GTT CCA TGG
CCA ACA CTA GTC ACT ACT CTG TGC TAT GGT GTT CAA TGC TTT TCA AGA
TAC CCG GAT CAT ATG AAA CGG CAT GAC TTT TTC AAG AGT GCC ATG CCC
GAA GGT TAT GTA CAG GAA AGG ACC ATC TTC TTC AAA GAT GAC GGC AAC
TAC AAG ACA CGT GCT GAA GTC AAG TTT GAA GGT GAT ACC CTT GTT AAT
AGA ATC GAG TTA AAA GGT ATT GAC TTC AAG GAA GAT GGC AAC ATT CTG
GGA CAC AAA TTG GAA TAC AAC TAT AAC TCA CAC AAT GTA TAC ATC ATG
GCA GAC AAA CAA AAG AAT GGA ATC AAA GTG AAC TTC AAG ACC CGC CAC
AAC ATT GAA GAT GGT TCT GTT CAA CTA GCA GAC CAT TAT CAA CAA AAT
ACT CCA ATT GGC GAT GGC CCT GTC CTT TTA CCA GAC AAC CAT TAC CTG
TCC ACA CAA TCT GCC CTT TCG AAA GAT CCC AAC GAA AAG AGA GAC CAC
ATG GTC CTT CTT GAG TTT GTA ACA GCT GCT GGG ATT ACA CAT GGC ATG
        end GFP →↓
GAT GAA CTG TAC AAC AGG GAC CAG CCT CTG AAC AGC AAA AAG AAA AAG
                                        ↑←Start MLPH Motif
AGG CTC CTG AGC TTC AGG GAC GTG GAC TTC GAG GAG GAC AGC GAC
                                                         end MLPH Motif→↑
*taactcgagt ctagacgtgg tacc*GATAAT CAACCTCTGG ATTACAAAAT TTGTGAAAGA
                         ↑←start WPRE
TTGACTGGTA TTCTTAACTA TGTTGCTCCT TTTACGCTAT GTGGATACGC TGCTTTAATG
CCTTTGTATC ATGCTATTGC TTCCCGTATG GCTTTCATTT TCTCCTCCTT GTATAAATCC
TGGTTGCTGT CTCTTTATGA GGAGTTGTGG CCCGTTGTCA GGCAACGTGG CGTGGTGTGC
ACTGTGTTTG CTGACGCAAC CCCCACTGGT TGGGGCATTG CCACCACCTG TCAGCTCCTT
TCCGGGACTT TCGCTTTCCC CCTCCCTATT GCCACGGCGG AACTCATCGC CGCCTGCCTT

FIG. 18A

```
GCCCGCTGCT GGACAGGGGC TCGGCTGTTG GGCACTGACA ATTCCGTGGT GTTGTCGGGG
AAGCTGACGT CCTTTCCATG GCTGCTCGCC TGTGTTGCCA CCTGGATTCT GCGCGGGACG
TCCTTCTGCT ACGTCCCTTC GGCCCTCAAT CCAGCGGACC TTCCTTCCCG CGGCCTGCTG
CCGGCTCTGC GGCCTCTTCC GCGTCTTCGC CTTCGCCCTC AGACGAGTCG GATCTCCCTT
TGGGCCGCCT CCCCGCCTGA Tgcggggatc tctagagtc gagagatct4 CGGGTGGCAT
                end WPRE→↑                         ↑←start bGH-polyA
CCCTGTGACC CCTCCCCAGT GCCTCTCCTG GCCCTGGAAG TTGCCACTCC AGTGCCCACC
AGCCTTGTCC TAATAAAATT AAGTTGCATC ATTTTGTCTG ACTAGGTGTC CTTCTATAAT
ATTATGGGGT GGAGGGGGGT GGTATGGAGC AAGGGGCAAG TTGGGAAGAC AACCTGTAGG
GCCTGCGGGG TCTATTGGGA ACCAAGCTGG AGTGCAGTGG CACAATCTTG GCTCACTGCA
ATCTCCGCCT CCTGGGTTCA AGCGATTCTC CTGCCTCAGC CTCCCGAGTT GTTGGGATTC
CAGGCATGCA TGACCAGGCT CAGCTAATTT TTGTTTTTTT GGTAGAGACG GGGTTTCACC
ATATTGGCCA GGCTGGTCTC AACTCCTAA TCTCAGGTGA TCTACCCACC TTGGCCTCCC
AAATTGCTGG GATTACAGGC GTGAACCACT GCTCCCTTCC CTGTCCTTCt gattttgtag
                                              end bGH-polyA→↑
gtaaccacgt gcggaccgag cggccgcagg aaccctagt gatggagttg gccactccct
                              ↑←start AAV2 ITR
ctctgcgcgc tcgctcgctc actgaggccg ggcgaccaaa ggtcgcccga cgcccgggct
ttgcccgggc ggcctcagtg agcgagcgag cgcgcagctg cctgcagg
                                                   end AAV2 ITR→↑
```

FIG. 18B

5'-ITR—CAG—HaloR—(MLPH Motif)—WPRE—bGHpolyA—ITR-3'

```
←start AAV2 ITR
cctgcaggca gctgcgcgct cgctcgctca ctgaggccgc ccgggcaaag cccggcgtc
ggacgacctt tggtcgcccg gcctcagtga gcgagcgagc gcgcagagag ggagtggcca
actccatcac taggggttcc tgcggccgca cgcgtgatat cCTAGTTATT AATAGTAATC
              end AAV2 ITR→↑                    ↑← start CAG pomoter/enhancer
AATTACGGGG TCATTAGTTC ATAGCCCATA TATGGAGTTC CGCGTTACAT AACTTACGGT
AAATGGCCCG CCTGGCTGAC CGCCCAACGA CCCCCGCCCA TTGACGTCAA TAATGACGTA
TGTTCCCATA GTAACGCCAA TAGGGACTTT CCATTGACGT CAATGGGTGG AGTATTTACG
GTAAACTGCC CACTTGGCAG TACATCAAGT GTATCATATG CCAAGTACGC CCCCTATTGA
CGTCAATGAC GGTAAATGGC CCGCCTGGCA TTATGCCCAG TACATGACCT TATGGGACTT
TCCTACTTGG CAGTACATCT ACGTATTAGT CATCGCTATT ACCATGGTCG AGGTGA
GCCCCACGTT CTGCTTCACT CTCCCCATCT CCCCCCCCTC CCCACCCCCA ATTTTGTATT
TATTTATTTT TTAATTATTT TGTGCAGCGA TGGGGGCGGG GGGGGGGGGG GGGCGCGCGC
CAGGCGGGGC GGGGCGGGGC GAGGGGCGGG GCGGGGCGAG GCGGAGAGGT GCGGCGGCAG
CCAATCAGAG CGGCGCGCTC CGAAAGTTTC CTTTTATGGC GAGGCGGCGG CGGCGGCGGC
CCTATAAAAA GCGAAGCGCG CGGCGGGCGG GAGTCGCTGC GACGCTGCCT TCGCCCCGTG
CCCCGCTCCG CCGCCGCCTC GCGCCGCCCG CCCCGGCTCT GACTGACCGC GTTACTCCCA
CAGGTGAGCG GGCGGGACGG CCCTTCTCCT CCGGGCTGTA ATTAGCGCTT GGTTTAATGA
CGGCTTGTTT CTTTTCTGTG GCTGCGTGAA AGCCTTGAGG GGCTCCGGGA GGGCCCTTTG
TGCGGGGGGA GCGGCTCGGG GCTGTCCGCG GGGGGACGGC TGCCTTCGGG GGGGACGGGG
                                         end CAG pomoter/enhancer→↓
CAGGGCGGGG TTCGGCTTCT GGCGTGTGAC CGGCGGCTCT AGCAGCCTCT GCTAaccatg
ttcatgcctt ctttcttttc ctacagctcc tgggcaacgt gctggttatt gtgctgtctc
                                                       ↓←start HaloR
atcattttgg caaagaatta agcttgagct cgcgatccgc agcc ATG ACT GAG ACA
TTG CCA CCG GTA ACG GAA TCG GCT GTT GCG CTA CAG GCG GAG GTG ACC
CAG AGG GAG CTG TTC GAG TTC GTT CTC AAC GAC CCC CTC CTC GCC AGT
TCG CTG TAT ATT AAT ATC GCA CTG GCA GGG CTG TCG ATA CTG CTT TTC
GTG TTC ATG ACG CGC GGA CTC GAC GAC CCA CGG GCG AAA CTC ATC GCC
GTT TCG ACG ATT TTG GTG CCG GTG GTC TCT ATC GCG AGC TAC ACC GGC
CTT GCA TCG GGG CTC ACC ATC AGC GTC CTC GAG ATG CCA GCC GGC CAC
TTC GCC GAG GGG TCC TCG GTG ATG CTC GGC GGC GAA GAG GTA GAC GGC
GTC GTG ACG ATG TGG GGC CGC TAT CTG ACG TGG GCC CTT TCG ACA CCG
ATG ATA CTG CTG GCG CTT GGG CTG CTT GCT GGC TCT AAC GCC ACG AAG
```

FIG. 19A

```
CTC TTT ACC GCC ATC ACC TTC GAC ATC GCG ATG TGT GTC ACC GGC CTC
GCA GCC GCG CTG ACG ACC TCT TCG CAC CTG ATG CGG TGG TTC TGG TAC
GCC ATC AGT TGT GCG TGT TTC CTC GTC GTC CTC TAC ATC CTG CTC GTC
GAG TGG GCA CAG GAC GCC AAG GCT GCC GGT ACT GCG GAT ATG TTC AAT
ACG CTG AAG CTG CTG ACC GTT GTC ATG TGG CTC GGC TAC CCC ATC GTG
TGG GCA CTC GGC GTT GAG GGC ATC GCC GTT CTT CCG GTC GGA GTC ACG
TCG TGG GGA TAC AGC TTC CTC GAC ATC GTC GCG AAG TAC ATC TTC GCG
TTC CTG CTG CTC AAC TAC CTC ACG TCG AAC GAG AGC GTC GTC TCC GGC
TCG ATA CTC GAC GTG CCG TCC GCG TCG GGC ACT CCC GCT GAC GAC
```
end HaloR→↑ gaattcggag gcggaggtgg agctagc AGG GAC CAG CCT CTG AAC AGC AAA AAG
↑←Start MLPH Motif
AAA AAG AGG CTC CTG AGC TTC AGG GAC GTG GAC TTC GAG GAG GAC AGC
GAC taactcgagt ctagacgtgg taccGATAAT CAACCTCTGG ATTACAAAAT
↑← end NLPH Motif         ↑←start WPRE
TTGTGAAAGA TTGACTGGTA TTCTTAACTA TGTTGCTCCT TTTACGCTAT GTGGATACGC
TGCTTTAATG CCTTTGTATC ATGCTATTGC TTCCCGTATG GCTTTCATTT TCTCCTCCTT
GTATAAATCC TGGTTGCTGT CTCTTTATGA GGAGTTGTGG CCCGTTGTCA GGCAACGTGG
CGTGGTGTGC ACTGTGTTTG CTGACGCAAC CCCCACTGGT TGGGGCATTG CCACCACCTG
TCAGCTCCTT TCCGGGACTT TCGCTTTCCC CCTCCCTATT GCCACGGCGG AACTCATCGC
CGCCTGCCTT GCCCGCTGCT GGACAGGGGC TCGGCTGTTG GCACTGACA ATTCCGTGGT
GTTGTCGGGG AAGCTGACGT CCTTTCCATG GCTGCTCGCC TGTGTTGCCA CCTGGATTCT
GCGCGGGACG TCCTTCTGCT ACGTCCCTTC GGCCCTCAAT CCAGCGGACC TTCCTTCCCG
CGGCCTGCTG CCGGCTCTGC GGCCTCTTCC GCGTCTTCGC CTTCGCCCTC AGACGAGTCG
GATCTCCCTT TGGGCCGCCT CCCCGCCTGA Tgcggggatc tctagagtc
                        end WPRE→↑
gagagatctA CGGGTGGCAT CCCTGTGACC CCTCCCCAGT GCCTCTCCTG GCCCTGGAAG
↑←start bGH-polyA
TTGCCACTCC AGTGCCCACC AGCCTTGTCC TAATAAAATT AAGTTGCATC ATTTTGTCTG
ACTAGGTGTC CTTCTATAAT ATTATGGGGT GGAGGGGGGT GGTATGGAGC AAGGGGCAAG
TTGGGAAGAC AACCTGTAGG GCCTGCGGGG TCTATTGGGA ACCAAGCTGG AGTGCAGTGG
CACAATCTTG GCTCACTGCA ATCTCCGCCT CCTGGGTTCA AGCGATTCTC CTGCCTCAGC
CTCCCGAGTT GTTGGGATTC CAGGCATGCA TGACCAGGCT CAGCTAATTT TTGTTTTTTT
GGTAGAGACG GGGTTTCACC ATATTGGCCA GGCTGGTCTC AACTCCTAA TCTCAGGTGA
TCTACCCACC TTGGCCTCCC AAATTGCTGG GATTACAGGC GTGAACCACT GCTCCCTTCC
↓← end bGH-polyA
CTGTCCTTCt gattttgtag gtaaccacgt gcggaccgag cggccgcagg aacccctagt
                                            ↑←start AAV2 ITR
gatggagttg gccactccct ctctgcgcgc tcgctcgctc actgaggccg ggcgaccaaa
ggtcgcccga cgcccgggct tgccgggc ggcctcagtg agcgagcgag cgcgcagctg
cctgcagg
↑←end AAV2 ITR

FIG. 19B

SEQUENCE LISTING

<160> NUMBER OF SEQ ID NOS: 46

<210> SEQ ID NO 1
<211> LENGTH: 195
<212> TYPE: DNA
<213> ORGANISM: Artificial Sequence
<220> FEATURE:
<223> OTHER INFORMATION: Kv2.1 Cytoplasmic C-terminus sorting motif

<400> SEQUENCE: 1

```
cagtctcagc ccatcctgaa cactaaggag atggcccctc agagtaaacc ccctgaggaa      60
ctggaaatga gctccatgcc atctccagtg gctcctctgc cagctaggac cgagggcgtg     120
attgacatga gaagcatgtc tagtatcgat agcttcattt cctgcgccac cgacttcccc     180
gaagctacaa ggttt                                                      195
```

<210> SEQ ID NO 2
<211> LENGTH: 65
<212> TYPE: PRT
<213> ORGANISM: Artificial Sequence
<220> FEATURE:
<223> OTHER INFORMATION: Kv2.1 Cytoplasmic C-terminus sorting motif

<400> SEQUENCE: 2

```
Gln Ser Gln Pro Ile Leu Asn Thr Lys Glu Met Ala Pro Gln Ser Lys
1               5                  10                  15

Pro Pro Glu Glu Leu Glu Met Ser Ser Met Pro Ser Pro Val Ala Pro
            20                  25                  30

Leu Pro Ala Arg Thr Glu Gly Val Ile Asp Met Arg Ser Met Ser Ser
        35                  40                  45

Ile Asp Ser Phe Ile Ser Cys Ala Thr Asp Phe Pro Glu Ala Thr Arg
    50                  55                  60

Phe
65
```

<210> SEQ ID NO 3
<211> LENGTH: 81
<212> TYPE: DNA
<213> ORGANISM: Artificial Sequence
<220> FEATURE:
<223> OTHER INFORMATION: Nav1.6 Ankyrin binding domain sorting motif

<400> SEQUENCE: 3

```
accgtgaggg tgcccatcgc cgtgggcgag agcgacttcg agaacctgaa caccgaggac      60
gtgagcagcg agagcgaccc c                                                81
```

<210> SEQ ID NO 4
<211> LENGTH: 27
<212> TYPE: PRT
<213> ORGANISM: Artificial Sequence
<220> FEATURE:
<223> OTHER INFORMATION: Nav1.6 Ankyrin binding domain sorting motif

<400> SEQUENCE: 4

```
Thr Val Arg Val Pro Ile Ala Val Gly Glu Ser Asp Phe Glu Asn Leu
1               5                  10                  15

Asn Thr Glu Asp Val Ser Ser Glu Ser Asp Pro
            20                  25
```

<210> SEQ ID NO 5
<211> LENGTH: 96
<212> TYPE: DNA

```
<213> ORGANISM: Artificial Sequence
<220> FEATURE:
<223> OTHER INFORMATION: NLG-1 Cytoplasmic C-terminal sorting motif

<400> SEQUENCE: 5
gtggtgctga ggactgcctg cccccctgac tacaccctgg ctatgaggag aagcccagac       60
gatgtgcccc tgatgacccc caacaccatc acaatg                                 96

<210> SEQ ID NO 6
<211> LENGTH: 32
<212> TYPE: PRT
<213> ORGANISM: Artificial Sequence
<220> FEATURE:
<223> OTHER INFORMATION: NLG-1 Cytoplasmic C-terminal sorting motif

<400> SEQUENCE: 6

Val Val Leu Arg Thr Ala Cys Pro Pro Asp Tyr Thr Leu Ala Met Arg
1               5                   10                  15

Arg Ser Pro Asp Asp Val Pro Leu Met Thr Pro Asn Thr Ile Thr Met
            20                  25                  30

<210> SEQ ID NO 7
<211> LENGTH: 78
<212> TYPE: DNA
<213> ORGANISM: Artificial Sequence
<220> FEATURE:
<223> OTHER INFORMATION: MLPH Myosin binding domain sorting motif

<400> SEQUENCE: 7
agggaccagc tctgaacag caaaaagaaa aagaggctcc tgagcttcag ggacgtggac        60
ttcgaggagg acagcgac                                                     78

<210> SEQ ID NO 8
<211> LENGTH: 26
<212> TYPE: PRT
<213> ORGANISM: Artificial Sequence
<220> FEATURE:
<223> OTHER INFORMATION: MLPH Myosin binding domain sorting motif

<400> SEQUENCE: 8

Arg Asp Gln Pro Leu Asn Ser Lys Lys Lys Arg Leu Leu Ser Phe
1               5                   10                  15

Arg Asp Val Asp Phe Glu Glu Asp Ser Asp
            20                  25

<210> SEQ ID NO 9
<211> LENGTH: 141
<212> TYPE: DNA
<213> ORGANISM: Artificial Sequence
<220> FEATURE:
<223> OTHER INFORMATION: nAchR Tyrosine-Dileucine sorting motif

<400> SEQUENCE: 9
ggcgaggaca aggtgcggcc cgcctgtcag cacaagcctc ggcggtgcag cctggccagc        60
gtggagctga gcgccggcgc cggcccaccc accagcaacg gcaacctgct gtacatcggc       120
ttcagaggcc tggagggcat g                                                141

<210> SEQ ID NO 10
<211> LENGTH: 47
<212> TYPE: PRT
<213> ORGANISM: Artificial Sequence
<220> FEATURE:
<223> OTHER INFORMATION: nAchR Tyrosine-Dileucine sorting motif
```

<400> SEQUENCE: 10

Gly Glu Asp Lys Val Arg Pro Ala Cys Gln His Lys Pro Arg Arg Cys
1               5                   10                  15

Ala Leu Ala Ser Val Glu Leu Ser Ala Gly Ala Gly Pro Pro Thr Ser
            20                  25                  30

Asn Gly Asn Leu Leu Tyr Ile Gly Phe Arg Gly Leu Glu Gly Met
        35                  40                  45

<210> SEQ ID NO 11
<211> LENGTH: 48
<212> TYPE: DNA
<213> ORGANISM: Artificial Sequence
<220> FEATURE:
<223> OTHER INFORMATION: Kv4.2 Dileucine sorting motif

<400> SEQUENCE: 11
ttcgagcagc agcaccacca cctgctgcac tgcctggaga agaccacc        48

<210> SEQ ID NO 12
<211> LENGTH: 16
<212> TYPE: PRT
<213> ORGANISM: Artificial Sequence
<220> FEATURE:
<223> OTHER INFORMATION: Kv4.2 Dileucine sorting motif

<400> SEQUENCE: 12

Phe Glu Gln Gln His His His Leu Leu His Cys Leu Glu Lys Thr Thr
1               5                   10                  15

<210> SEQ ID NO 13
<211> LENGTH: 192
<212> TYPE: DNA
<213> ORGANISM: Artificial Sequence
<220> FEATURE:
<223> OTHER INFORMATION: TLCN Phenylalanine-based sorting motif

<400> SEQUENCE: 13
cagagcacag cctgcaaaaa gggcgagtac aacgtgcagg aagctgagag ctctggcgaa        60
gccgtgtgtc tgaacggcgc cggaggcggt gccggcggag ctgccggcgc tgagggtggc       120
cctgaggccg ctggaggtgc cgctgagagc cccgctgagg gcgaagtctt tgccatccag       180
ctgacatctg ct                                                           192

<210> SEQ ID NO 14
<211> LENGTH: 64
<212> TYPE: PRT
<213> ORGANISM: Artificial Sequence
<220> FEATURE:
<223> OTHER INFORMATION: TLCN Phenylalanine-based sorting motif

<400> SEQUENCE: 14

Gln Ser Thr Ala Cys Lys Lys Gly Glu Tyr Asn Val Gln Glu Ala Glu
1               5                   10                  15

Ser Ser Gly Glu Ala Val Cys Leu Asn Gly Ala Gly Gly Gly Ala Gly
            20                  25                  30

Gly Ala Ala Gly Ala Glu Gly Gly Pro Glu Ala Ala Gly Gly Ala Ala
        35                  40                  45

Glu Ser Pro Ala Glu Gly Glu Val Phe Ala Ile Gln Leu Thr Ser Ala
    50                  55                  60

<210> SEQ ID NO 15

```
<211> LENGTH: 117
<212> TYPE: DNA
<213> ORGANISM: Artificial Sequence
<220> FEATURE:
<223> OTHER INFORMATION: AMPAR Cytoplasmic C-terminal sorting motif

<400> SEQUENCE: 15
gagttctgct acaagagcag gtccgaatct aagagaatga aaggcttttg tctgatcccc      60
cagcagagca tcaacgaggc cattcggacc agtacactgc ctcgcaatag cggagct         117

<210> SEQ ID NO 16
<211> LENGTH: 39
<212> TYPE: PRT
<213> ORGANISM: Artificial Sequence
<220> FEATURE:
<223> OTHER INFORMATION: AMPAR Cytoplasmic C-terminal sorting motif

<400> SEQUENCE: 16

Glu Phe Cys Tyr Lys Ser Arg Ser Glu Ser Lys Arg Met Lys Gly Phe
1               5                   10                  15

Cys Leu Ile Pro Gln Gln Ser Ile Asn Glu Ala Ile Arg Thr Ser Thr
            20                  25                  30

Leu Pro Arg Asn Ser Gly Ala
        35

<210> SEQ ID NO 17
<211> LENGTH: 141
<212> TYPE: DNA
<213> ORGANISM: Artificial Sequence
<220> FEATURE:
<223> OTHER INFORMATION: AAV2  5' ITR

<400> SEQUENCE: 17
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc t                                                141

<210> SEQ ID NO 18
<211> LENGTH: 141
<212> TYPE: DNA
<213> ORGANISM: Artificial Sequence
<220> FEATURE:
<223> OTHER INFORMATION: AAV2  3' ITR

<400> SEQUENCE: 18
aggaacccct agtgatggag ttggccactc cctctctgcg cgctcgctcg ctcactgagg      60
ccgggcgacc aaaggtcgcc cgacgcccgg gctttgcccg gcggcctcag tgagcgagc      120 gagcgcgcag ctgcctgcag g                                                141

<210> SEQ ID NO 19
<211> LENGTH: 1213
<212> TYPE: DNA
<213> ORGANISM: Homo sapiens
<220> FEATURE:
<221> NAME/KEY: misc_feature
<222> LOCATION: (1)..(1213)
<223> OTHER INFORMATION: Homo sapiens rhodopsin, mRNA (cDNA clone
      MGC:138309 IMAGE:8327572), complete cds

<400> SEQUENCE: 19
ccagctggag ccctgagtgg ctgagctcag gccttcgcag cattcttggg tgggagcagc      60
cacgggtcag ccacaagggc cacagccatg aatggcacag aaggccctaa cttctacgtg     120
```

```
cccttctcca atgcgacggg tgtggtacgc agccccttcg agtacccaca gtactacctg      180
gctgagccat ggcagttctc catgctggcc gcctacatgt ttctgctgat cgtgctgggc      240
ttccccatca acttcctcac gctctacgtc accgtccagc acaagaagct gcgcacgcct      300
ctcaactaca tcctgctcaa cctagccgtg gctgacctct tcatggtcct aggtggcttc      360
accagcaccc tctacacctc tctgcatgga tacttcgtct tcgggcccac aggatgcaat      420
ttggagggct tctttgccac cctgggcggt gaaattgccc tgtggtcctt ggtggtcctg      480
gccatcgagc ggtacgtggt ggtgtgtaag cccatgagca acttccgctt cggggagaac      540
catgccatca tgggcgttgc cttcacctgg gtcatggcgc tggcctgcgc cgcaccccca      600
ctcgccggct ggtccaggta catccccgag ggcctgcagt gctcgtgtgg aatcgactac      660
tacacgctca gccggaggt caacaacgag tcttttgtca tctacatgtt cgtggtccac      720
ttcaccatcc ccatgattat catctttttc tgctatgggc agctcgtctt caccgtcaag      780
gaggccgctg cccagcagca ggagtcagcc accacacaga aggcagagaa ggaggtcacc      840
cgcatggtca tcatcatggt catcgctttc ctgatctgct gggtgcccta cgccagcgtg      900
gcattctaca tcttcaccca ccagggctcc aacttcggtc ccatcttcat gaccatccca      960
gcgttctttg ccaagagcgc cgccatctac aaccctgtca tctatatcat gatgaacaag     1020
cagttccgga actgcatgct caccaccatc tgctgcggca gaacccact gggtgacgat     1080
gaggcctctg ctaccgtgtc aagacggag acgagccagg tggccccggc ctaagacctg     1140
cctaggactc tgtggccgac tataggcgtc tcccatcccc tacaccttcc cccagccaca     1200
gccatcccac cag                                                         1213
```

<210> SEQ ID NO 20
<211> LENGTH: 348
<212> TYPE: PRT
<213> ORGANISM: Homo sapiens
<220> FEATURE:
<221> NAME/KEY: MISC_FEATURE
<222> LOCATION: (1)..(348)
<223> OTHER INFORMATION: Rhodopsin [Homo sapiens]
    GenBank: AAI12105.1

<400> SEQUENCE: 20

```
Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140
```

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
            165                 170                 175

Arg Tyr Ile Pro Glu Gly Leu Gln Cys Ser Cys Gly Ile Asp Tyr Tyr
        180                 185                 190

Thr Leu Lys Pro Glu Val Asn Asn Glu Ser Phe Val Ile Tyr Met Phe
    195                 200                 205

Val Val His Phe Thr Ile Pro Met Ile Ile Ile Phe Phe Cys Tyr Gly
210                 215                 220

Gln Leu Val Phe Thr Val Lys Glu Ala Ala Gln Gln Gln Glu Ser
225                 230                 235                 240

Ala Thr Thr Gln Lys Ala Glu Lys Glu Val Thr Arg Met Val Ile Ile
            245                 250                 255

Met Val Ile Ala Phe Leu Ile Cys Trp Val Pro Tyr Ala Ser Val Ala
            260                 265                 270

Phe Tyr Ile Phe Thr His Gln Gly Ser Asn Phe Gly Pro Ile Phe Met
        275                 280                 285

Thr Ile Pro Ala Phe Phe Ala Lys Ser Ala Ala Ile Tyr Asn Pro Val
    290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
            325                 330                 335

Val Ser Lys Thr Glu Thr Ser Gln Val Ala Pro Ala
            340                 345

<210> SEQ ID NO 21
<211> LENGTH: 945
<212> TYPE: DNA
<213> ORGANISM: Artificial Sequence
<220> FEATURE:
<223> OTHER INFORMATION: ChR2

<400> SEQUENCE: 21
atggattatg gaggcgccct gagtgccgtt gggcgcgagc tgctatttgt aacgaaccca      60
gtagtcgtca atggctctgt acttgtgcct gaggaccagt gttactgcgc gggctggatt     120
gagtcgcgtg gcacaaacgg tgcccaaacg cgtcgaacg tgctgcaatg gcttgctgct     180
ggcttctcca tcctactgct tatgttttac gcctaccaaa catggaagtc aacctgcggc     240
tgggaggaga tctatgtgtg cgctatcgag atggtcaagg tgattcttga gttcttcttc     300
gagtttaaga cccgtccat gctgtatcta gccacaggcc accgcgtcca gtggttgcgt     360
tacgccgagt ggcttctcac ctgcccggtc attctcattc acctgtcaaa cctgacgggc     420
ttgtccaacg actacagcag gcgcactatg ggtctgcttg tgtctgatat tggcacaatt     480
gtgtggggcg ccacttccgc tatggccacc ggatacgtca aggtcatctt cttctgcctg     540
ggtctgtgtt atggtgctaa cacgttcttt cacgctgcca aggcctacat cgagggttac     600
cataccgtgc cgaagggccg tgtgcgccag gtggtgactg gcatggcttg gctcttcttc     660
gtatcatggg gtatgttccc catcctgttc atcctcggcc ccgagggctt cggcgtcctg     720
agcgtgtacg gctccaccgt cggccacacc atcattgacc tgatgtcgaa gaactgctgg     780
ggtctgctcg gccactacct gcgcgtgctg atccacgagc atatcctcat ccacggcgac     840
attcgcaaga ccaccaaatt gaacattggt ggcactgaga ttgaggtcga cgcgctggtg     900
gaggacgagg ccgaggctgg cgcggtcaac aagggcaccg gcaag    945

```
<210> SEQ ID NO 22
<211> LENGTH: 315
<212> TYPE: PRT
<213> ORGANISM: Artificial Sequence
<220> FEATURE:
<223> OTHER INFORMATION: ChR2
<220> FEATURE:
<221> NAME/KEY: MISC_FEATURE
<222> LOCATION: (1)..(315)
<223> OTHER INFORMATION: ChR2

<400> SEQUENCE: 22
```

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
        20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys
305                 310                 315

```
<210> SEQ ID NO 23
<211> LENGTH: 873
```

<212> TYPE: DNA
<213> ORGANISM: Artificial Sequence
<220> FEATURE:
<223> OTHER INFORMATION: HaloR

<400> SEQUENCE: 23

| | | | | |
|---|---|---|---|---|
| atgactgaga cattgccacc ggtaacggaa tcggctgttg cgctacaggc ggaggtgacc | | | | 60 |
| cagagggagc tgttcgagtt cgttctcaac gaccccctcc tcgccagttc gctgtatatt | | | | 120 |
| aatatcgcac tggcagggct gtcgatactg cttttcgtgt tcatgacgcg cggactcgac | | | | 180 |
| gacccacggg cgaaactcat cgccgtttcg acgatttggg tgccggtggt ctctatcgcg | | | | 240 |
| agctacaccg gccttgcatc ggggctcacc atcagcgtcc tcgagatgcc agccggccac | | | | 300 |
| ttcgccgagg ggtcctcggt gatgctcggc ggcgaagagg tagacggcgt cgtgacgatg | | | | 360 |
| tggggccgct atctgacgtg ggcccttttcg acaccgatga tactgctggc gcttgggctg | | | | 420 |
| cttgctggct ctaacgccac gaagctctttt accgccatca ccttcgacat cgcgatgtgt | | | | 480 |
| gtcaccggcc tcgcagccgc gctgacgacc tcttcgcacc tgatgcggtg gttctggtac | | | | 540 |
| gccatcagtt gtgcgtgttt cctcgtcgtc ctctacatcc tgctcgtcga gtgggcacag | | | | 600 |
| gacgccaagg ctgccggtac tgcggatatg ttcaatacgc tgaagctgct gaccgttgtc | | | | 660 |
| atgtggctcg gctaccccat cgtgtgggca ctcggcgttg agggcatcgc cgttcttccg | | | | 720 |
| gtcggagtca cgtcgtgggg atacagcttc ctcgacatcg tcgcgaagta catcttcgcg | | | | 780 |
| ttcctgctgc tcaactacct cacgtcgaac gagagcgtcg tctccggctc gatactcgac | | | | 840 |
| gtgccgtccg cgtcgggcac tcccgctgac gac | | | | 873 |

<210> SEQ ID NO 24
<211> LENGTH: 291
<212> TYPE: PRT
<213> ORGANISM: Artificial Sequence
<220> FEATURE:
<223> OTHER INFORMATION: HaloR
<220> FEATURE:
<221> NAME/KEY: MISC_FEATURE
<222> LOCATION: (1)..(291)
<223> OTHER INFORMATION: HaloR

<400> SEQUENCE: 24

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys

```
                145                 150                 155                 160
Val Thr Gly Leu Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
                195                 200                 205

Asp Met Phe Asn Thr Leu Lys Leu Leu Thr Val Val Met Trp Leu Gly
            210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
                275                 280                 285

Ala Asp Asp
    290

<210> SEQ ID NO 25
<211> LENGTH: 708
<212> TYPE: DNA
<213> ORGANISM: Artificial Sequence
<220> FEATURE:
<223> OTHER INFORMATION: GFP

<400> SEQUENCE: 25
aaaggagaag aactcttcac tggagttgtc ccaattcttg ttgaattaga tggtgatgtt      60
aacggccaca gttctctgt cagtggagag ggtgaaggtg atgcaacata cggaaaactt     120
accctgaagt tcatctgcac tactggcaaa ctgcctgtc catggccaac actagtcact     180
actctgtgct atggtgttca atgcttttca agatacccgg atcatgaa acggcatgac     240 tttttcaaga gtgccatgcc cgaaggttat gtacaggaaa ggaccatctt cttcaaagat     300
gacggcaact acaagacacg tgctgaagtc aagtttgaag tgatacct tgttaataga     360 atcgagttaa aggtattga cttcaaggaa gatggcaaca ttctgggaca caaattggaa     420
tacaactata actcacacaa tgtatacatc atggcagaca acaaaagaa tggaatcaaa     480 gtgaacttca gacccgcca acattgaa gatggaagcg ttcaactagc agaccattat     540
caacaaaata ctccaattgg cgatggccct gtcctttac cagacaacca ttacctgtcc     600
acacaatctg cccttttcgaa agatcccaac gaaagagag accacatggt ccttcttgag     660
tttgtaacag ctgctgggat tacacatggc atggatgaac tgtacaac                708

<210> SEQ ID NO 26
<211> LENGTH: 972
<212> TYPE: DNA
<213> ORGANISM: Artificial Sequence
<220> FEATURE:
<223> OTHER INFORMATION: CAG promoter

<400> SEQUENCE: 26
ctagttatta atagtaatca attacggggt cattagttca tagcccatat atggagttcc      60
gcgttacata acttacggta aatggcccgc ctggctgacc gcccaacgac ccccgcccat     120
tgacgtcaat aatgacgtat gttcccatag taacgccaat agggactttc cattgacgtc     180
```

| | |
|---|---|
| aatgggtgga gtatttacgg taaactgccc acttggcagt acatcaagtg tatcatatgc | 240 |
| caagtacgcc ccctattgac gtcaatgacg gtaaatggcc cgcctggcat tatgcccagt | 300 |
| acatgacctt atgggacttt cctacttggc agtacatcta cgtattagtc atcgctatta | 360 |
| ccatgcatgg tcgaggtgag ccccacgttc tgcttcactc tccccatctc ccccccctcc | 420 |
| ccacccccaa ttttgtattt atttattttt taattatttt gtgcagcgat gggggcgggg | 480 |
| ggggggggggg ggcgcgcgcc aggcggggcg gggcggggcg aggggcgggg cggggcgagg | 540 |
| cggagaggtg cggcggcagc caatcagagc ggcgcgctcc gaaagtttcc ttttatggcg | 600 |
| aggcggcggc ggcggcggcc ctataaaaag cgaagcgcgc ggcgggcggg agtcgctgcg | 660 |
| acgctgcctt cgccccgtgc cccgctccgc cgccgcctcg cgccgcccgc cccggctctg | 720 |
| actgaccgcg ttactcccac aggtgagcgg gcgggacggc ccttctcctc cgggctgtaa | 780 |
| ttagcgcttg gtttaatgac ggcttgtttc ttttctgtgg ctgcgtgaaa gccttgaggg | 840 |
| gctccgggag ggcccttgt gcgggggag cggctcgggg ctgtccgcgg ggacggct | 900 |
| gccttcgggg gggacgggc agggcgggt tcggcttctg gcgtgtgacc ggcggctcta | 960 |
| gcagcctctg ct | 972 |

<210> SEQ ID NO 27
<211> LENGTH: 597
<212> TYPE: DNA
<213> ORGANISM: Artificial Sequence
<220> FEATURE:
<223> OTHER INFORMATION: Posttranscriptional regulatory element WPRE

<400> SEQUENCE: 27

| | |
|---|---|
| gataatcaac ctctggatta caaaatttgt gaaagattga ctggtattct taactatgtt | 60 |
| gctccttta cgctatgtgg atacgctgct ttaatgcctt tgtatcatgc tattgcttcc | 120 |
| cgtatggctt tcattttctc ctccttgtat aaatcctggt tgctgtctct ttatgaggag | 180 |
| ttgtggcccg ttgtcaggca acgtggcgtg gtgtgcactg tgtttgctga cgcaaccccc | 240 |
| actggttggg gcattgccac cacctgtcag ctcctttccg ggactttcgc tttccccctc | 300 |
| cctattgcca cggcggaact catcgccgcc tgccttgccc gctgctggac aggggctcgg | 360 |
| ctgttgggca ctgacaattc cgtggtgttg tcggggaagc tgacgtcctt tccatggctg | 420 |
| ctcgcctgtg ttgccacctg gattctgcgc gggacgtcct tctgctacgt cccttcggcc | 480 |
| ctcaatccag cggaccttcc ttcccgcggc ctgctgccgg ctctgcggcc tcttccgcgt | 540 |
| cttcgccttc gccctcagac gagtcggatc tccctttggg ccgcctcccc gcctgat | 597 |

<210> SEQ ID NO 28
<211> LENGTH: 479
<212> TYPE: DNA
<213> ORGANISM: Artificial Sequence
<220> FEATURE:
<223> OTHER INFORMATION: Polyadenylation sequence

<400> SEQUENCE: 28

| | |
|---|---|
| acgggtggca tccctgtgac ccctccccag tgcctctcct ggccctggaa gttgccactc | 60 |
| cagtgcccac cagccttgtc ctaataaaat aagttgcat cattttgtct gactaggtgt | 120 |
| ccttctataa tattatgggg tggaggggggg tggtatggag caaggggcaa gttgggaaga | 180 |
| caacctgtag ggcctgcggg gtctattggg aaccaagctg gagtgcagtg gcacaatctt | 240 |
| ggctcactgc aatctccgcc tcctgggttc aagcgattct cctgcctcag cctcccgagt | 300 |
| tgttgggatt ccaggcatgc atgaccaggc tcagctaatt tttgttttt tggtagagac | 360 |

```
ggggtttcac catattggcc aggctggtct ccaactccta atctcaggtg atctacccac    420
cttggcctcc caaattgctg ggattacagg cgtgaaccac tgctcccttc cctgtccttt    479
```

<210> SEQ ID NO 29
<211> LENGTH: 4232
<212> TYPE: DNA
<213> ORGANISM: Artificial Sequence
<220> FEATURE:
<223> OTHER INFORMATION: 5' -ITR-CAG-ChR2-GFP-WPRE-bGHpolyA-ITR- 3'

<400> SEQUENCE: 29

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc cccctattga    420
cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct ccccccctc ccacccccca attttgtatt    600
tatttatttt ttaattattt tgtgcagcga tgggggcggg ggggggggg gggcgcgcgc    660 caggcggggc ggggcggggc gaggggcggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg cccggctct gactgaccgc gttactccca    900
caggtgagcg gcgggacgg cccttctcct ccgggctgta attagcgctt ggtttaatga    960
cggcttgttt cttttctgtg gctgcgtgaa agccttgagg ggctccggga gggccctttg   1020 tgcggggga gcggctcggg gctgtccgcg ggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatggat tatggaggcg   1260
ccctgagtgc cgttgggcgc gagctgctat ttgtaacgaa cccagtagtc gtcaatggct   1320
ctgtacttgt gcctgaggac cagtgttact gcgcgggctg gattgagtcg cgtggcacaa   1380
acggtgccca acggcgtcg aacgtgctgc aatggcttgc tgctggcttc tccatcctac   1440
tgcttatgtt ttacgcctac caaacatgga agtcaacctg cggctgggag gagatctatg   1500
tgtgcgctat cgagatggtc aaggtgattc ttgagttctt cttcgagttt aagaacccgt   1560
ccatgctgta tctagccaca ggccaccgcg tccagtggtt gcgttacgcc gagtggcttc   1620
tcacctgccc ggtcattctc attcacctgt caaacctgac gggcttgtcc aacgactaca   1680
gcaggcgcac tatgggtctg cttgtgtctg atattggcac aattgtgtgg ggcgccactt   1740
ccgctatggc caccggatac gtcaaggtca tcttcttctg cctgggtctg tgttatggtg   1800
ctaacacgtt ctttcacgct gccaaggcct acatcgaggg ttaccatacc gtgccgaagg   1860
gccggtgtcg ccaggtggtg actggcatgg cttggctctt cttcgtatca tggggtatgt   1920
```

```
tccccatcct gttcatcctc ggccccgagg gcttcggcgt cctgagcgtg tacggctcca   1980
ccgtcggcca caccatcatt gacctgatgt cgaagaactg ctggggtctg ctcggccact   2040
acctgcgcgt gctgatccac gagcatatcc tcatccacgg cgacattcgc aagaccacca   2100
aattgaacat tggtggcact gagattgagg tcgagacgct ggtggaggac gaggccgagg   2160
ctggcgcggt caacaagggc accggcaagg aattcggagg cggaggtgga gctagcaaag   2220
gagaagaact cttcactgga gttgtcccaa ttcttgttga attagatggt gatgttaacg   2280
gccacaagtt ctctgtcagt ggagagggtg aaggtgatgc aacatacgga aaacttaccc   2340
tgaagttcat ctgcactact ggcaaactgc ctgttccatg gccaacacta gtcactactc   2400
tgtgctatgg tgttcaatgc ttttcaagat acccggatca tatgaaacgg catgactttt   2460
tcaagagtgc catgcccgaa ggttatgtac aggaaaggac catcttcttc aaagatgacg   2520
gcaactacaa gacacgtgct gaagtcaagt ttgaaggtga taccettgtt aatagaatcg   2580
agttaaaagg tattgacttc aaggaagatg gcaacattct gggacacaaa ttggaataca   2640
actataactc acacaatgta tacatcatgg cagacaaaca aaagaatgga atcaaagtga   2700
acttcaagac ccgccacaac attgaagatg gaagcgttca actagcagac cattatcaac   2760
aaaatactcc aattggcgat ggccctgtcc ttttaccaga caaccattac ctgtccacac   2820
aatctgccct ttcgaaagat cccaacgaaa agagagacca catggtcctt cttgagtttg   2880
taacagctgc tgggattaca catggcatgg atgaactgta caactaactc gagtctagac   2940
gtggtaccga taatcaacct ctggattaca aaatttgtga agattgact ggtattctta   3000
actatgttgc tccttttacg ctatgtggat acgctgcttt aatgcctttg tatcatgcta   3060
ttgcttcccg tatggctttc attttctcct ccttgtataa atcctggttg ctgtctcttt   3120
atgaggagtt gtggcccgtt gtcaggcaac gtggcgtggt gtgcactgtg tttgctgacg   3180
caacccccac tggttgggc attgccacca cctgtcagct ccttcccggg actttcgctt   3240
tccccctccc tattgccacg gcggaactca tcgccgcctg ccttgcccgc tgctggacag   3300
gggctcggct gttgggcact gacaattccg tggtgttgtc ggggaagctg acgtcctttc   3360
catggctgct cgcctgtgtt gccacctgga ttctgcgcgg gacgtccttc tgctacgtcc   3420
cttcggccct caatccagcg gaccttcctt cccgcggcct gctgccggct ctgcggcctc   3480
ttccgcgtct tcgccttcgc cctcagacga gtcggatctc cctttgggcc gcctccccgc   3540
ctgatgcggg gatcctctag agtcgagaga tctacgggtg gcatccctgt gacccctccc   3600
cagtgcctct cctggccctg gaagttgcca ctccagtgcc caccagcctt gtcctaataa   3660
aattaagttg catcatttg tctgactagg tgtccttcta taatattatg gggtggaggg   3720
gggtggtatg gagcaagggg caagttggga agacaacctg tagggcctgc ggggtctatt   3780
gggaaccaag ctggagtgca gtggcacaat cttggctcac tgcaatctcc gcctcctggg   3840
ttcaagcgat tctcctgcct cagcctcccg agttgttggg attccaggca tgcatgacca   3900
ggctcagcta ttttgttt ttttggtaga gacggggttt caccatattg gccaggctgg   3960
tctccaactc ctaatctcag gtgatctacc caccttggcc tcccaaattg ctgggattac   4020
aggcgtgaac cactgctccc ttccctgtcc ttctgatttt gtaggtaacc acgtgcggac   4080
cgagcggccg caggaacccc tagtgatgga gttggccact ccctctctgc gcgctcgctc   4140
gctcactgag gccgggcgac caaaggtcgc ccgacgcccg ggctttgccc gggcggcctc   4200
agtgagcgag cgagcgcgca gctgcctgca gg                                 4232
```

<210> SEQ ID NO 30
<211> LENGTH: 3488
<212> TYPE: DNA
<213> ORGANISM: Artificial Sequence
<220> FEATURE:
<223> OTHER INFORMATION: 5'-ITR-CAG-ChR2-WPRE-bGHpolyA-ITR- 3'

<400> SEQUENCE: 30

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggttcc | tgcggccgca | cgcgtgatat | cctagttatt | aatagtaatc | 180 |
| aattacgggg | tcattagttc | atagcccata | tatggagttc | cgcgttacat | aacttacggt | 240 |
| aaatggcccg | cctggctgac | cgcccaacga | cccccgccca | ttgacgtcaa | taatgacgta | 300 |
| tgttcccata | gtaacgccaa | tagggacttt | ccattgacgt | caatgggtgg | agtatttacg | 360 |
| gtaaactgcc | cacttggcag | tacatcaagt | gtatcatatg | ccaagtacgc | cccctattga | 420 |
| cgtcaatgac | ggtaaatggc | ccgcctggca | ttatgcccag | tacatgacct | tatgggactt | 480 |
| tcctacttgg | cagtacatct | acgtattagt | catcgctatt | accatgcatg | gtcgaggtga | 540 |
| gccccacgtt | ctgcttcact | ctccccatct | ccccccctc | cccaccccca | attttgtatt | 600 |
| tatttatttt | ttaattattt | tgtgcagcga | tgggggcggg | gggggggggg | gggcgcgcgc | 660 |
| caggcgggc | ggggcgggc | gaggggcggg | gcggggcgag | gcgagaggt | gcggcggcag | 720 |
| ccaatcagag | cggcgcgctc | cgaaagtttc | cttttatggc | gaggcggcgg | cggcggcggc | 780 |
| cctataaaaa | gcgaagcgcg | cggcgggcgg | gagtcgctgc | gacgctgcct | tcgccccgtg | 840 |
| ccccgctccg | ccgccgcctc | gcgccgcccg | ccccggctct | gactgaccgc | gttactccca | 900 |
| caggtgagcg | ggcgggacgg | cccttctcct | ccgggctgta | attagcgctt | ggtttaatga | 960 |
| cggcttgttt | cttttctgtg | gctgcgtgaa | agccttgagg | ggctccggga | gggccctttg | 1020 |
| tgcggggga | gcggctcggg | gctgtccgcg | ggggacggc | tgccttcggg | ggggacgggg | 1080 |
| cagggcgggg | ttcggcttct | ggcgtgtgac | cggcggctct | agcagcctct | gctaaccatg | 1140 |
| ttcatgcctt | cttctttttc | ctacagctcc | tgggcaacgt | gctggttatt | gtgctgtctc | 1200 |
| atcatttgg | caaagaatta | agcttgagct | cgcgatccgc | agccatggat | tatggaggcg | 1260 |
| ccctgagtgc | cgttgggcgc | gagctgctat | ttgtaacgaa | cccagtagtc | gtcaatggct | 1320 |
| ctgtacttgt | gcctgaggac | cagtgttact | gcgcgggctg | gattgagtcg | cgtggcacaa | 1380 |
| acggtgccca | acggcgtcg | aacgtgctgc | aatggcttgc | tgctggcttc | tccatcctac | 1440 |
| tgcttatgtt | ttacgcctac | caaacatgga | agtcaacctg | cggctgggag | gagatctatg | 1500 |
| tgtgcgctat | cgagatggtc | aaggtgattc | ttcgagttctt | cttcgagttt | aagaacccgt | 1560 |
| ccatgctgta | tctagccaca | ggccaccgcg | tccagtggtt | gcgttacgcc | gagtggcttc | 1620 |
| tcacctgccc | ggtcattctc | attcacctgt | caaacctgac | gggcttgtcc | aacgactaca | 1680 |
| gcaggcgcac | tatgggtctg | cttgtgtctg | atattggcac | aattgtgtgg | ggcgccactt | 1740 |
| ccgctatggc | caccggatac | gtcaaggtca | tcttcttctg | cctgggtctg | tgttatggtg | 1800 |
| ctaacacgtt | ctttcacgct | gccaaggcct | acatcgaggg | ttaccatacc | gtgccgaagg | 1860 |
| gccggtgtcg | ccaggtggtg | actggcatgg | cttggctctt | cttcgtatca | tggggtatgt | 1920 |
| tccccatcct | gttcatcctc | ggccccgagg | gcttcggcgt | cctgagcgtg | tacggctcca | 1980 |
| ccgtcggcca | caccatcatt | gacctgatgt | cgaagaactg | ctgggtctg | ctcggccact | 2040 |
| acctgcgcgt | gctgatccac | gagcatatcc | tcatccacgg | cgacattcgc | aagaccacca | 2100 |

```
aattgaacat tggtggcact gagattgagg tcgagacgct ggtggaggac gaggccgagg    2160
ctggcgcggt caacaagggc accggcaagg aattcggagg cggaggtgga gctagctaac    2220
tcgagtctag acgtggtacc ttgactggta ttcttaacta tgttgctcct tttacgctat    2280
gtggatacgc tgctttaatg cctttgtatc atgctattgc ttcccgtatg gctttcattt    2340
tctcctcctt gtataaatcc tggttgctgt ctctttatga ggagttgtgg cccgttgtca    2400
ggcaacgtgg cgtggtgtgc actgtgtttg ctgacgcaac ccccactggt tgggcattg    2460 ccaccacctg tcagctcctt tccgggactt tcgctttccc cctccctatt gccacggcgg    2520
aactcatcgc cgcctgcctt gcccgctgct ggacaggggc tcggctgttg ggcactgaca    2580
attccgtggt gttgtcgggg aagctgacgt cctttccatg gctgctcgcc tgtgttgcca    2640
cctggattct gcgcgggacg tccttctgct acgtcccttc ggcctcaat ccagcggacc    2700 ttccttcccg cggcctgctg ccggctctgc ggcctcttcc gcgtcttcgc cttcgccctc    2760
agacgagtcg gatctccctt gggccgcct cccgcctga tgcggggatc ctctagagtc    2820
gagagatcta cgggtggcat ccctgtgacc cctccccagt gcctctcctg gcctggaag    2880 ttgccactcc agtgcccacc agccttgtcc taataaaatt aagttgcatc attttgtctg    2940
actaggtgtc cttctataat attatggggt ggagggggg ggtatggagc aaggggcaag    3000
ttgggaagac aacctgtagg gcctgcgggg tctattggga accaagctgg agtgcagtgg    3060
cacaatcttg gctcactgca atctccgcct cctgggttca agcgattctc ctgcctcagc    3120
ctcccgagtt gttgggattc caggcatgca tgaccaggct cagctaattt ttgtttttt    3180 ggtagagacg gggtttcacc atattggcca ggctggtctc caactcctaa tctcaggtga    3240 tctaccacc ttggcctccc aaattgctgg gattacaggc gtgaaccact gctcccttcc    3300
ctgtccttct gattttgtag gtaaccacgt gcggaccgag cggccgcagg aaccctagt    3360 gatggagttg ccactccct ctctgcgcgc tcgctcgctc actgaggccg ggcgaccaaa    3420
ggtcgcccga cgcccgggct ttgcccgggc ggcctcagtg agcgagcgag cgcgcagctg    3480
cctgcagg                                                            3488
```

<210> SEQ ID NO 31  
<211> LENGTH: 4427  
<212> TYPE: DNA  
<213> ORGANISM: Artificial Sequence  
<220> FEATURE:  
<223> OTHER INFORMATION: 5'- ITR-CAG-ChR2-GFP-{Kv2.1 Motif}-WPRE-bGHpolyA-ITR- 3'

<400> SEQUENCE: 31

```
cctgcaggca gctgcgcgct cgctcgctca ctgaggccgc ccgggcaaag cccgggcgtc      60
gggcgaccgg tggtcgcccg gcctcagtga gcgagcgagc gcgcagagag ggagtggcca     120
actccatcac taggggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga ccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc ccctattga     420 cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc cccaccccca atttttgtatt     600
```

```
tatttattttt ttaattatttt tgtgcagcga tggggggcggg gggggggggg gggcgcgcgc      660
caggcggggc ggggcggggc gagggcgggg gcggggcgag gcggagaggt gcggcggcag      720
ccaatcagag cggcgcgctc cgaaagtttc cttttatggc gaggcggcgg cggcggcggc      780
cctataaaaa gcgaagcgcg cggcgggcgg gagtcgctgc gacgctgcct tcgccccgtg      840
ccccgctccg ccgccgcctc gcgccgcccg ccccggctct gactgaccgc gttactccca      900
caggtgagcg ggcgggacgg cccttctcct ccgggctgta attagcgctt ggtttaatga      960
cggcttgttt cttttctgtg gctgcgtgaa agccttgagg ggctccggga gggccctttg     1020 tgcggggga gcggctcggg gctgtccgcg ggggacggc tgccttcggg ggggacgggg     1080
cagggcgggg ttcggcttct ggcgtgtgac cggcggctct agcagcctct gctaaccatg     1140
ttcatgcctt cttcttttc ctacagctcc tgggcaacgt gctggttatt gtgctgtctc     1200
atcattttgg caaagaatta agcttgagct cgcgatccgc agccatggat tatgaggcg     1260 ccctgagtgc cgttgggcgc gagctgctat ttgtaacgaa cccagtagtc gtcaatggct     1320
ctgtacttgt gcctgaggac cagtgttact gcgcgggctg gattgagtcg cgtggcacaa     1380
acggtgccca aacggcgtcg aacgtgctgc aatggcttgc tgctggcttc tccatcctac     1440
tgcttatgtt ttacgcctac caaacatgga agtcaacctg cggctgggag agatctatg     1500 tgtgcgctat cgagatggtc aaggtgattc ttgagttctt cttcgagttt aagaacccgt     1560
ccatgctgta tctagccaca ggccaccgcg tccagtggtt gcgttacgcc gagtggcttc     1620
tcacctgccc ggtcattctc attcacctgt caaacctgac gggcttgtcc aacgactaca     1680
gcaggcgcac tatgggtctg cttgtgtctg atattggcac aattgtgtgg ggcgccactt     1740
ccgctatggc caccggatac gtcaaggtca tcttcttctg cctgggtctg tgttatggtg     1800
ctaacacgtt ctttcacgct gccaaggcct acatcgaggg ttaccatacc gtgccgaagg     1860
gccggtgtcg ccaggtggtg actggcatgg cttggctctt cttcgtatca tggggtatgt     1920
tccccatcct gttcatcctc ggccccgagg gcttcggcgt cctgagcgtg tacgctcca     1980 ccgtcggcca caccatcatt gacctgatgt cgaagaactg ctggggtctg ctcggccact     2040
acctgcgcgt gctgatccac gagcatatcc tcatccacgg cgacattcgc aagaccacca     2100
aattgaacat tggtggcact gagattgagg tcgagacgct ggtggaggac gaggccgagg     2160
ctggcgcggt caacaagggc accggcaagg aattcggagg cggaggtgga gctagcaaag     2220
gagaagaact cttcactgga gttgtcccaa ttcttgttga attagatggt gatgttaacg     2280
gccacaagtt ctctgtcagt ggagagggtg aaggtgatgc aacatacgga aaacttaccc     2340
tgaagttcat ctgcactact ggcaaactgc ctgttccatg gccaacacta gtcactactc     2400
tgtgctatgg tgttcaatgc ttttcaagat acccggatca tatgaaacgg catgactttt     2460
tcaagagtgc catgcccgaa ggttatgtac aggaaaggac catcttcttc aaagatgacg     2520
gcaactacaa gacacgtgct gaagtcaagt ttgaaggtga tacccttgtt aatagaatcg     2580
agttaaaagg tattgacttc aaggaagatg gcaacattct gggacacaaa ttggaataca     2640
actataactc acacaatgta tacatcatgg cagacaaaca aaagaatgga atcaaagtga     2700
acttcaagac ccgccacaac attgaagatg gaagcgttca actagcagac cattatcaac     2760
aaaatactcc aattggcgat ggccctgtcc ttttaccaga caaccattac ctgtccacac     2820
aatctgccct ttcgaaagat cccaacgaaa agagagacca catggtcctt cttgagtttg     2880
taacagctgc tgggattaca catggcatgg atgaactgta caaccagtct cagcccatcc     2940
tgaacactaa ggagatggcc cctcagagta aaccccctga ggaactggaa atgagctcca     3000
```

```
tgccatctcc agtggctcct ctgccagcta ggaccgaggg cgtgattgac atgagaagca    3060
tgtctagtat cgatagcttc atttcctgcg ccaccgactt ccccgaagct acaaggtttt    3120
aactcgagtc tagacgtggt accgataatc aacctctgga ttacaaaatt tgtgaaagat    3180
tgactggtat tcttaactat gttgctcctt ttacgctatg tggatacgct gctttaatgc    3240
ctttgtatca tgctattgct tcccgtatgg ctttcatttt ctcctccttg tataaatcct    3300
ggttgctgtc tctttatgag gagttgtggc ccgttgtcag caacgtggc gtggtgtgca     3360 ctgtgtttgc tgacgcaacc cccactggtt ggggcattgc caccacctgt cagctccttt    3420
ccgggacttt cgctttcccc ctccctattg ccacggcgga actcatcgcc gcctgccttg    3480
cccgctgctg dacaggggct cggctgttgg gcactgacaa ttccgtggtg ttgtcgggga   3540
agctgacgtc ctttccatgg ctgctcgcct gtgttccac ctggattctg cgcgggacgt     3600
ccttctgcta cgtcccttcg ccctcaatc cagcggacct tccttcccgc ggcctgctgc     3660
cggctctgcg gcctcttccg cgtcttcgcc ttcgccctca gacgagtcgg atctccctt     3720 gggccgcctc ccgcctgat gcggggatcc tctagagtcg agagatctac gggtggcatc     3780
cctgtgaccc ctccccagtg cctctcctgg ccctggaagt tgccactcca gtgcccacca    3840
gccttgtcct aataaaatta agttgcatca ttttgtctga ctaggtgtcc ttctataata    3900
ttatggggtg gagggggggtg gtatggagca agggggcaagt tggaagaca acctgtaggg    3960 cctgcggggt ctattgggaa ccaagctgga gtgcagtggc acaatcttgg ctcactgcaa    4020
tctccgcctc ctgggttcaa gcgattctcc tgcctcagcc tcccgagttg ttgggattcc    4080
aggcatgcat gaccaggctc agctaatttt tgttttttg gtagagacgg ggtttcacca    4140
tattggccag gctggtctcc aactcctaat ctcaggtgat ctaccacct tggcctccca     4200 aattgctggg attacaggcg tgaaccactg ctcccttccc tgtccttctg attttgtagg    4260
taaccacgtg cggaccgagc ggccgcagga acccctagtg atggagttgg ccactccctc    4320
tctgcgcgct cgctcgctca ctgaggccgg gcgaccaaag gtcgcccgac gcccgggctt    4380
tgcccgggcg gcctcagtga gcgagcgagc gcgcagctgc ctgcagg                 4427
```

<210> SEQ ID NO 32
<211> LENGTH: 3719
<212> TYPE: DNA
<213> ORGANISM: Artificial Sequence
<220> FEATURE:
<223> OTHER INFORMATION: 5'-ITR-CAG-ChR2-{Kv2.1 Motif}-WPRE-bGHpolyA-ITR-3'

<400> SEQUENCE: 32

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac tagggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga ccccgcccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc ccctattga     420 cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct ccccccctc cccacccca attttgtatt     600
```

```
tatttattttt ttaattatttt tgtgcagcga tggggggcggg gggggggggg gggcgcgcgc    660
caggcggggc ggggcggggc gaggggcggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgcccgtg     840 ccccgctccg ccgccgcctc gcgccgcccg ccccggctct gactgaccgc gttactccca    900
caggtgagcg ggcgggacgg ccttctcct ccgggctgta attagcgctt ggtttaatga    960
cggcttgttt cttttctgtg gctgcgtgaa agccttgagg ggctccggga gggcccttg    1020 tgcgggggga gcggctcggg gctgtccgcg ggggacggc tgccttcggg ggggacgggg    1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatggat tatggaggcg    1260
ccctgagtgc cgttgggcgc gagctgctat ttgtaacgaa cccagtagtc gtcaatggct    1320
ctgtacttgt gcctgaggac cagtgttact gcgcgggctg gattgagtcg cgtggcacaa    1380
acggtgccca acggcgtcg aacgtgctgc aatggcttgc tgctggcttc tccatcctac    1440
tgcttatgtt ttacgcctac caaacatgga agtcaacctg cggctgggag gagatctatg    1500
tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctgggtctg ctcggccact    2040 acctgcgcgt gctgatccac gagcatatcc tcatccacgg cgacattcgc aagaccacca    2100
aattgaacat tggtggcact gagattgagg tcgagacgct ggtggaggac gaggccgagg    2160
ctggcgcggt caacaagggc accggcaagg aattcggagg cggaggtgga gctagccagt    2220
ctcagcccat cctgaacact aaggagatgg cccctcagag taaaccccct gaggaactgg    2280
aaatgagctc catgccatct ccagtggctc tctgccagc taggaccgag ggcgtgattg    2340
acatgagaag catgtctagt atcgatagct tcatttcctg cgccaccgac ttccccgaag    2400
ctacaaggtt ttaactcgag tctagacgtg gtaccgataa tcaacctctg gattacaaaa    2460
tttgtgaaag attgactggt attcttaact atgttgctcc ttttacgcta tgtggatacg    2520
ctgctttaat gcctttgtat catgctattg cttcccgtat ggctttcatt ttctcctcct    2580
tgtataaatc ctggttgctg tctctttatg aggagttgtg gcccgttgtc aggcaacgtg    2640
gcgtggtgtg cactgtgttt gctgacgcaa ccccactgg ttgggcatt gccaccacct    2700 gtcagctcct ttccgggact ttcgctttcc ccctccctat tgccacggcg gaactcatcg    2760
ccgcctgcct tgcccgctgc tggacagggg ctcggctgtt gggcactgac aattccgtgg    2820
tgttgtcggg gaagctgacg tccttttccat ggctgctcgc ctgtgttgcc acctggattc    2880
tgcgcgggac gtccttctgc tacgtccctt cggccctcaa tccagcggac cttccttccc    2940
```

| | | | | |
|---|---|---|---|---|
| gcggcctgct | gccggctctg | cggcctcttc | cgcgtcttcg | ccttcgccct cagacgagtc | 3000 |
| ggatctccct | ttgggccgcc | tccccgcctg | atgcggggat | cctctagagt cgagagatct | 3060 |
| acgggtggca | tccctgtgac | ccctccccag | tgcctctcct | ggccctggaa gttgccactc | 3120 |
| cagtgcccac | cagccttgtc | ctaataaaat | taagttgcat | cattttgtct gactaggtgt | 3180 |
| ccttctataa | tattatgggg | tggaggggggg | tggtatggag | caaggggcaa gttgggaaga | 3240 |
| caacctgtag | ggcctgcggg | gtctattggg | aaccaagctg | gagtgcagtg gcacaatctt | 3300 |
| ggctcactgc | aatctccgcc | tcctgggttc | aagcgattct | cctgcctcag cctcccgagt | 3360 |
| tgttgggatt | ccaggcatgc | atgaccaggc | tcagctaatt | tttgtttttt tggtagagac | 3420 |
| ggggtttcac | catattggcc | aggctggtct | ccaactccta | atctcaggtg atctacccac | 3480 |
| cttggcctcc | caaattgctg | ggattacagg | cgtgaaccac | tgctcccttc cctgtccttc | 3540 |
| tgattttgta | ggtaaccacg | tgcggaccga | gcggccgcag | gaaccctag tgatagagtt | 3600 |
| ggccactccc | tctctgcgcg | ctcgctcgct | cactgaggcc | gggcgaccaa aagtcgcccg | 3660 |
| acgcccgggc | tttgccccggg | cggcctcagt | gagcgagcga | gcgcgcagct gcctgcagg | 3719 |

<210> SEQ ID NO 33
<211> LENGTH: 4313
<212> TYPE: DNA
<213> ORGANISM: Artificial Sequence
<220> FEATURE:
<223> OTHER INFORMATION: 5'-ITR-CAG-ChR2-GFP-{Nav1.6 Motif}-WPRE-bGHpolyA-ITR- 3'

<400> SEQUENCE: 33

| | | | | |
|---|---|---|---|---|
| cctgcaggca | gctgcgcgct | cgctcgctca | ctgaggccgc | ccgggcaaag cccgggcgtc | 60 |
| gggcgacctt | tggtcgcccg | gcctcagtga | gcgagcgagc | gcgcagagag ggagtggcca | 120 |
| actccatcac | taggggttcc | tgcggccgca | cgcgtgatat | cctagttatt aatagtaatc | 180 |
| aattacgggg | tcattagttc | atagcccata | tatggagttc | cgcgttacat aacttacggt | 240 |
| aaatggcccg | cctggctgac | cgcccaacga | cccccgccca | ttgacgtcaa taatgacgta | 300 |
| tgttcccata | gtaacgccaa | tagggacttt | ccattgacgt | caatgggtgg agtatttacg | 360 |
| gtaaactgcc | cacttggcag | tacatcaagt | gtatcatatg | ccaagtacgc cccctattga | 420 |
| cgtcaatgac | ggtaaatggc | ccgcctggca | ttatgcccag | tacatgacct tatgggactt | 480 |
| tcctacttgg | cagtacatct | acgtattagt | catcgctatt | accatgcatg gtcgaggtga | 540 |
| gccccacgtt | ctgcttcact | ctccccatct | ccccccctc | cccaccccca atttgtatt | 600 |
| tatttatttt | ttaattattt | tgtgcagcga | tgggggcggg | ggggggggg gggcgcgcgc | 660 |
| caggcggggc | ggggcgggc | gaggggcggg | gcggggcgag | gcggagaggt gcggcggcag | 720 |
| ccaatcagag | cggcgcgctc | cgaaagtttc | cttttatggc | gaggcggcgg cggcggcggc | 780 |
| cctataaaaa | gcgaagcgcg | cggcgggcgg | gagtcgctgc | gacgctgcct tcgccccgtg | 840 |
| ccccgctccg | ccgccgcctc | gcgccgcccg | ccccggctct | gactgaccgc gttactccca | 900 |
| caggtgagcg | ggcgggacgg | cccttctcct | ccgggctgta | attagcgctt ggtttaatga | 960 |
| cggcttgttt | ctttttctgtg | gctgcgtgaa | agccttgagg | ggctccggga gggccctttg | 1020 |
| tgcgggggga | gcggctcggg | gctgtccgcg | ggggacggg | tgccttcggg ggggacgggg | 1080 |
| cagggcgggg | ttcggcttct | ggcgtgtgac | cggcggctct | agcagcctct gctaaccatg | 1140 |
| ttcatgcctt | cttctttttc | ctacagctcc | tgggcaacgt | gctggttatt gtgctgtctc | 1200 |
| atcatttgg | caaagaatta | agcttgagct | cgcgatccgc | agccatggat tatggaggcg | 1260 |

```
ccctgagtgc cgttgggcgc gagctgctat ttgtaacgaa cccagtagtc gtcaatggct    1320
ctgtacttgt gcctgaggac cagtgttact gcgcgggctg gattgagtcg cgtggcacaa    1380
acggtgccca aacggcgtcg aacgtgctgc aatggcttgc tgctggcttc tccatcctac    1440
tgcttatgtt ttacgcctac caaacatgga agtcaacctg cggctgggag agatctatg     1500 tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctgggtctg ctcggccact     2040 acctgcgcgt gctgatccac gagcatatcc tcatccacgg cgacattcgc aagaccacca    2100
aattgaacat tggtggcact gagattgagg tcgacgctgc ggtggaggac gaggccgagg    2160
ctggcgcggt caacaagggc accggcaagg aattcggagg cggaggtgga gctagcaaag    2220
gagaagaact cttcactgga gttgtcccaa ttcttgttga attagatggt gatgttaacg    2280
gccacaagtt ctctgtcagt ggagagggtg aaggtgatgc aacatacgga aaacttaccc    2340
tgaagttcat ctgcactact ggcaaactgc ctgttccatg gccaacacta gtcactactc    2400
tgtgctatgg tgttcaatgc ttttcaagat acccggatca tatgaaacgg catgactttt    2460
tcaagagtgc catgcccgaa ggttatgtac aggaaaggac catcttcttc aaagatgacg    2520
gcaactacaa gacacgtgct gaagtcaagt ttgaaggtga taccttgtt aatagaatcg     2580 agttaaaagg tattgacttc aaggaagatg gcaacattct gggacacaaa ttggaataca    2640
actataactc acacaatgta tacatcatgg cagacaaaca aaagaatgga atcaaagtga    2700
acttcaagac ccgccacaac attgaagatg gaagcgttca actagcagac cattatcaac    2760
aaaatactcc aattggcgat ggccctgtcc ttttaccaga caaccattac ctgtccacac    2820
aatctgccct ttcgaaagat cccaacgaaa agagagacca catggtcctt cttgagtttg    2880
taacagctgc tgggattaca catggcatgg atgaactgta caacaccgtg agggtgccca    2940
tcgccgtggg cgagagcgac ttcgagaacc tgaacaccga ggacgtgagc agcgagagcg    3000
acccctaact cgagtctaga cgtggtaccg ataatcaacc tctggattac aaaatttgtg    3060
aaagattgac tggtattctt aactatgttg ctccttttac gctatgtgga tacgctgctt    3120
taatgccttt gtatcatgct attgcttccc gtatggcttt cattttctcc tccttgtata    3180
aatcctggtt gctgtctctt tatgaggagt tgtggcccgt tgtcaggcaa cgtggcgtgg    3240
tgtgcactgt gtttgctgac gcaacccccca ctggttgggg cattgccacc acctgtcagc   3300
tcctttccgg gactttcgct ttccccctcc ctattgccac ggcggaactc atcgccgcct    3360
gccttgcccg ctgctggaca ggggctcggc tgttgggcac tgacaattcc gtggtgttgt    3420
cggggaagct gacgtccttt ccatggctgc tcgcctgtgt tgccacctgg attctgcgcg    3480
ggacgtcctt ctgctacgtc ccttcggccc tcaatccagc ggaccttcct tcccgcggcc    3540
tgctgccggc tctgcggcct cttccgcgtc ttcgccttcg ccctcagacg agtcggatct    3600
ccctttgggc cgcctccccg cctgatgcgg ggatcctcta gagtcgagag atctacgggt    3660
```

```
ggcatccctg tgacccctcc ccagtgcctc tcctggccct ggaagttgcc actccagtgc    3720
ccaccagcct tgtcctaata aaattaagtt gcatcatttt gtctgactag gtgtccttct    3780
ataatattat ggggtggagg ggggtggtat ggagcaaggg gcaagttggg aagacaacct    3840
gtagggcctg cggggtctat tgggaaccaa gctggagtgc agtggcacaa tcttggctca    3900
ctgcaatctc cgcctcctgg gttcaagcga ttctcctgcc tcagcctccc gagttgttgg    3960
gattccaggc atgcatgacc aggctcagct aattttttgtt ttttggtag agacggggtt    4020 tcaccatatt ggccaggctg gtctccaact cctaatctca ggtgatctac ccaccttggc    4080
ctcccaaatt gctgggatta caggcgtgaa ccactgctcc cttccctgtc cttctgattt    4140
tgtaggtaac cacgtgcgga ccgagcggcc gcaggaaccc ctagtgatgg agttggccac    4200
tccctctctg cgcgctcgct cgctcactga ggccgggcga ccaaaggtcg cccgacgccc    4260
gggctttgcc cggcggcct cagtgagcga gcgagcgcgc agctgcctgc agg            4313

<210> SEQ ID NO 34
<211> LENGTH: 3605
<212> TYPE: DNA
<213> ORGANISM: Artificial Sequence
<220> FEATURE:
<223> OTHER INFORMATION: 5' -ITR-CAG-ChR2-{Nav1.6Motif}-WPRE-bGHpolyA-
      ITR- 3'

<400> SEQUENCE: 34
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc cccctattga    420
cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct cccccccctc cccacccca attttgtatt    600 tatttatttt ttaattattt tgtgcagcga tgggggcggg ggggggggg gggcgcgcgc    660 caggcgggc ggggcggggc gaggggcggg gcggggcgag gcgagagggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg cccggctct gactgaccgc gttactccca    900
caggtgagcg ggcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg ggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200 atcatttttgg caaagaatta agcttgagct cgcgatccgc agccatggat tatgaggcg   1260 ccctgagtgc cgttgggcgc gagctgctat ttgtaacgaa cccagtagtc gtcaatggct   1320
ctgtacttgt gcctgaggac cagtgttact gcgcgggctg gattgagtcg cgtggcacaa   1380
```

```
acggtgccca aacggcgtcg aacgtgctgc aatggcttgc tgctggcttc tccatcctac    1440
tgcttatgtt ttacgcctac caaacatgga agtcaacctg cggctgggag agatctatg    1500 tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctggggtctg ctcggccact    2040
acctgcgcgt gctgatccac gagcatatcc tcatccacgg cgacattcgc aagaccacca    2100
aattgaacat tggtggcact gagattgagg tcgagacgct ggtggaggac gaggccgagg    2160
ctggcgcggt caacaagggc accggcaagg aattcggagg cggaggtgga gctagcaccg    2220
tgagggtgcc catcgccgtg ggcgagagcg acttcgagaa cctgaacacc gaggacgtga    2280
gcagcgagag cgaccoctaa ctcgagtcta gacgtggtac cgataatcaa cctctggatt    2340
acaaaatttg tgaaagattg actggtattc ttaactatgt tgctcctttt acgctatgtg    2400
gatacgctgc tttaatgcct ttgtatcatg ctattgcttc ccgtatggct ttcattttct    2460
cctccttgta taaatcctgg ttgctgtctc tttatgagga gttgtggccc gttgtcaggc    2520
aacgtggcgt ggtgtgcact gtgtttgctg acgcaacccc cactggttgg ggcattgcca    2580
ccacctgtca gctcctttcc gggactttcg cttctcccct ccctattgcc acggcggaac    2640
tcatcgccgc ctgccttgcc cgctgctgga caggggctcg gctgttgggc actgacaatt    2700
ccgtggtgtt gtcggggaag ctgacgtcct ttccatggct gctcgcctgt gttgccacct    2760
ggattctgcg cgggacgtcc ttctgctacg tcccttcggc cctcaatcca gcggaccttc    2820
cttcccgcgg cctgctgccg gctctgcggc ctcttccgcg tcttcgcctt cgccctcaga    2880
cgagtcggat ctccctttgg gccgcctccc cgcctgatgc ggggatcctc tagagtcgag    2940
agatctacgg gtggcatccc tgtgacccct ccccagtgcc tctcctggcc ctggaagttg    3000
ccactccagt gcccaccagc cttgtcctaa taaaattaag ttgcatcatt ttgtctgact    3060
aggtgtcctt ctataatatt atggggtgga gggggtggt atggagcaag ggcaagttg    3120 ggaagacaac ctgtagggcc tgcggggtct attgggaacc aagctggagt gcagtggcac    3180
aatcttggct cactgcaatc tccgcctcct gggttcaagc gattctcctg cctcagcctc    3240
ccgagttgtt gggattccag gcatgcatga ccaggctcag ctaatttttg tttttttggt    3300
agagacgggg tttcaccata ttggccaggc tggtctccaa ctcctaatct caggtgatct    3360
acccaccttg gcctcccaaa ttgctgggat tacaggcgtg aaccactgct cccttccctg    3420
tccttctgat tttgtaggta accacgtgcg gaccgagcgg ccgcaggaac ccctagtgat    3480
ggagttggcc actccctctc tgcgcgctcg ctcgctcact gaggccgggc gaccaaaggt    3540
cgcccgacgc ccgggctttg cccgggcggc ctcagtgagc gagcgagcgc gcagctgcct    3600
gcagg                                                                3605
```

<210> SEQ ID NO 35

```
<211> LENGTH: 4328
<212> TYPE: DNA
<213> ORGANISM: Artificial Sequence
<220> FEATURE:
<223> OTHER INFORMATION: 5'- ITR-CAG-ChR2-GFP-{NLG1 Motif}-WPRE-
      bGHpolyA-ITR- 3'

<400> SEQUENCE: 35
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga cccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc cccctattga     420
cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc cccaccccca attttgtatt     600
tatttatttt ttaattattt tgtgcagcga tgggggcggg ggggggggg gggcgcgcgc     660
caggcgggc ggggcgggc gaggggcggg gcggggcgag gcgagaggt gcggcggcag     720
ccaatcagag cggcgcgctc cgaaagtttc cttttatggc gaggcggcgg cggcggcggc     780
cctataaaaa gcgaagcgcg cggcgggcgg gagtcgctgc gacgctgcct tcgccccgtg     840
ccccgctccg ccgccgcctc gcgccgcccg cccggctct gactgaccgc gttactccca     900
caggtgagcg ggcgggacgg cccttctcct ccgggctgta attagcgctt ggtttaatga     960
cggcttgttt cttttctgtg gctgcgtgaa agccttgagg ggctccggga gggccctttg    1020
tgcgggggga gcggctcggg gctgtccgcg ggggacggc tgccttcggg ggggacgggg    1080
cagggcgggg ttcggcttct ggcgtgtgac cggcggctct agcagcctct gctaaccatg    1140
ttcatgcctt cttcttttttc ctacagctcc tgggcaacgt gctggttatt gtgctgtctc    1200
atcattttgg caaagaatta agcttgagct cgcgatccgc agccatggat tatggaggcg    1260
ccctgagtgc cgttgggcgc gagctgctat ttgtaacgaa cccagtagtc gtcaatggct    1320
ctgtacttgt gcctgaggac cagtgttact gcgcgggctg gattgagtcg cgtggcacaa    1380
acggtgccca acggcgtcg aacgtgctgc aatggcttgc tgctggcttc tccatcctac    1440
tgcttatgtt ttacgcctac caaacatgga agtcaacctg cggctgggag gagatctatg    1500
tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctgggtctg ctcggccact    2040
acctgcgcgt gctgatccac gagcatatcc tcatccacgg cgacattcgc aagaccacca    2100
```

```
aattgaacat tggtggcact gagattgagg tcgagacgct ggtggaggac gaggccgagg    2160
ctggcgcggt caacaagggc accggcaagg aattcggagg cggaggtgga gctagcaaag    2220
gagaagaact cttcactgga gttgtcccaa ttcttgttga attagatggt gatgttaacg    2280
gccacaagtt ctctgtcagt ggagagggtg aaggtgatgc aacatacgga aaacttaccc    2340
tgaagttcat ctgcactact ggcaaactgc ctgttccatg gccaacacta gtcactactc    2400
tgtgctatgg tgttcaatgc ttttcaagat acccggatca tatgaaacgg catgactttt    2460
tcaagagtgc catgcccgaa ggttatgtac aggaaaggac catcttcttc aaagatgacg    2520
gcaactacaa gacacgtgct gaagtcaagt ttgaaggtga tacccttgtt aatagaatcg    2580
agttaaaagg tattgacttc aaggaagatg gcaacattct gggacacaaa ttggaataca    2640
actataactc acacaatgta tacatcatgg cagacaaaca aaagaatgga atcaaagtga    2700
acttcaagac ccgccacaac attgaagatg gaagcgttca actagcagac cattatcaac    2760
aaaatactcc aattggcgat ggccctgtcc ttttaccaga caaccattac ctgtccacac    2820
aatctgccct ttcgaaagat cccaacgaaa agagagacca catggtcctt cttgagtttg    2880
taacagctgc tgggattaca catggcatgg atgaactgta caagtggtt cttcggaccg    2940 cctgtccccc agattacaca ctagctatga ggaggtcacc tgatgatgtt cccttaatga    3000
cacccaacac cattacaatg taactcgagt ctagacgtgg taccgataat caacctctgg    3060
attacaaaat ttgtgaaaga ttgactggta ttcttaacta tgttgctcct tttacgctat    3120
gtggatacgc tgctttaatg cctttgtatc atgctattgc ttcccgtatg gctttcattt    3180
tctcctcctt gtataaatcc tggttgctgt ctctttatga ggagttgtgg cccgttgtca    3240
ggcaacgtgg cgtggtgtgc actgtgtttg ctgacgcaac ccccactggt tggggcattg    3300
ccaccacctg tcagctcctt tccgggactt tcgctttccc cctccctatt gccacggcgg    3360
aactcatcgc cgcctgcctt gcccgctgct ggacaggggc tcggctgttg ggcactgaca    3420
attccgtggt gttgtcgggg aagctgacgt ccttttccatg gctgctcgcc tgtgttgcca    3480
cctggattct gcgcgggacg tccttctgct acgtcccttc ggccctcaat ccagcggacc    3540
ttccttcccg cggcctgctg ccggctctgc ggcctcttcc gcgtcttcgc cttcgccctc    3600
agacgagtcg gatctcccctt tgggccgcct ccccgcctga tgcgggatc ctctagagtc    3660 gagagatcta cgggtggcat ccctgtgacc cctccccagt gcctctcctg gcctggaag    3720 ttgccactcc agtgcccacc agccttgtcc taataaaatt aagttgcatc attttgtctg    3780
actaggtgtc cttctataat attatggggt ggagggggt ggtatggagc aaggggcaag    3840
ttgggaagac aacctgtagg gcctgcgggg tctattggga accaagctgg agtgcagtgg    3900
cacaatcttg gctcactgca atctccgcct cctgggttca agcgattctc ctgcctcagc    3960
ctcccgagtt gttgggattc caggcatgca tgaccaggct cagctaattt tgtttttttt    4020
ggtagagacg gggtttcacc atattggcca ggctggtctc caactcctaa tctcaggtga    4080
tctacccacc ttggcctccc aaattgctgg gattacaggc gtgaaccact gctcccttcc    4140
ctgtccttct gattttgtag gtaaccacgt gcggaccgag cggccgcagg aacccctagt    4200
gatagagttg gccactccct ctctgcgcgc tcgctcgctc actgaggccg ggcgaccaaa    4260
ggtcgcccga cgcccgggct ttgcccgggc ggcctcagtg agcgagcgag cgcgcagctg    4320
cctgcagg                                                            4328
```

<210> SEQ ID NO 36
<211> LENGTH: 3620

<212> TYPE: DNA
<213> ORGANISM: Artificial Sequence
<220> FEATURE:
<223> OTHER INFORMATION: 5'- ITR-CAG-ChR2-{NLG-1Motif}-WPRE-bGHpolyA-
      ITR- 3'

<400> SEQUENCE: 36

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga ccccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc cccctattga     420
cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc cccaccccca attttgtatt     600
tatttatttt ttaattattt tgtgcagcga tgggggcggg ggggggggg gggcgcgcgc      660
caggcggggc ggggcggggc gaggggcggg gcggggcgag gcggagaggt gcggcggcag     720
ccaatcagag cggcgcgctc cgaaagtttc cttttatggc gaggcggcgg cggcggcggc     780
cctataaaaa gcgaagcgcg cggcgggcgg gagtcgctgc gacgctgcct tcgccccgtg     840
ccccgctccg ccgccgcctc gcgccgcccg ccccggctct gactgaccgc gttactccca     900
caggtgagcg gcgggacgg cccttctcct ccgggctgta attagcgctt ggtttaatga     960
cggcttgttt cttttctgtg gctgcgtgaa agccttgagg ggctccggga gggccctttg    1020
tgcgggggga gcggctcggg gctgtccgcg ggggacggc tgccttcggg gggacgggg     1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatggat tatgaggcg     1260
ccctgagtgc cgttgggcgc gagctgctat ttgtaacgaa cccagtagtc gtcaatggct    1320
ctgtacttgt gcctgaggac cagtgttact gcgcgggctg gattgagtcg cgtgcacaa     1380
acggtgccca acggcgtcg aacgtgctgc aatggcttgc tgctggcttc tccatcctac    1440
tgcttatgtt ttacgcctac caaacatgga agtcaacctg cggctgggag agatctatg    1500
tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctgggtctg ctcggccact    2040
acctgcgcgt gctgatccac gagcatatcc tcatccacgg cgacattcgc aagaccacca    2100
aattgaacat tggtggcact gagattgagg tcgagacgct ggtggaggac gaggccgagg    2160
```

```
ctggcgcggt caacaagggc accggcaagg aattcggagg cggaggtgga gctagcgtgg    2220
ttcttcggac cgcctgtccc ccagattaca cactagctat gaggaggtca cctgatgatg    2280
ttcccttaat gacacccaac accattacaa tgtaactcga gtctagacgt ggtaccgata    2340
atcaacctct ggattacaaa atttgtgaaa gattgactgg tattcttaac tatgttgctc    2400
cttttacgct atgtggatac gctgctttaa tgcctttgta tcatgctatt gcttcccgta    2460
tggctttcat tttctcctcc ttgtataaat cctggttgct gtctctttat gaggagttgt    2520
ggcccgttgt caggcaacgt ggcgtggtgt gcactgtgtt tgctgacgca accccactg     2580 gttgggcat tgccaccacc tgtcagctcc tttccgggac tttcgctttc ccctcccta     2640 ttgccacggc ggaactcatc gccgcctgcc ttgcccgctg ctggacaggg gctcggctgt    2700
tgggcactga caattccgtg tgtgttgtcgg gaagctgac gtccttcca tggctgctcg    2760 cctgtgttgc cacctggatt ctgcgcggga cgtccttctg ctacgtccct tcggccctca    2820
atccagcgga ccttccttcc gcggcctgc tgcggctct gcggcctctt ccgcgtcttc     2880
gccttcgccc tcagacgagt cggatctccc tttgggccgc ctccccgcct gatgcgggga    2940
tcctctagag tcgagagatc tacggtggc atccctgtga cccctcccca gtgcctctcc    3000
tggccctgga agttgccact ccagtgccca ccagccttgt cctaataaaa ttaagttgca    3060
tcattttgtc tgactaggtg tccttctata atattatggg gtggagggggg gtggtatgga    3120 gcaagggca agttgggaag acaacctgta gggcctgcgg ggtctattgg gaaccaagct    3180
ggagtgcagt ggcacaatct tggctcactg caatctccgc ctcctgggtt caagcgattc    3240
tcctgcctca gcctcccgag ttgttgggat tccaggcatg catgaccagg ctcagctaat    3300
ttttgttttt ttggtagaga cggggtttca ccatattggc caggctggtc tccaactcct    3360
aatctcaggt gatctaccca ccttggcctc ccaaattgct gggattacag gcgtgaacca    3420
ctgctccctt ccctgtcctt ctgattttgt aggtaaccac gtgcggaccg agcggccgca    3480 ggaacccta gtgatggagt tggccactcc ctctctgcgc gctcgctcgc tcactgaggc    3540
cgggcgacca aagtcgccc gacgcccggg ctttgcccgg gcggcctcag tgagcgagcg    3600
agcgcgcagc tgcctgcagg                                                3620

<210> SEQ ID NO 37
<211> LENGTH: 4310
<212> TYPE: DNA
<213> ORGANISM: Artificial Sequence
<220> FEATURE:
<223> OTHER INFORMATION: 5'- ITR-CAG-ChR2-GFP-{MLPH Motif}-WPRE-
      bGHpolyA-ITR- 3'

<400> SEQUENCE: 37
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga ccccgcccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc ccctattga      420 cgtcaatgac ggtaaatggc ccgcctggca ttatgcccag tacatgacct tatgggactt     480
tcctacttgg cagtacatct acgtattagt catcgctatt accatgcatg gtcgaggtga     540
```

```
gccccacgtt ctgcttcact ctccccatct ccccccccctc cccaccccca attttgtatt    600
tatttatttt ttaattattt tgtgcagcga tgggggcggg ggggggggggg gggcgcgcgc    660 caggcggggc ggggcggggc gagggcgggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg ggcgggacgg cccttctcct ccgggctgta attagcgctt ggtttaatga    960
cggcttgttt cttttctgtg gctgcgtgaa agccttgagg ggctccggga gggcccttttg   1020 tgcgggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttcttttttc ctacagctcc tgggcaacgt gctggttatt gtgctgtctc   1200
atcattttgg caaagaatta agcttgagct cgcgatccgc agccatggat tatggaggcg   1260
ccctgagtgc cgttgggcgc gagctgctat ttgtaacgaa cccagtagtc gtcaatggct   1320
ctgtacttgt gcctgaggac cagtgttact gcgcgggctg gattgagtcg cgtggcacaa   1380
acggtgccca acggcgtcg aacgtgctgc aatggcttgc tgctggcttc tccatcctac   1440
tgcttatgtt ttacgcctac caaacatgga agtcaacctg cggctgggag agatctatg    1500 tgtgcgctat cgagatggtc aaggtgattc ttgagttctt cttcgagtttt aagaacccgt   1560 ccatgctgta tctagccaca ggccaccgcg tccagtggtt gcgttacgcc gagtggcttc   1620
tcacctgccc ggtcattctc attcacctgt caaacctgac gggcttgtcc aacgactaca   1680
gcaggcgcac tatgggtctg cttgtgtctg atattggcac aattgtgtgg ggcgccactt   1740
ccgctatggc caccggatac gtcaaggtca tcttcttctg cctgggtctg tgttatggtg   1800
ctaacacgtt ctttcacgct gccaaggcct acatcgaggg ttaccatacc gtgccgaagg   1860
gccggtgtcg ccaggtggtg actggcatgg cttggctctt cttcgtatca tggggtatgt   1920
tccccatcct gttcatcctc ggccccgagg gcttcggcgt cctgagcgtg tacggctcca   1980
ccgtcggcca caccatcatt gacctgatgt cgaagaactg ctgggggtctg ctcggccact   2040 acctgcgcgt gctgatccac gagcatatcc tcatccacgg cgacattcgc aagaccacca   2100
aattgaacat tggtggcact gagattgagg tcgagacgct ggtggaggac gaggccgagg   2160
ctggcgcggt caacaagggc accggcaagg aattcggagg cggaggtgga gctagcaaag   2220
gagaagaact cttcactgga gttgtcccaa ttcttgttga attagatggt gatgttaacg   2280
gccacaagtt ctctgtcagt ggagagggtg aaggtgatgc aacatacgga aaacttaccc   2340
tgaagttcat ctgcactact ggcaaactgc ctgttccatg gccaacacta gtcactactc   2400
tgtgctatgg tgttcaatgc ttttcaagat acccggatca tatgaaacgg catgactttt   2460
tcaagagtgc catgcccgaa ggttatgtac aggaaaggac catcttcttc aaagatgacg   2520
gcaactacaa gacacgtgct gaagtcaagt ttgaaggtga taccccttgtt aatagaatcg   2580 agttaaaagg tattgacttc aaggaagatg gcaacattct gggacacaaa ttggaataca   2640
actataactc acacaatgta tacatcatgg cagacaaaca aaagaatgga atcaaagtga   2700
acttcaagac ccgccacaac attgaagatg aagcgttcaa actagcagac cattatcaac   2760
aaaatactcc aattggcgat ggccctgtcc ttttaccaga caaccattac ctgtccacac   2820
aatctgccct ttcgaaagat cccaacgaaa agagagacca catggtcctt cttgagtttg   2880
```

```
taacagctgc tgggattaca catggcatgg atgaactgta caacagggac cagcctctga    2940
acagcaaaaa gaaaagagg ctcctgagct tcagggacgt ggacttcgag gaggacagcg     3000
actaactcga gtctagacgt ggtaccgata atcaacctct ggattacaaa atttgtgaaa    3060
gattgactgg tattcttaac tatgttgctc cttttacgct atgtggatac gctgctttaa    3120
tgcctttgta tcatgctatt gcttcccgta tggctttcat tttctcctcc ttgtataaat    3180
cctggttgct gtctctttat gaggagttgt ggcccgttgt caggcaacgt ggcgtggtgt    3240
gcactgtgtt tgctgacgca acccccactg gttgggcat tgccaccacc tgtcagctcc     3300
tttccgggac tttcgctttc cccctcccta ttgccacggc ggaactcatc gccgcctgcc    3360
ttgcccgctg ctggacaggg gctcggctgt tgggcactga caattccgtg tgtgttgtcgg    3420 ggaagctgac gtccttttcca tggctgctcg cctgtgttgc cacctggatt ctgcgcggga   3480
cgtccttctg ctacgtccct tcggccctca atccagcgga ccttccttcc cgcggcctgc    3540
tgccggctct gcggcctctt ccgcgtcttc gccttcgccc tcagacgagt cggatctccc    3600
tttgggccgc ctccccgcct gatgcgggga tcctctagag tcgagatc tacgggtggc     3660 atccctgtga ccctcccca gtgcctctcc tggccctgga agttgccact ccagtgccca     3720
ccagccttgt cctaataaaa ttaagttgca tcatttttgtc tgactaggtg tccttctata   3780
atattatggg gtggagggg gtggtatgga gcaaggggca agttgggaag acaacctgta     3840
gggcctgcgg ggtctattgg gaaccaagct ggagtgcagt ggcacaatct ggctcactg     3900 caatctccgc ctcctgggtt caagcgattc tcctgcctca gcctcccgag ttgttgggat    3960
tccaggcatg catgaccagg ctcagctaat ttttgttttt ttggtagaga cggggtttca    4020
ccatattggc caggctggtc tccaactcct aatctcaggt gatctaccca ccttggcctc    4080
ccaaattgct gggattacag gcgtgaacca ctgctccctt ccctgtcctt ctgatttgt     4140 aggtaaccac gtgcggaccg agcggccgca ggaaccccta gtgatggagt tggccactcc    4200
ctctctgcgc gctcgctcgc tcactgaggc cgggcgacca aaggtcgccc gacgcccggg    4260 cttttgcccgg gcggcctcag tgagcgagcg agcgcgcagc tgcctgcagg              4310
```

<210> SEQ ID NO 38
<211> LENGTH: 3602
<212> TYPE: DNA
<213> ORGANISM: Artificial Sequence
<220> FEATURE:
<223> OTHER INFORMATION: 5'- ITR-CAG-ChR2-{MLPH-Motif}-WPRE-bGHpolyA-
      ITR- 3'

<400> SEQUENCE: 38

```
cctgcaggca gctgcgcgct cgctcgctca ctgaggccgc ccgggcaaag cccgggcgtc      60
gggcgacctt tggtcgcccg gcgcagtga gcgagcgagc gcgcagagag ggagtggcca     120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc ccctattga     420 cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct cccccccctc cccacccca atttgtatt      600
```

```
tatttattttt ttaattattt tgtgcagcga tgggggcggg gggggggggg gggcgcgcgc    660
caggcggggc ggggcgggc gagggcggg gcggcgag gcggagaggt gcggcggcag        720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgcccgtg    840 ccccgctccg ccgccgcctc gcgccgcccg ccccggctct gactgaccgc gttactccca   900
caggtgagcg ggcgggacgg cccttctcct ccgggctgta attagcgctt ggtttaatga   960
cggcttgttt cttttctgtg gctgcgtgaa agccttgagg ggctccggga gggccctttg  1020
tgcgggggga gcggctcggg gctgtccgcg gggggacggc tgccttcggg ggggacgggg  1080
cagggcgggg ttcggcttct ggcgtgtgac cggcggctct agcagcctct gctaaccatg  1140
ttcatgcctt cttctttttc ctacagctcc tgggcaacgt gctggttatt gtgctgtctc  1200
atcattttgg caaagaatta agcttgagct cgcgatccgc agccatggat tatgaggcg   1260 ccctgagtgc cgttgggcgc gagctgctat ttgtaacgaa cccagtagtc gtcaatggct  1320
ctgtacttgt gcctgaggac cagtgttact gcgcgggctg gattgagtcg cgtggcacaa  1380
acggtgccca acggcgtcg aacgtgctgc aatggcttgc tgctggcttc tccatcctac   1440
tgcttatgtt ttacgcctac caaacatgga agtcaacctg cggctgggag gagatctatg  1500
tgtgcgctat cgagatggtc aaggtgattc ttgagttctt cttcgagttt aagaacccgt   1560
ccatgctgta tctagccaca ggccaccgcg tccagtggtt gcgttacgcc gagtggcttc   1620
tcacctgccc ggtcattctc attcacctgt caaacctgac gggcttgtcc aacgactaca   1680
gcaggcgcac tatgggtctg cttgtgtctg atattggcac aattgtgtgg ggcgccactt   1740
ccgctatggc caccggatac gtcaaggtca tcttcttctg cctgggtctg tgttatggtg   1800
ctaacacgtt ctttcacgct gccaaggcct acatcgaggg ttaccatacc gtgccgaagg   1860
gccggtgtcg ccaggtggtg actggcatgg cttggctctt cttcgtatca tggggtatgt   1920
tccccatcct gttcatcctc ggccccgagg gcttcggcgt cctgagcgtg tacggctcca   1980
ccgtcggcca caccatcatt gacctgatgt cgaagaactg ctggggtctg ctcggccact   2040
acctgcgcgt gctgatccac gagcatatcc tcatccacgg cgacattcgc aagaccacca   2100
aattgaacat tggtggcact gagattgagg tcgagacgct ggtggaggac gaggccgagg   2160
ctggcgcggt caacaagggc accggcaagg aattcggagg cggaggtgga gctagcaggg   2220
accagcctct gaacagcaaa aagaaaaga ggctcctgag cttcagggac gtggacttcg    2280
aggaggacag cgactaactc gagtctagac gtggtaccga taatcaacct ctggattaca   2340
aaatttgtga agattgact ggtattctta actatgttgc tccttttacg ctatgtggat    2400
acgctgcttt aatgcctttg tatcatgcta ttgcttcccg tatggctttc attttctcct   2460
ccttgtataa atcctggttg ctgtctcttt atgaggagtt gtgcccgtt gtcaggcaac    2520 gtggcgtggt gtgcactgtg tttgctgacg caacccccac tggttgggc attgccacca   2580 cctgtcagct cctttccggg actttcgctt tccccctccc tattgccacg gcggaactca   2640
tcgccgcctg ccttgcccgc tgctggacag gggctcggct gttgggcact gacaattccg   2700
tggtgttgtc ggggaagctg acgtccttc catggctgct cgcctgtgtt gccacctgga    2760
ttctgcgcgg gacgtccttc tgctacgtcc cttcggccct caatccagcg gaccttcctt   2820
cccgcggcct gctgcggct ctgcggcctc ttccgcgtct tcgccttcgc cctcagacga    2880
gtcggatctc cctttgggcc gcctccccgc ctgatgcggg gatcctctag agtcgagaga   2940 tctacggggtg gcatccctgt gacccctccc cagtgcctct cctggccctg gaagttgcca   3000
```

-continued

```
ctccagtgcc caccagcctt gtcctaataa aattaagttg catcattttg tctgactagg    3060
tgtccttcta taatattatg gggtggaggg gggtggtatg gagcaagggg caagttggga    3120
agacaacctg tagggcctgc ggggtctatt gggaaccaag ctggagtgca gtggcacaat    3180
cttggctcac tgcaatctcc gcctcctggg ttcaagcgat tctcctgcct cagcctcccg    3240
agttgttggg attccaggca tgcatgacca ggctcagcta attttgtttt ttttggtaga    3300
gacgggtttt caccatattg gccaggctgg tctccaactc ctaatctcag gtgatctacc    3360
caccttggcc tcccaaattg ctgggattac aggcgtgaac cactgctccc ttccctgtcc    3420
ttctgatttt gtaggtaacc acgtgcggac cgagcggccg caggaacccc tagtgatgga    3480
gttggccact ccctctctgc gcgctcgctc gctcactgag gccgggcgac caaaggtcgc    3540
ccgacgcccg ggctttgccc gggcggcctc agtgagcgag cgagcgcgca gctgcctgca    3600
gg    3602
```

```
<210> SEQ ID NO 39
<211> LENGTH: 4361
<212> TYPE: DNA
<213> ORGANISM: Artificial Sequence
<220> FEATURE:
<223> OTHER INFORMATION: 5'- ITR-CAG-HaloR-GFP-{Kv2 .1Motif}-WPRE-
      bGHpolyA-ITR- 3'

<400> SEQUENCE: 39
```

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga cccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc cccctattga     420
cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct cccccccctc cccaccccca attttgtatt     600
tatttatttt ttaattattt tgtgcagcga tggggggcggg gggggggggg gggcgcgcgc     660 caggcgggc ggggcgggc gaggggcggg gcggggcgag gcgagagggt gcggcggcag     720
ccaatcagag cggcgcgctc cgaaagtttc cttttatggc gaggcggcgg cggcggcggc     780
cctataaaaa gcgaagcgcg cggcgggcgg gagtcgctgc gacgctgcct tcgccccgtg     840
ccccgctccg ccgccgcctc gcgccgcccg ccccggctct gactgaccgc gttactccca     900
caggtgagcg gcgggacgg cccttctcct ccgggctgta attagcgctt ggtttaatga     960
cggcttgttt cttttctgtg gctgcgtgaa agccttgagg ggctccggga gggccctttg    1020 tgcggggga gcggctcggg gctgtccgcg ggggacggc tgccttcggg gggacgggg     1080 cagggcgggg ttcggcttct ggcgtgtgac cgcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatgact gagacattgc    1260
caccggtaac ggaatcggct gttgcgctac aggcggaggt gacccagagg gagctgttcg    1320
agttcgttct caacgacccc ctcctcgcca gttcgctgta tattaatatc gcactggcag    1380
```

```
ggctgtcgat actgcttttc gtgttcatga cgcgcggact cgacgaccca cgggcgaaac   1440
tcatcgccgt ttcgacgatt ttggtgccgg tggtctctat cgcgagctac accggccttg   1500
catcggggct caccatcagc gtcctcgaga tgccagccgg ccacttcgcc gagggtcct    1560
cggtgatgct cggcggcgaa gaggtagacg gcgtcgtgac gatgtgggc cgctatctga    1620
cgtgggccct ttcgacaccg atgatactgc tggcgcttgg gctgcttgct ggctctaacg   1680
ccacgaagct ctttaccgcc atcaccttcg acatcgcgat gtgtgtcacc ggcctcgcag   1740
ccgcgctgac gacctcttcg cacctgatgc ggtggttctg gtacgccatc agttgtgcgt   1800
gtttcctcgt cgtcctctac atcctgctcg tcgagtgggc acaggacgcc aaggctgccg   1860
gtactgcgga tatgttcaat acgctgaagc tgctgaccgt tgtcatgtgg ctcggctacc   1920
ccatcgtgtg ggcactcggc gttgagggca tcgccgttct tccggtcgga gtcacgtcgt   1980
ggggatacag cttcctcgac atcgtcgcga agtacatctt cgcgttcctg ctgctcaact   2040
acctcacgtc gaacgagagc gtcgtctccg gctcgatact cgacgtgccg tccgcgtcgg   2100
gcactcccgc tgacgacgaa ttcggaggcg gaggtggagc tagcaaagga gaagaactct   2160
tcactgagt tggagttgtc ccaattcttg ttgaattaga tggtgatgtt aacggccaca   2220
agttctctgt cagtggagag ggtgaaggtg atgcaacata cggaaaactt accctgaagt   2280
tcatctgcac tactggcaaa ctgcctgttc catggccaac actagtcact actctgtgct   2340
atggtgttca atgcttttca agatacccgg atcatatgaa acggcatgac ttttttcaaga   2400
gtgccatgcc cgaaggttat gtacaggaaa ggaccatctt cttcaaagat gacggcaact   2460
acaagacacg tgctgaagtc aagtttgaag gtgataccct tgttaataga atcgagttaa   2520
aaggtattga cttcaaggaa gatggcaaca ttctgggaca caattggaa tacaactata   2580
actcacacaa tgtatacatc atggcagaca acaaaagaa tggaatcaaa gtgaacttca   2640
agacccgcca caacattgaa gatggaagcg ttcaactagc agaccattat caacaaaata   2700
ctccaattgg cgatggccct gtccttttac cagacaacca ttacctgtcc acacaatctg   2760
ccctttcgaa agatcccaac gaaaagagag accacatggt ccttcttgag tttgtaacag   2820
ctgctgggat tacacatggc atggatgaac tgtacaacca gtctcagccc atcctgaaca   2880
ctaaggagat ggcccctcag agtaaacccc ctgaggaact ggaaatgagc tccatgccat   2940
ctccagtggc tcctctgcca gctaggaccg agggcgtgat tgacatgaga agcatgtcta   3000
gtatcgatag cttcatttcc tgcgccaccg acttccccga agctacaagg ttttaactcg   3060
agtctagacg tggtaccgat aatcaacctc tggattacaa aatttgtgaa agattgactg   3120
gtattcttaa ctatgttgct ccttttacgc tatgtggata cgctgcttta atgcctttgt   3180
atcatgctat tgcttcccgt atggctttca ttttctcctc cttgtataaa tcctggttgc   3240
tgtctcttta tgaggagttg tggcccgttg tcaggcaacg tggcgtggtg tgcactgtgt   3300
ttgctgacgc aacccccact ggttgggca ttgccaccac ctgtcagctc ctttccggga   3360
ctttcgcttt ccccctccct attgccacgg cggaactcat cgccgcctgc cttgcccgct   3420
gctggacagg ggctcggctg ttgggcactg acaattccgt ggtgttgtcg ggaagctga    3480
cgtccttcc atgctgctc gcctgtgttg ccacctggat tctgcgcggg acgtccttct   3540
gctacgtccc ttcggccctc aatccagcgg accttccttc ccgcggcctg ctgccggctc   3600
tgcggcctct tccgcgtctt cgccttcgcc ctcagacgag tcggatctcc ctttgggccg   3660
cctccccgcc tgatgcgggg atcctctaga gtcgagagat ctacgggtgg catccctgtg   3720
```

-continued

```
acccctcccc agtgcctctc ctggccctgg aagttgccac tccagtgccc accagccttg    3780
tcctaataaa attaagttgc atcattttgt ctgactaggt gtccttctat aatattatgg    3840
ggtggagggg ggtggtatgg agcaaggggc aagttgggaa gacaacctgt agggcctgcg    3900
gggtctattg ggaaccaagc tggagtgcag tggcacaatc ttggctcact gcaatctccg    3960
cctcctgggt tcaagcgatt ctcctgcctc agcctcccga gttgttggga ttccaggcat    4020
gcatgaccag gctcagctaa ttttgttt tttggtagag acggggtttc accatattgg    4080
ccaggctggt ctccaactcc taatctcagg tgatctaccc accttggcct cccaaattgc    4140
tgggattaca ggcgtgaacc actgctccct tccctgtcct tctgattttg taggtaacca    4200
cgtgcggacc gagcggccgc aggaacccct agtgatggag ttggccactc cctctctgcg    4260
cgctcgctcg ctcactgagg ccgggcgacc aaaggtcgcc cgacgcccgg gctttgcccg    4320
ggcggcctca gtgagcgagc gagcgcgcag ctgcctgcag g                       4361
```

<210> SEQ ID NO 40
<211> LENGTH: 3647
<212> TYPE: DNA
<213> ORGANISM: Artificial Sequence
<220> FEATURE:
<223> OTHER INFORMATION: 5'-ITR-CAG-HaloR-{Kv2.1Motif}-WPRE-bGHpolyA-ITR- 3'

<400> SEQUENCE: 40

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga ccccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc ccctattga      420 cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc cccaccccca attttgtatt     600
tatttatttt ttaattattt tgtgcagcga tgggggcggg gggggggggg gggcgcgcgc     660
caggcggggc ggggcggggc gaggggcggg gcggggcgag gcggagaggt gcggcggcag     720
ccaatcagag cggcgcgctc cgaaagtttc cttttatggc gaggcggcgg cggcggcggc     780
cctataaaaa gcgaagcgcg cggcgggcgg gagtcgctgc gacgctgcct tcgccccgtg     840
ccccgctccg ccgccgcctc gcgccgcccg ccccggctct gactgaccgc gttactccca     900
caggtgagcg ggcgggacgg cccttctcct ccgggctgta attagcgctt ggtttaatga     960
cggcttgttt cttttctgtg gctgcgtgaa agccttgagg ggctccggga gggccctttg    1020
tgcgggggga gcggctcggg gctgtccgcg ggggacggc tgccttcggg ggggacgggg    1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatgact gagacattgc    1260
caccggtaac ggaatcggct gttgcgctac aggcggaggt gacccagagg gagctgttcg    1320
agttcgttct caacgacccc ctcctcgcca gttcgctgta tattaatatc gcactggcag    1380
```

```
ggctgtcgat actgctttc gtgttcatga cgcgcggact cgacgaccca cgggcgaaac    1440
tcatcgccgt ttcgacgatt ttggtgccgg tggtctctat cgcgagctac accggccttg    1500
catcggggct caccatcagc gtcctcgaga tgccagccgg ccacttcgcc gagggggtcct   1560 cggtgatgct cggcggcgaa gaggtagacg cgtcgtgac gatgtggggc cgctatctga    1620
cgtgggccct ttcgacaccg atgatactgc tggcgcttgg gctgcttgct ggctctaacg    1680
ccacgaagct ctttaccgcc atcaccttcg acatcgcgat gtgtgtcacc ggcctcgcag    1740
ccgcgctgac gacctcttcg cacctgatgc ggtggttctg gtacgccatc agttgtgcgt    1800
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcggaggcg gaggtggagc tagccagtct cagcccatcc    2160
tgaacactaa ggagatggcc cctcagagta accccctga ggaactggaa atgagctcca    2220
tgccatctcc agtggctcct ctgccagcta ggaccgaggg cgtgattgac atgagaagca    2280
tgtctagtat cgatagcttc atttcctgcg ccaccgactt ccccgaagct acaaggtttt    2340
aactcgagtc tagacgtggt accgataatc aacctctgga ttacaaaatt tgtgaaagat    2400
tgactggtat tcttaactat gttgctcctt ttacgctatg tggatacgct gctttaatgc    2460
ctttgtatca tgctattgct tcccgtatgg ctttcatttt ctcctccttg tataaatcct    2520
ggttgctgtc tcttttatgag gagttgtggc ccgttgtcag gcaacgtggc gtggtgtgca    2580
ctgtgtttgc tgacgcaacc cccactggtt ggggcattgc caccacctgt cagctccttt    2640
ccgggacttt cgctttcccc ctccctattg ccacggcgga actcatcgcc gcctgccttg    2700
cccgctgctg gacaggggct cggctgttgg gcactgacaa ttccgtggtg ttgtcgggga    2760
agctgacgtc ctttccatgg ctgctcgcct gtgttgccac ctggattctg cgcgggacgt    2820
ccttctgcta cgtcccttcg gccctcaatc cagcggacct tccttcccgc ggcctgctgc    2880
cggctctgcg gcctcttccg cgtcttcgcc ttcgccctca gacgagtcgg atctcccttt    2940
gggccgcctc cccgcctgat gcggggatcc tctagagtcg agatctac gggtggcatc    3000 cctgtgaccc ctccccagtg cctctcctgg ccctggaagt tgccactcca gtgcccacca    3060
gccttgtcct aataaaatta agttgcatca ttttgtctga ctaggtgtcc ttctataata    3120
ttatggggtg agggggggtg gtatggagca agggggcaagt tgggaagaca acctgtaggg    3180
cctgcgggct ctattgggaa ccaagctgga gtgcagtggc acaatcttgg ctcactgcaa    3240
tctccgcctc ctgggttcaa gcgattctcc tgcctcagcc tcccgagttg ttgggattcc    3300
aggcatgcat gaccaggctc agctaatttt tgttttttg gtagagacgg ggtttcacca    3360
tattggccag gctggtctcc aactcctaat ctcaggtgat ctacccacct tggcctccca    3420
aattgctggg attacaggcg tgaaccactg ctcccttccc tgtccttctg attttgtagg    3480
taaccacgtg cggaccgagc ggccgcagga acccctagtg atggagttgg ccactccctc    3540
tctgcgcgct cgctcgctca ctgaggccgg gcgaccaaag gtcgcccgac gcccgggctt    3600
tgcccgggcg gcctcagtga gcgagcgagc gcgcagctgc ctgcagg              3647
```

<210> SEQ ID NO 41
<211> LENGTH: 4247

<212> TYPE: DNA
<213> ORGANISM: Artificial Sequence
<220> FEATURE:
<223> OTHER INFORMATION: 5'-ITR-CAG-HaloR-GFP-{Nav1.6 Motif}-WPRE-bGHpolyA-ITR- 3'

<400> SEQUENCE: 41

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgatat cctagttatt aatagtaatc    180
aattacgggg tcattagttc atagcccata tatggagttc cgcgttacat aacttacggt     240
aaatggcccg cctggctgac cgcccaacga ccccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc cccctattga    420
cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct cccccccctc cccaccccca attttgtatt    600
tatttatttt ttaattattt tgtgcagcga tgggggcggg gggggggggg gggcgcgcgc    660
caggcggggc ggggcggggc gagggggcggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg gcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatgact gagacattgc   1260
caccggtaac ggaatcggct gttgcgctac aggcggaggt gacccagagg gagctgttcg   1320
agttcgttct caacgacccc ctcctcgcca gttcgctgta tattaatatc gcactggcag   1380
ggctgtcgat actgcttttc gtgttcatga cgcgcggact cgacgaccca cgggcgaaac   1440
tcatcgccgt ttcgacgatt ttggtgccgg tggtctctat cgcgagctac accggccttg   1500
catcggggct caccatcagc gtcctcgaga tgccagccgg ccacttcgcc gagggggtcct  1560
cggtgatgct cggcggcgaa gaggtagacg gcgtcgtgac gatgtggggc cgctatctga   1620
cgtgggccct ttcgacaccg atgatactgc tggcgcttgg gctgcttgct ggctctaacg   1680
ccacgaagct ctttaccgcc atcaccttcg acatcgcgat gtgtgtcacc ggcctcgcag   1740
ccgcgctgac gacctcttcg cacctgatgc ggtggttctg gtacgccatc agttgtgcgt   1800
gtttcctcgt cgtcctctac atcctgctcg tcgagtgggc acaggacgcc aaggctgccg   1860
gtactgcgga tatgttcaat acgctgaagc tgctgaccgt tgtcatgtgg ctcggctacc   1920
ccatcgtgtg ggcactcggc gttgagggca tcgccgttct tccggtcgga gtcacgtcgt   1980
ggggatacag cttcctcgac atcgtcgcga agtacatctt cgcgttcctg ctgctcaact   2040
acctcacgtc gaacgagagc gtcgtctccg gctcgatact cgacgtgccg tccgcgtcgg   2100
gcactcccgc tgacgacgaa ttcggaggcg gaggtggagc tagcaaagga gaagaactct   2160
```

```
tcactggagt tggagttgtc ccaattcttg ttgaattaga tggtgatgtt aacggccaca   2220
agttctctgt cagtggagag ggtgaaggtg atgcaacata cggaaaactt accctgaagt   2280
tcatctgcac tactggcaaa ctgcctgttc catggccaac actagtcact actctgtgct   2340
atggtgttca atgcttttca agatacccgg atcatatgaa acggcatgac ttttcaaga   2400 gtgccatgcc cgaaggttat gtacaggaaa ggaccatctt cttcaaagat dacggcaact   2460
acaagacacg tgctgaagtc aagtttgaag gtgataccct tgttaataga atcgagttaa   2520
aaggtattga cttcaaggaa gatggcaaca ttctgggaca caaattggaa tacaactata   2580
actcacacaa tgtatacatc atggcagaca acaaaagaa tggaatcaaa gtgaacttca   2640
agacccgcca caacattgaa gatggaagcg ttcaactagc agaccattat caacaaaata   2700
ctccaattgg cgatggccct gtccttttac cagacaacca ttacctgtcc acacaatctg   2760 cccttcgaa agatcccaac gaaagagag accacatggt ccttcttgag tttgtaacag   2820
ctgctgggat tacacatggc atggatgaac tgtacaacac cgtgagggtg cccatcgccg   2880
tgggcgagag cgacttcgag aacctgaaca ccgaggacgt gagcagcgag agcgaccct   2940 aactcgagtc tagacgtggt accgataatc aacctctgga ttacaaaatt tgtgaaagat   3000
tgactggtat tcttaactat gttgctcctt ttacgctatg tggatacgct gctttaatgc   3060
ctttgtatca tgctattgct tcccgtatgg ctttcatttt ctcctccttg tataaatcct   3120
ggttgctgtc tctttatgag gagttgtggc ccgttgtcag gcaacgtggc gtggtgtgca   3180
ctgtgtttgc tgacgcaacc cccactggtt ggggcattgc caccacctgt cagctccttt   3240
ccgggacttt cgctttcccc ctccctattg ccacggcgga actcatcgcc gcctgccttg   3300
cccgctgctg gacaggggct cggctgttgg gcactgacaa ttccgtggtg ttgtcgggga   3360
agctgacgtc ctttccatgg ctgctcgcct gtgttgccac ctggattctg cgcgggacgt   3420
ccttctgcta cgtcccttcg gccctcaatc cagcggacct tccttcccgc ggcctgctgc   3480
cggctctgcg gcctcttccg cgtcttcgcc ttcgccctca gacgagtcgg atctcccttt   3540
gggccgcctc cccgcctgat gcggggatcc tctagagtcg agatctac gggtggcatc   3600 cctgtgaccc ctccccagtg cctctcctgg ccctggaagt tgccactcca gtgcccacca   3660
gccttgtcct aataaaatta agttgcatca ttttgtctga ctaggtgtcc ttctataata   3720
ttatggggtg gagggggtg gtatgagca aggggcaagt tgggaagaca acctgtaggg   3780 cctgcgggt ctattgggaa ccaagctgga gtgcagtggc acaatcttgg ctcactgcaa   3840
tctccgcctc ctgggttcaa gcgattctcc tgcctcagcc tcccgagttg ttgggattcc   3900
aggcatgcat gaccaggctc agctaatttt tgttttttg gtagagacgg ggtttcacca   3960
tattggccag gctggtctcc aactcctaat ctcaggtgat ctacccacct tggcctccca   4020
aattgctggg attacaggcg tgaaccactg ctcccttccc tgtccttctg attttgtagg   4080
taaccacgtg cggaccgagc ggccgcagga accctagtg atggagttgg ccactccctc   4140
tctgcgcgct cgctcgctca ctgaggccgg gcgaccaaag gtcgcccgac gcccgggctt   4200
tgcccgggcg gccgcagtga gcgagcgagc gcgcagctgc ctgcagg       4247
```

<210> SEQ ID NO 42
<211> LENGTH: 3533
<212> TYPE: DNA
<213> ORGANISM: Artificial Sequence
<220> FEATURE:
<223> OTHER INFORMATION: 5'- ITR-CAG-HaloR-{Nav1.6 Motif}-WPRE-bGHpolyA-
     ITR- 3'

<400> SEQUENCE: 42

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtgatat cctagttatt aatagtaatc   180
aattacgggg tcattagttc atagcccata tatggagttc cgcgttacat aacttacggt   240
aaatggcccg cctggctgac cgcccaacga cccccgccca ttgacgtcaa taatgacgta   300
tgttcccata gtaacgccaa tagggacttt ccattgacgt caatgggtgg agtatttacg   360
gtaaactgcc cacttggcag tacatcaagt gtatcatatg ccaagtacgc cccctattga   420
cgtcaatgac ggtaaatggc ccgcctggca ttatgcccag tacatgacct tatgggactt   480
tcctacttgg cagtacatct acgtattagt catcgctatt accatgcatg gtcgaggtga   540
gccccacgtt ctgcttcact ctccccatct cccccccctc ccacccccca attttgtatt   600
tatttatttt ttaattattt tgtgcagcga tggggcggg ggggggggg gggcgcgcgc   660
caggcggggc gggcggggc gaggggcggg gcggggcgag gcggagaggt gcggcggcag   720
ccaatcagag cggcgcgctc cgaaagtttc cttttatggc gaggcggcgg cggcggcggc   780
cctataaaaa gcgaagcgcg cggcgggcgg gagtcgctgc gacgctgcct tcgccccgtg   840
ccccgctccg ccgccgcctc gcgccgcccg ccccggctct gactgaccgc gttactccca   900
caggtgagcg gcgggacgg cccttctcct ccgggctgta attagcgctt ggtttaatga   960
cggcttgttt cttttctgtg gctgcgtgaa agccttgagg ggctccggga gggccctttg  1020
tgcgggggga gcggctcggg gctgtccgcg gggggacggc tgccttcggg ggggacgggg  1080
cagggcgggg ttcggcttct ggcgtgtgac cggcggctct agcagcctct gctaaccatg  1140
ttcatgcctt cttcttttc ctacagctcc tgggcaacgt gctggttatt gtgctgtctc  1200
atcattttgg caaagaatta agcttgagct cgcgatccgc agccatgact gagacattgc  1260
caccggtaac ggaatcggct gttgcgctac aggcggaggt gacccagagg gagctgttcg  1320
agttcgttct caacgacccc ctcctcgcca gttcgctgta tattaatatc gcactggcag  1380
ggctgtcgat actgcttttc gtgttcatga cgcgcggact cgacgaccca cgggcgaaac  1440
tcatcgccgt ttcgacgatt ttggtgccgg tggtctctat cgcgagctac accggccttg  1500
catcggggct caccatcagc gtcctcgaga tgccagccgg ccacttcgcc gaggggtcct  1560
cggtgatgct cggcggcgaa gaggtagacg gcgtcgtgac gatgtgggc cgctatctga  1620
cgtgggccct ttcgacaccg atgatactgc tggcgcttgg gctgcttgct ggctctaacg  1680
ccacgaagct cttaccgcc atcaccttcg acatcgcgat gtgtgtcacc ggcctcgcag  1740
ccgcgctgac gacctcttcg cacctgatgc ggtggttctg gtacgccatc agttgtgcgt  1800
gtttcctcgt cgtcctctac atcctgctcg tcgagtgggc acaggacgcc aaggctgccg  1860
gtactgcgga tatgttcaat acgctgaagc tgctgaccgt tgtcatgtgg ctcggctacc  1920
ccatcgtgtg ggcactcggc gttgagggca tcgccgttct tccggtcgga gtcacgtcgt  1980
ggggatacag cttcctcgac atcgtcgcga agtacatctt cgcgttcctg ctgctcaact  2040
acctcacgtc gaacgagagc gtcgtctccg gctcgatact cgacgtgccg tccgcgtcgg  2100
gcactcccgc tgacgacgaa ttcggaggcg gaggtggagc tagcaccgtg agggtgccca  2160
tcgccgtggg cgagagcgac ttcgagaacc tgaacaccga ggacgtgagc agcgagagcg  2220
accccctaact cgagtctaga cgtggtaccg ataatcaacc tctggattac aaaatttgtg  2280
```

| | |
|---|---|
| aaagattgac tggtattctt aactatgttg ctccttttac gctatgtgga tacgctgctt | 2340 |
| taatgccttt gtatcatgct attgcttccc gtatggcttt cattttctcc tccttgtata | 2400 |
| aatcctggtt gctgtctctt tatgaggagt tgtggcccgt tgtcaggcaa cgtggcgtgg | 2460 |
| tgtgcactgt gtttgctgac gcaaccccca ctggttgggg cattgccacc acctgtcagc | 2520 |
| tcctttccgg gactttcgct ttccccctcc ctattgccac ggcggaactc atcgccgcct | 2580 |
| gccttgcccg ctgctggaca gggctcggc tgttgggcac tgacaattcc gtggtgttgt | 2640 |
| cggggaagct gacgtccttt ccatggctgc tcgcctgtgt tgccacctgg attctgcgcg | 2700 |
| ggacgtcctt ctgctacgtc ccttcggccc tcaatccagc ggaccttcct tcccgcggcc | 2760 |
| tgctgccggc tctgcggcct cttccgcgtc ttcgccttcg ccctcagacg agtcggatct | 2820 |
| ccctttgggc cgcctccccg cctgatgcgg ggatcctcta gagtcgagag atctacgggt | 2880 |
| ggcatccctg tgacccctcc ccagtgcctc tcctggccct ggaagttgcc actccagtgc | 2940 |
| ccaccagcct tgtcctaata aaattaagtt gcatcatttt gtctgactag gtgtccttct | 3000 |
| ataatattat ggggtggagg ggggtggtat ggagcaaggg gcaagttggg aagacaacct | 3060 |
| gtagggcctg cggggtctat tgggaaccaa gctggagtgc agtggcacaa tcttggctca | 3120 |
| ctgcaatctc cgcctcctgg gttcaagcga ttctcctgcc tcagcctccc gagttgttgg | 3180 |
| gattccaggc atgcatgacc aggctcagct aattttgtt tttttggtag agacggggtt | 3240 |
| tcaccatatt ggccaggctg gtctccaact cctaatctca ggtgatctac ccaccttggc | 3300 |
| ctcccaaatt gctgggatta caggcgtgaa ccactgctcc cttccctgtc cttctgattt | 3360 |
| tgtaggtaac cacgtgcgga ccgagcgcc gcaggaaccc ctagtgatgg agttggccac | 3420 |
| tccctctctg cgcgctcgct cgctcactga ggccgggcga ccaaaggtcg cccgacgccc | 3480 |
| gggctttgcc cggggcggcct cagtgagcga gcgagcgcgc agctgcctgc agg | 3533 |

<210> SEQ ID NO 43
<211> LENGTH: 4262
<212> TYPE: DNA
<213> ORGANISM: Artificial Sequence
<220> FEATURE:
<223> OTHER INFORMATION: 5' -ITR-CAG-HaloR-GFP-{NLG-1 Motif}-WPRE-
      bGHpolyA-ITR- 3'

<400> SEQUENCE: 43

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgatat cctagttatt aatagtaatc | 180 |
| aattacgggg tcattagttc atagcccata tatggagttc cgcgttacat aacttacggt | 240 |
| aaatggcccg cctggctgac cgcccaacga cccccgccca ttgacgtcaa taatgacgta | 300 |
| tgttcccata gtaacgccaa tagggacttt ccattgacgt caatgggtgg agtatttacg | 360 |
| gtaaactgcc cacttggcag tacatcaagt gtatcatatg ccaagtacgc cccctattga | 420 |
| cgtcaatgac ggtaaatggc ccgcctggca ttatgcccag tacatgacct tatgggactt | 480 |
| tcctacttgg cagtacatct acgtattagt catcgctatt accatgcatg gtcgaggtga | 540 |
| gccccacgtt ctgcttcact ctccccatct ccccccctc cccaccccca attttgtatt | 600 |
| tatttatttt ttaattattt tgtgcagcga tgggggcggg gggggggggg gggcgcgcgc | 660 |
| caggcggggc gggcggggc gaggggcggg gcggggcgag gcgagaggt gcggcggcag | 720 |
| ccaatcagag cggcgcgctc cgaaagtttc cttttatggc gaggcggcgg cggcggcggc | 780 |

```
cctataaaaa gcgaagcgcg cggcgggcgg gagtcgctgc gacgctgcct tcgcccgtg    840
ccccgctccg ccgccgcctc gcgccgcccg cccggctct gactgaccgc gttactccca    900
caggtgagcg gcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatgact gagacattgc   1260
caccggtaac ggaatcggct gttgcgctac aggcggaggt gacccagagg gagctgttcg   1320
agttcgttct caacgacccc ctcctcgcca gttcgctgta tattaatatc gcactggcag   1380
ggctgtcgat actgcttttc gtgttcatga cgcgcggact cgacgaccca cgggcgaaac   1440
tcatcgccgt ttcgacgatt ttggtgccgg tggtctctat cgcgagctac accggccttg   1500
catcggggct caccatcagc gtcctcgaga tgccagccgg ccacttcgcc gagggggtcct  1560
cggtgatgct cggcggcgaa gaggtagacg gcgtcgtgac gatgtggggc cgctatctga   1620
cgtgggccct ttcgacaccg atgatactgc tggcgcttgg gctgcttgct ggctctaacg   1680
ccacgaagct cttaccgcc atcaccttcg acatcgcgat gtgtgtcacc ggcctcgcag    1740
ccgcgctgac gacctcttcg cacctgatgc ggtggtctg gtacgccatc agttgtgcgt    1800
gtttcctcgt cgtcctctac atcctgctcg tcgagtgggc acaggacgcc aaggctgccg   1860
gtactgcgga tatgttcaat acgctgaagc tgctgaccgt tgtcatgtgg ctcggctacc   1920
ccatcgtgtg ggcactcggc gttgagggca tcgccgttct tccggtcgga gtcacgtcgt   1980
ggggatacag cttcctcgac atcgtcgcga agtacatctt cgcgttcctg ctgctcaact   2040
acctcacgtc gaacgagagc gtcgtctccg gctcgatact cgacgtgccg tccgcgtcgg   2100
gcactcccgc tgacgacgaa ttcggaggcg gaggtggagc tagcaaagga gaagaactct   2160
tcactggagt tggagttgtc ccaattcttg ttgaattaga tggtgatgtt aacggccaca   2220
agttctctgt cagtggagag ggtgaaggtg atgcaacata cggaaaactt accctgaagt   2280
tcatctgcac tactggcaaa ctgcctgttc catggccaac actagtcact actctgtgct   2340
atggtgttca atgcttttca agatacccgg atcatatgaa acggcatgac ttttcaaga    2400
gtgccatgcc cgaaggttat gtacaggaaa ggaccatctt cttcaaagat gacggcaact   2460
acaagacacg tgctgaagtc aagtttgaag gtgataccct tgttaataga atcgagttaa   2520
aaggtattga cttcaaggaa gatggcaaca ttctgggaca caaattggaa tacaactata   2580
actcacacaa tgtatacatc atggcagaca aacaaaagaa tggaatcaaa gtgaacttca   2640
agacccgcca caacattgaa gatggaagcg ttcaactagc agaccattat caacaaaata   2700
ctccaattgg cgatggccct gtccttttac cagacaacca ttacctgtcc acacaatctg   2760
cccttttcgaa agatcccaac gaaaagagag accacatggt ccttcttgag tttgtaacag   2820
ctgctgggat tacacatggc atggatgaac tgtacaacgt ggttcttcgg accgcctgtc   2880
ccccagatta cacactagct atgaggaggt cacctgatga tgttccctta atgacaccca   2940
acaccattac aatgtaactc gagtctagac gtggtaccga taatcaacct ctggattaca   3000
aaatttgtga agattgact ggtattctta actatgttgc tccttttacg ctatgtggat    3060
acgctgcttt aatgcctttg tatcatgcta ttgcttcccg tatggctttc attttctcct   3120
ccttgtataa atcctggttg ctgtctcttt atgaggagtt gtggcccgtt gtcaggcaac   3180
```

```
gtggcgtggt gtgcactgtg tttgctgacg caacccccac tggttggggc attgccacca    3240
cctgtcagct cctttccggg actttcgctt tccccctccc tattgccacg gcggaactca    3300
tcgccgcctg ccttgcccgc tgctggacag gggctcggct gttgggcact gacaattccg    3360
tggtgttgtc ggggaagctg acgtcctttc catggctgct cgcctgtgtt gccacctgga    3420
ttctgcgcgg gacgtccttc tgctacgtcc cttcggccct caatccagcg gaccttcctt    3480
cccgcggcct gctgccggct ctgcggcctc ttccgcgtct tcgccttcgc ctcagacga     3540
gtcggatctc cctttgggcc gcctccccgc ctgatgcggg gatcctctag agtcgagaga    3600
tctacggggtg gcatccctgt gacccctccc cagtgcctct cctggccctg gaagttgcca   3660
ctccagtgcc caccagcctt gtcctaataa aattaagttg catcattttg tctgactagg    3720
tgtccttcta taatattatg gggtggaggg ggtggtatg gagcaagggg caagttggga     3780
agacaacctg tagggcctgc ggggtctatt gggaaccaag ctggagtgca gtggcacaat    3840
cttggctcac tgcaatctcc gcctcctggg ttcaagcgat tctcctgcct cagcctcccg    3900
agttgttggg attccaggca tgcatgacca ggctcagcta ttttttgttt ttttggtaga    3960
gacgggtttc accatattg gccaggctgg tctccaactc ctaatctcag gtgatctacc      4020
caccttggcc tcccaaattg ctgggattac aggcgtgaac cactgctccc ttccctgtcc    4080
ttctgatttt gtaggtaacc acgtgcggac cgagcggccg caggaacccc tagtgatgga    4140
gttggccact ccctctctgc gcgctcgctc gctcactgag gccgggcgac caaaggtcgc    4200
ccgacgcccg ggctttgccc gggcggcctc agtgagcgag cgagcgcgca gctgcctgca    4260
gg                                                                    4262

<210> SEQ ID NO 44
<211> LENGTH: 3626
<212> TYPE: DNA
<213> ORGANISM: Artificial Sequence
<220> FEATURE:
<223> OTHER INFORMATION: 5'-ITR-CAG-HaloR-{NLG-1 Motif}-WPRE-bGHpolyA-
      ITR- 3'

<400> SEQUENCE: 44
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac tagggttcc tgcggccgca cgcgtgatat cctagttatt aatagtaatc     180
aattacgggg tcattagttc atagcccata tatggagttc cgcgttacat aacttacggt    240
aaatggcccg cctggctgac cgcccaacga ccccgccca ttgacgtcaa taatgacgta     300
tgttcccata gtaacgccaa tagggacttt ccattgacgt caatgggtgg agtatttacg    360
gtaaactgcc cacttggcag tacatcaagt gtatcatatg ccaagtacgc ccctattga     420
cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct ccccccctc cccaccccca tttgtatt       600
tattttt taattattt tgtgcagcga tgggggcggg ggggggggg gggcgcgcgc          660
caggcgggc ggggcggggc gaggggcggg gcggggcgag gcgagaggt gcggcggcag       720
ccaatcagag cggcgcgctc cgaaagttc cttttatggc gaggcggcgg cggcggcggc     780
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
```

```
caggtgagcg ggcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatgact gagacattgc   1260
caccggtaac ggaatcggct gttgcgctac aggcggaggt gacccagagg gagctgttcg   1320
agttcgttct caacgacccc ctcctcgcca gttcgctgta tattaatatc gcactggcag   1380
ggctgtcgat actgcttttc gtgttcatga cgcgcggact cgacgaccca cgggcgaaac   1440
tcatcgccgt ttcgacgatt ttggtgccgg tggtctctat cgcgagctac accgccttg    1500
catcggggct caccatcagc gtcctcgaga tgccagccgg ccacttcgcc gagggtcct    1560
cggtgatgct cggcggcgaa gaggtagacg gcgtcgtgac gatgtggggc cgctatctga   1620
cgtgggccct ttcgacaccg atgatactgc tggcgcttgg gctgcttgct ggctctaacg   1680
ccacgaagct ctttaccgcc atcaccttcg acatcgcgat gtgtgtcacc ggcctcgcag   1740
ccgcgctgac gacctcttcg cacctgatgc ggtggttctg gtacgccatc agttgtgcgt   1800
gtttcctcgt cgtcctctac atcctgctcg tcgagtgggc acaggacgcc aaggctgccg   1860
gtactgcgga tatgttcaat acgctgaagc tgctgaccgt tgtcatgtgg ctcggctacc   1920
ccatcgtgtg ggcactcggc gttgagggca tcgccgttct tccggtcgga gtcacgtcgt   1980
ggggatacag cttcctcgac atcgtcgcga agtacatctt cgcgttcctg ctgctcaact   2040
acctcacgtc gaacgagagc gtcgtctccg gctcgatact cgacgtgccg tccgcgtcgg   2100
gcactcccgc tgacgacgaa ttcggaggcg gaggtggagc tagcgtggtt cttcggaccg   2160
cctgtccccc aaaaaagagg ctcctgagct tcagggacgt ggacttcgag gaggacagcg   2220
attacacact agctatgagg aggtcacctg atgatgttcc cttaatgaca cccaacacca   2280
ttacaatgta actcgagtct agacgtggta ccgataatca acctctggat tacaaaattt   2340
gtgaaagatt gactggtatt cttaactatg ttgctccttt tacgctatgt ggatacgctg   2400
ctttaatgcc tttgtatcat gctattgctt cccgtatggc tttcattttc tcctccttgt   2460
ataaatcctg gttgctgtct ctttatgagg agttgtggcc cgttgtcagg caacgtggcg   2520
tggtgtgcac tgtgtttgct gacgcaaccc ccactggttg gggcattgcc accacctgtc   2580
agctcctttc cgggactttc gctttccccc tccctattgc cacggcggaa ctcatcgccg   2640
cctgccttgc ccgctgctgg acaggggctc ggctgttggg cactgacaat tccgtggtgt   2700
tgtcggggaa gctgacgtcc tttccatggc tgctcgcctg tgttgccacc tggattctgc   2760
gcgggacgtc cttctgctac gtcccttcgg ccctcaatcc agcggacctt ccttcccgcg   2820
gcctgctgcc ggctctgcgg cctcttccgc gtcttcgcct tcgccctcag acgagtcgga   2880
tctcccttg ggccgcctcc ccgcctgatg cggggatcct ctagagtcga gatctacg     2940
ggtggcatcc ctgtgacccc tccccagtgc ctctcctggc cctggaagtt gccactccag   3000
tgcccaccag ccttgtccta ataaaattaa gttgcatcat tttgtctgac taggtgtcct   3060
tctataatat tatggggtgg aggggggtgg tatggagcaa ggggcaagtt gggaagacaa   3120
cctgtagggc ctgcggggtc tattgggaac caagctggag tgcagtggca caatcttggc   3180
tcactgcaat ctccgcctcc tgggttcaag cgattctcct gcctcagcct cccgagttgt   3240
```

-continued

| | |
|---|---|
| tgggattcca ggcatgcatg accaggctca gctaattttt gttttttttgg tagagacggg | 3300 |
| gtttcaccat attggccagg ctggtctcca actcctaatc tcaggtgatc tacccacctt | 3360 |
| ggcctcccaa attgctggga ttacaggcgt gaaccactgc tcccttccct gtccttctga | 3420 |
| ttttgtaggt aaccacgtgc ggaccgagcg gccgcaggga aaccacgtgc ggaccgagcg | 3480 |
| gccgcaggaa ccccctagtga tggagttggc cactccctct ctgcgcgctc gctcgctcac | 3540 |
| tgaggccggg cgaccaaagg tcgcccgacg cccgggcttt gcccgggcgg cctcagtgag | 3600 |
| cgagcgagcg cgcagctgcc tgcagg | 3626 |

<210> SEQ ID NO 45
<211> LENGTH: 4244
<212> TYPE: DNA
<213> ORGANISM: Artificial Sequence
<220> FEATURE:
<223> OTHER INFORMATION: 5'-ITR-CAG-HaloR-GFP-{MLPH Motif}-WPRE-bGHpolyA-ITR- 3'

<400> SEQUENCE: 45

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgatat cctagttatt aatagtaatc | 180 |
| aattacgggg tcattagttc atagcccata tatggagttc cgcgttacat aacttacggt | 240 |
| aaatggcccg cctggctgac cgcccaacga ccccccgccca ttgacgtcaa taatgacgta | 300 |
| tgttcccata gtaacgccaa tagggacttt ccattgacgt caatgggtgg agtatttacg | 360 |
| gtaaactgcc cacttggcag tacatcaagt gtatcatatg ccaagtacgc ccccctattga | 420 |
| cgtcaatgac ggtaaatggc ccgcctggca ttatgcccag tacatgacct tatgggactt | 480 |
| tcctacttgg cagtacatct acgtattagt catcgctatt accatgcatg gtcgaggtga | 540 |
| gccccacgtt ctgcttcact ctccccatct cccccccctc cccaccccca attttgtatt | 600 |
| tatttatttt ttaattattt tgtgcagcga tgggggcggg ggggggggg gggcgcgcgc | 660 |
| caggcggggc ggggcgggc gaggggcggg gcggggcgag gcggagaggt gcggcggcag | 720 |
| ccaatcagag cggcgcgctc cgaaagtttc cttttatggc gaggcggcgg cggcggcggc | 780 |
| cctataaaaa gcgaagcgcg cggcgggcgg gagtcgctgc gacgctgcct tcgccccgtg | 840 |
| ccccgctccg ccgccgcctc gcgccgcccg cccccggctct gactgaccgc gttactccca | 900 |
| caggtgagcg gcgggacgg cccttctcct ccgggctgta attagcgctt ggtttaatga | 960 |
| cggcttgttt cttttctgtg gctgcgtgaa agccttgagg ggctccggga gggccctttg | 1020 |
| tgcgggggga gcggctcggg gctgtccgcg ggggacggc tgccttcggg ggggacgggg | 1080 |
| cagggcgggg ttcggcttct ggcgtgtgac cggcggctct agcagcctct gctaaccatg | 1140 |
| ttcatgcctt cttcttttc ctacagctcc tgggcaacgt gctggttatt gtgctgtctc | 1200 |
| atcattttgg caaagaatta agcttgagct cgcgatccgc agccatgact gagacattgc | 1260 |
| caccggtaac ggaatcggct gttgcgctac aggcggaggt gacccagagg gagctgttcg | 1320 |
| agttcgttct caacgacccc ctcctcgcca gttcgctgta tattaatatc gcactggcag | 1380 |
| ggctgtcgat actgctttc gtgttcatga cgcgcggact cgacgaccca cgggcgaaac | 1440 |
| tcatcgccgt ttcgacgatt ttggtgccgg tggtctctat cgcgagctac accggccttg | 1500 |
| catcggggct caccatcagc gtcctcgaga tgccagccgg ccacttcgcc gagggggtcct | 1560 |
| cggtgatgct cggcggcgaa gaggtagacg gcgtcgtgac gatgtgggc cgctatctga | 1620 |

```
cgtgggccct ttcgacaccg atgatactgc tggcgcttgg gctgcttgct ggctctaacg    1680
ccacgaagct ctttaccgcc atcaccttcg acatcgcgat gtgtgtcacc ggcctcgcag    1740
ccgcgctgac gacctcttcg cacctgatgc ggtggttctg gtacgccatc agttgtgcgt    1800
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcggaggcg gaggtggagc tagcaaagga gaagaactct    2160
tcactggagt tggagttgtc ccaattcttg ttgaattaga tggtgatgtt aacggccaca    2220
agttctctgt cagtggagag ggtgaaggtg atgcaacata cggaaaactt accctgaagt    2280
tcatctgcac tactggcaaa ctgcctgttc catggccaac actagtcact actctgtgct    2340
atggtgttca atgcttttca agatacccgg atcatatgaa acggcatgac ttttcaaga    2400 gtgccatgcc cgaaggttat gtacaggaaa ggaccatctt cttcaaagat gacggcaact    2460
acaagacacg tgctgaagtc aagtttgaag gtgataccct tgttaataga atcgagttaa    2520
aaggtattga cttcaaggaa gatggcaaca ttctgggaca caaattggaa tacaactata    2580
actcacacaa tgtatacatc atggcagaca acaaaagaa tggaatcaaa gtgaacttca    2640
agacccgcca acacattgaa gatggaagcg ttcaactagc agaccattat caacaaaata    2700
ctccaattgg cgatggccct gtccttttac cagacaacca ttacctgtcc acacaatctg    2760 cccttcgaa agatcccaac gaaaagagag accacatggt ccttcttgag tttgtaacag    2820
ctgctgggat tacacatggc atggatgaac tgtacaacag gaccagcct ctgaacagca    2880 aaaagaaaaa gaggctcctg agcttcaggg acgtggactt cgaggaggac agcgactaac    2940
tcgagtctag acgtggtacc gataatcaac ctctggatta caaaatttgt gaaagattga    3000
ctggtattct taactatgtt gctcctttta cgctatgtgg atacgctgct ttaatgcctt    3060
tgtatcatgc tattgcttcc cgtatggctt tcattttctc ctccttgtat aaatcctggt    3120
tgctgtctct ttatgaggag ttgtggcccg ttgtcaggca acgtggcgtg gtgtgcactg    3180
tgtttgctga cgcaaccccc actggttggg gcattgccac cacctgtcag ctcctttccg    3240
ggactttcgc tttccccctc cctattgcca cggcggaact catcgccgcc tgccttgccc    3300
gctgctggac aggggctcgg ctgttgggca ctgacaattc cgtggtgttg tcggggaagc    3360
tgacgtcctt tccatggctg ctcgcctgtg ttgccacctg gattctgcgc gggacgtcct    3420
tctgctacgt cccttcggcc ctcaatccag cggaccttcc ttcccgcggc ctgctgccgg    3480
ctctgcggcc tcttccgcgt cttcgccttc gccctcagac gagtcggatc tccctttggg    3540
ccgcctcccc gcctgatgcg gggatcctct agagtcgaga gatctacggg tggcatccct    3600
gtgacccctc cccagtgcct ctcctggccc tggaagttgc cactccagtg cccaccagcc    3660
ttgtcctaat aaaattaagt tgcatcattt tgtctgacta ggtgtccttc tataatatta    3720
tggggtggag gggggtggta tggagcaagg ggcaagttgg gaagacaacc tgtagggcct    3780
gcggggtcta ttgggaacca agctggagtg cagtggcaca atcttggctc actgcaatct    3840
ccgcctcctg ggttcaagcg attctcctgc ctcagcctcc cgagttgttg ggattccagg    3900
catgcatgac caggctcagc taattttgt ttttttggta gagacggggt ttcaccatat    3960
tggccaggct ggtctccaac tcctaatctc aggtgatcta cccaccttgg cctcccaaat    4020
```

| | | |
|---|---|---|
| tgctgggatt acaggcgtga accactgctc ccttccctgt ccttctgatt ttgtaggtaa | 4080 | |
| ccacgtgcgg accgagcggc cgcaggaacc cctagtgatg gagttggcca ctccctctct | 4140 | |
| gcgcgctcgc tcgctcactg aggccgggcg accaaaggtc gcccgacgcc cgggctttgc | 4200 | |
| ccgggcggcc tcagtgagcg agcgagcgcg cagctgcctg cagg | 4244 | |

<210> SEQ ID NO 46
<211> LENGTH: 3530
<212> TYPE: DNA
<213> ORGANISM: Artificial Sequence
<220> FEATURE:
<223> OTHER INFORMATION: 5'-ITR-CAG-HaloR-{MLPH Motif}-WPRE-bGHpoly
A-ITR- 3'

<400> SEQUENCE: 46

| | | |
|---|---|---|
| cctgcaggca gctgcgcgct cgctcgctca ctgaggccgc ccgggcaaag cccgggcgtc | 60 | |
| gggcgacctt tggtcgcccg gcctcagtga gcgagcgagc gcgcagagag ggagtggcca | 120 | |
| actccatcac tagggggttcc tgcggccgca cgcgtgatat cctagttatt aatagtaatc | 180 | |
| aattacgggg tcattagttc atagcccata tatggagttc cgcgttacat aacttacggt | 240 | |
| aaatggcccg cctggctgac cgcccaacga ccccccgccca ttgacgtcaa taatgacgta | 300 | |
| tgttcccata gtaacgccaa tagggacttt ccattgacgt caatgggtgg agtatttacg | 360 | |
| gtaaactgcc cacttggcag tacatcaagt gtatcatatg ccaagtacgc cccctattga | 420 | |
| cgtcaatgac ggtaaatggc ccgcctggca ttatgcccag tacatgacct tatgggactt | 480 | |
| tcctacttgg cagtacatct acgtattagt catcgctatt accatgcatg gtcgaggtga | 540 | |
| gccccacgtt ctgcttcact ctccccatct ccccccccctc cccacccccca attttgtatt | 600 | |
| tatttatttt ttaattattt tgtgcagcga tggggcggg ggggggggg gggcgcgcgc | 660 | |
| caggcggggc ggggcggggc gaggggcggg gcggggcgag gcggagaggt gcggcggcag | 720 | |
| ccaatcagag cggcgcgctc cgaaagtttc cttttatggc gaggcggcgg cggcggcggc | 780 | |
| cctataaaaa gcgaagcgcg cggcgggcgg gagtcgctgc gacgctgcct tcgccccgtg | 840 | |
| ccccgctccg ccgccgcctc gcgccgcccg ccccggctct gactgaccgc gttactccca | 900 | |
| caggtgagcg ggcgggacgg cccttctcct ccgggctgta attagcgctt ggtttaatga | 960 | |
| cggcttgttt cttttctgtg gctgcgtgaa agccttgagg ggctccggga gggccctttg | 1020 | |
| tgcgggggga gcggctcggg gctgtccgcg gggggacggc tgccttcggg ggggacgggg | 1080 | |
| cagggcgggg ttcggcttct ggcgtgtgac cggcggctct agcagcctct gctaaccatg | 1140 | |
| ttcatgcctt cttcttttttc ctacagctcc tgggcaacgt gctggttatt gtgctgtctc | 1200 | |
| atcattttgg caaagaatta agcttgagct cgcgatccgc agccatgact gagacattgc | 1260 | |
| caccggtaac ggaatcggct gttgcgctac aggcggaggt gacccagagg gagctgttcg | 1320 | |
| agttcgttct caacgacccc ctcctcgcca gttcgctgta tattaatatc gcactggcag | 1380 | |
| ggctgtcgat actgcttttc gtgttcatga gcgcgcggact cgacgaccca cgggcgaaac | 1440 | |
| tcatcgccgt ttcgacgatt ttggtgccgg tggtctctat gcgcgagcta accggccttg | 1500 | |
| catcggggct caccatcagc gtcctcgaga tgccagccgg ccacttcgcc gaggggtcct | 1560 | |
| cggtgatgct cggcggcgaa gaggtagacg gcgtcgtgac gatgtggggc cgctatctga | 1620 | |
| cgtgggccct ttcgacaccg atgatactgc tggcgcttgg gctgcttgct ggctctaacg | 1680 | |
| ccacgaagct ctttaccgcc atcacctccg acatgcgcgat gtgtgtcacc ggcctcgcag | 1740 | |
| ccgcgctgac gacctcttcg cacctgatgc ggtggttctg gtacgccatc agttgtgcgt | 1800 | |

```
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcggaggcg gaggtggagc tagcagggac cagcctctga    2160
acagcaaaaa gaaaagagg ctcctgagct tcagggacgt ggacttcgag gaggacagcg     2220
actaactcga gtctagacgt ggtaccgata atcaacctct ggattacaaa atttgtgaaa    2280
gattgactgg tattcttaac tatgttgctc cttttacgct atgtggatac gctgctttaa    2340
tgcctttgta tcatgctatt gcttccgta tggctttcat tttctcctcc ttgtataaat     2400
cctggttgct gtctctttat gaggagttgt ggcccgttgt caggcaacgt ggcgtggtgt    2460
gcactgtgtt tgctgacgca accccactg gttggggcat tgccaccacc tgtcagctcc     2520
tttccgggac tttcgctttc cccctcccta ttgccacggc ggaactcatc gccgcctgcc    2580
ttgcccgctg ctggacaggg gctcggctgt tgggcactga caattccgtg gtgttgtcgg    2640
ggaagctgac gtcctttcca tggctgctcg cctgtgttgc cacctggatt ctgcgcggga    2700
cgtccttctg ctacgtccct tcggccctca atccagcgga ccttccttcc cgcggcctgc    2760
tgccggctct gcggcctctt ccgcgtcttc gccttcgccc tcagacgagt cggatctccc    2820
tttgggccgc ctccccgcct gatgcgggga tcctctagag tcgagagatc tacgggtggc    2880
atccctgtga ccctccccca gtgcctctcc tggccctgga agttgccact ccagtgccca    2940
ccagccttgt cctaataaaa ttaagttgca tcattttgtc tgactaggtg tccttctata    3000
atattatggg gtggaggggg gtggtatgga gcaaggggca agttgggaag acaacctgta    3060
gggcctgcgg ggtctattgg gaaccaagct ggagtgcagt ggcacaatct tggctcactg    3120
caatctccgc ctcctgggtt caagcgattc tcctgcctca gcctcccgag ttgttgggat    3180
tccaggcatg catgaccagg ctcagctaat ttttgttttt ttggtagaga cggggtttca    3240
ccatattggc caggctggtc tccaactcct aatctcaggt gatctaccca ccttggcctc    3300
ccaaattgct gggattacag gcgtgaacca ctgctccctt ccctgtcctt ctgattttgt    3360
aggtaaccac gtgcggaccg agcggccgca ggaacccta gtgatggagt tggccactcc     3420
ctctctgcgc gctcgctcgc tcactgaggc cgggcgacca aaggtcgccc gacgcccggg    3480
ctttgcccgg gcggcctcag tgagcgagcg agcgcgcagc tgcctgcagg                3530
```

AAV-MEDIATED SUBCELLULAR TARGETING OF HETEROLOGOUS RHODOPSINS IN RETINAL GANGLION CELLS

CROSS-REFERENCE TO RELATED APPLICATIONS

This application is a continuation of and claims priority to U.S. patent application Ser. No. 15/978,290, filed on May 14, 2018, which is a continuation of and claims priority to U.S. patent application Ser. No. 15/236,152, filed on Aug. 12, 2016, now U.S. Pat. No. 9,968,689, issued on May 15, 2018, which is a continuation of and claims priority to U.S. patent application Ser. No. 13/696,252, filed on Jun. 12, 2013, now U.S. Pat. No. 9,453,241, issued on Sep. 27, 2016, which is a national stage and claims priority to PCT Appl. No. PCT/US11/35266, filed on May 4, 2011, which claims the benefit of priority of U.S. Provisional Appl. No. 61/331,125, filed on May 4, 2010, the contents of which are hereby incorporated by reference in their entirety.

STATEMENT OF RIGHTS TO INVENTIONS MADE UNDER FEDERALLY SPONSORED RESEARCH

This invention was funded in part by grants (R01EY017130, P30EY040689) from the National Eye Institute of the National Institutes of Health, which provides to the United States government certain rights in this invention.

SEQUENCE LISTING

The instant application contains a Sequence Listing which has been submitted electronically as a text file, created on Jan. 22, 2025, named 6065.0505C3_SequenceListing.txt, and about 118 kilobytes in size. The sequence listing is hereby incorporated by reference.

BACKGROUND OF THE INVENTION

Field of the Invention

The present invention in the field of molecular biology and medicine relates to the targeting of microbial-type rhodopsins, such as the light-gated cation-selective membrane channel, channelrhodopsin-2 (Chop2 or ChR2) or the ion pump halorhodopsin (HaloR) in retinal ganglion cells as a basis for restoring visual perception and various aspects of vision.

Description of the Background Art

Vision normally begins when rods and cones (photoreceptors) convert light signals to electrical signals that are then relayed through second- and third-order retinal neurons and the optic nerve to the lateral geniculate nucleus and, then to the visual cortex where visual images are formed (Baylor, D, 1996, Proc. Natl. Acad. Sci. USA 93:560-565; Wässle, H, 2004, Nat. Rev. Neurosci. 5:747-57). The severe loss of photoreceptor cells can be caused by congenital retinal degenerative diseases, such as retinitis pigmentosa (RP) (Sung, C H et al., 1991, Proc. Natl. Acad. Sci. USA 88:6481-85; Humphries, P et al., 1992, Science 256:804-8; Welcher, R G et al., in: S J Ryan, Ed, Retina, Mosby, St. Louis (1994), pp. 335-466), and can result in complete blindness. Age-related macular degeneration (AMD) also results from degeneration and death of photoreceptor cells, which can cause severe visual impairment within the centrally located best visual area of the visual field.

As rods and cones are lost in humans as well as rodents and other animals, little or no signal is sent to the brain. There are currently no effective treatments or cures for inherited retinal degenerations that cause partial or total blindness.

Approaches to treatment of retinal degeneration include (1) preservation of remaining photoreceptors in patients with retinal degenerative disease, and (2) replacement of photoreceptors lost to retinal degeneration. For the first approach, neuroprotection with neurotrophic factors (LaVail, M M et al., 1992, Proc. Natl. Acad. Sci. USA 89:11249-53) and virus-vector-based delivery of wild-type genes for recessive null mutations (Acland, G M et al., 2001, Nat. Genet. 28:92-95) have come the furthest—to the point of clinical trials (Hauswirth, W W, 2005, Retina 25, S60; Jacobson, S, Protocol #0410-677, for adeno-associated viral (AAV)-mediated gene replacement therapy in Leber's Congenital Amaurosis (LCA), a specific form of retinal degeneration. This approach is not applicable in patients in advanced stages of retinal degeneration where photoreceptor cells must be replaced. One replacement approach involves transplantation of normal tissue or cells to the diseased retina. Another involves electrical-stimulation of remaining light-insensitive neurons via retinal implants in lieu of the lost cells (prosthetic substitution). Both methods face many obstacles. Hence, there is a continuing need for vision-restoring therapies for inherited blinding disease.

Histological studies in animal models of photoreceptor degeneration and in postmortem human eyes from patients with almost complete photoreceptor loss due to RP showed preservation of a significant number of inner retinal neurons, making retinal gene therapy a possible therapeutic option (e.g., U.S. Pat. No. 5,827,702; WO 00/15822 (2000) and WO 98/48097 (1998)).

Retinal gene transfer of a reporter gene, green fluorescent protein (GFP), using a recombinant AAV (rAAV) was demonstrated in normal primates (Bennett, J et al. 1999 Proc. Natl. Acad. Sci. USA 96, 9920-25). However, the restoration of vision in a blinding disease of animals, particularly in humans and other mammals, caused by genetic defects in retinal pigment epithelium (RPE) and/or photoreceptor cells has not been achieved. Bennett and colleagues have described rescue of photoreceptors by gene therapy in a mutant RPE65 gene model of rapid degeneration of photoreceptors and replacement therapy with the normal gene to replace/supplant the mutant gene. (US Pat Publ 2004/0022766, Acland et al.). This therapy showed some success in a naturally-occurring dog model of human LCA—the RPE65 mutant dog.

Heterologous expression of Drosophila rhodopsin (Zemelman, B V et al., 2002, Neuron 33:15-22) and melanopsin, the putative photopigment of the intrinsic photosensitive retinal ganglion cells ("RGC") has been reported (Melyan, Z. et al., 2005, Nature 433:741-5; Panda, S. et al., 2005, Science 307:600-604; Qiu, X. et al., 2005, Nature 433:745-9). These photopigments, however, are coupled to membrane channels via a G protein signaling cascade and use cis-isoforms of retinaldehyde as their chromophore. Expression of multiple genes would be required to render photosensitivity and their light response kinetics is rather slow.

The present inventor's work, including the present invention, utilizes microbial-type rhodopsins that are similar to bacteriorhodopsin (Oesterhelt, D et al., 1973, Proc. Natl.

Acad. Sci. USA 70:2853-7), whose conformation change is caused by reversible photoisomerization of their chromophore group, all-trans retinaldehyde, and is directly coupled to ion movement through the membrane (Oesterhelt, D., 1998, *Curr. Opin. Struct. Biol.* 8:489-500). Two microbial-type opsins, channelopsin -1 and -2 (Chop1 and Chop2), have been cloned from *Chlamydomonas reinhardtii* (Nagel, G. et al., 2002, *Science* 296:2395-8; Sineshchekov, O A et al., 2002, *Proc. Natl. Acad. Sci. USA* 99:8689-94; Nagel, G. et al., 2003, *Proc. Natl. Acad. Sci. USA* 100, 13940-45) and shown to form directly light-gated membrane channels when expressed in *Xenopus laevis* oocytes or HEK293 cells in the presence of all-trans retinal. Chop2, a seven transmembrane domain protein, becomes photo-switchable when bound to the chromophore all-trans retinal. Chop2 is particularly attractive because its functional light-sensitive channel, channelrhodopsin-2 (Chop2 retinalidene abbreviated ChR2) with the attached chromophore is permeable to physiological cations. Unlike animal rhodopsins, which only bind the 11-cis conformation, Chop2/ChR2 binds all-trans retinal isomers, obviating the need for all-trans to 13-cis isomerization supplied by the vertebrate visual cycle.

However, the long-term compatibility of expressing ChR2 in native neurons in vivo in general and the properties of ChR2-mediated light responses in retinal neurons in particular remained unknown until the work of the present inventor and colleagues. Indeed their work (and that of others) represent the pioneering demonstration of the (a) feasibility of restoring light sensitivity to a degenerate retina, (b) transmission of light-driven information to higher visual centers, and mediation of visually guided behaviors through such prosthetic interventions. This work proved that the insertion of such "optical neuromodulators" or "light sensors" as ChR2 into normally photo-insensitive retinal neurons is a promising approach for restoring sight to profoundly blind individuals. These strategies included the delivery of the directly photosensitive cation channel ChR2 and the photosensitive chloride pump halorhodopsin (abbreviated herein "HaloR" and elsewhere "NpHR" or "eNpHR" because of its origin from Natronobacterium pharaonis (Lanyi, J K et al. *J. Biol. Chem.* 265:1253-1260 (1990). Such work has been reported by the present inventor's group (Bi, A. et al., Neuron 50:23-33 (2006), Ivanova, E et al., *Mol Vis.* 15:1680-9 (2009), Zhang, Y. et al., *J. Neurosci.* 29:9186-9 (2009), primarily with ChR2. Others have delivered and expressed ChR2 (Lagali et al., *Nat. Neurosci.* 11:667-675 (2008); NpHR by (Busskamp V. et al., *Science* 329,413-417 (2010); synthetically engineered potassium (SPARK) and glutamate (LiGluR) channels (Greenberg, K P et al., *Invest. Ophthalmol. Vis. Sci.* 47, 4750 (2006; abstract); Kolstad et al., *Invest. Ophthalmol. Vis. Sci* 49:3897 (2009; Abstract) and the G protein-coupled receptor melanopsin (Lin, B. et al., *Proc. Natl. Acad. Sci. USA* 105:16009-16014 (2008)) in normally nonphotosensitive bipolar, amacrine, and ganglion cells or nonfunctional photoreceptors.

The present inventor and colleagues (Bi, A. et al., *Neuron* 50:23-33 (2006); WO2007/131180) disclosed adeno-associated virus (AAV2)-mediated expression of exogenously delivered light-gated membrane cation channel, ChR2, or light-driven chloride ion pump, HaloR, in inner retinal neurons and demonstrated that expression of ChR2 in surviving inner retinal neurons of a mouse with photoreceptor degeneration can restore the ability of the retina to encode light signals and transmit the light signals to the visual cortex.

The present inventor and colleagues (Zhang, Y. et al., *J Neurosci.* 29:9186-96 (2009 Jul. 22) reported that the expression HaloR can effectively restore OFF responses in inner retinal neurons of mice with retinal degeneration. HaloR-expressing RGCs respond to light with rapid hypopolarization and suppression of spike activity. After termination of the light stimulus, their membrane potential exhibited a rapid rebound overshoot with robust sustained or transient spike firing. Coexpression of ChR2/HaloR in RGCs produced ON, OFF, and even ON-OFF responses, depending on the wavelength of the light stimulus. Suggesting that the expression of multiple microbial rhodopsins such as ChR2 and HaloR is a possible strategy to restore both ON and OFF light responses in the retina after the death of rod and cone photoreceptors.

The present invention is a refinement and significant step forward of the inventor's prior work, being directed to differential, subcellular "site-selective expression" of these light-sensor-encoding nucleic acids by adding sorting or targeting motifs to the vectors that confer such selectivity. This adds to the "spatial resolution" of vision restoration achieved in this manner in those suffering vision loss or blindness caused, for example, by any of a number of retinal degenerative diseases. The present inventor's approach does not require, introducing exogenous cells and tissues or physical devices, thus avoiding obstacles encountered by existing approaches, though the combined use of the present approach with visual prostheses or devices is also envisioned.

SUMMARY OF THE INVENTION

The present inventor has discovered that differentially targeted expression of ChR2 and HaloR to different subcellular regions in RGCs recreates the antagonistic center-surround receptive field in these cells that further permits improvement of the visual spatial processing for restored vision. The primary spatial distinction of expression is in center vs. peripheral regions of the cells. Peripheral is also referred to in the art as the "surround" or as "off center," terms that are well understood.

RGCs are rendered light sensitive by expression of ChR2 and/or HaloR selectively in somatodendritic region while being kept to a minimum in the axonal region. This enables maintenance of visual spatial processing. This is based on the discovery that a number of "sorting motifs" also referred to here as "targeting motifs, "sorting sequences" or "targeting sequences" present in a vector that comprises the light sensor encoding nucleic acid. Such a motif mediates site-or region-selective expression of the ChR2 or HaloR in subcellular regions of a retinal neuron, preferably an RGC. This targeting serves as a basis for enhanced spatial control and specificity, and results in transmission of appropriate signals, providing better contrast, which more closely resembling signals from a healthy, intact retina, to higher centers of the visual cortex to compensate for damage and degeneration in retinal photoreceptors.

The present invention is directed to a nucleic acid molecule encoding a rhodopsin for differential expression in subcellular regions of a retinal neuron, preferably an RGC, which molecule comprises:
(a) a first nucleotide sequence encoding a light-gated channel rhodopsin or a light-driven ion pump rhodopsin;
(b) linked in frame to (a), a second nucleotide sequence encoding a peptide or polypeptide sorting motif;

(c) operatively linked to (a) and (b), a promoter sequence, and optionally, transcriptional regulatory sequences; and (d) a polyadenylation sequence preferably from bovine growth hormone (bGHpolyA).

Preferably the nucleic promoter and regulator sequence comprise a cytomegalovirus enhancer/chicken β-actin promoter (CAG), preferably SEQ ID NO:26, and woodchuck hepatitis virus posttranscriptional regulatory element (WPRE), preferably SEQ ID NO:27, and (d) is preferably SEQ ID NO:28.

The nucleic acid molecule may further comprise, linked in frame with (a) and (b), a third nucleotide sequence encoding a reporter polypeptide, preferably GFP; a preferred sequence is SEQ ID NO: 25.

In the above nucleic acid molecule, the light-gated channel rhodopsin is preferably ChR2, such as SEQ ID: 22, or a biologically active fragment, most preferably SEQ ID NO: 22. The light driven ion pump rhodopsin is preferably HaloR, most preferably SEQ ID NO:24.

In one embodiment of the above nucleic acid molecule, the sorting motif is one that targets the center of the neuron's receptive field, for example, to one or more of the following subcellular regions: the soma, the proximal dendritic region, or the axon initial segment. Preferred sorting motif-encoding sequences are a nucleotide sequence encoding (a) voltage-gated potassium channel 2.1 (Kv2.1), which is or comprises SEQ ID NO:1; or (b) the ankyrin binding domain of voltage-gated sodium channel 1.6 (Nav1.6), which is or comprises SEQ ID NO:3. The encoded amino acid sequence of the motif is preferably (a) the sequence of Kv2.1, which is or comprises SEQ ID NO:2; or (b) the sequence of the ankyrin-binding domain of Nav1.6, which is or comprises SEQ ID NO:4.

In another preferred embodiment of the above nucleic acid molecule, the motif is one that targets the rhodopsin (±the reporter gene) to the surround or off-center part of the neuron's receptive field, for example, to the somatodendritic region of the neurons. Preferred sorting motif-encoding sequences are a nucleotide sequence encoding (a) the cytoplasmic C-terminal segment of neuroligin-1 (NLG-1), which is or comprises SEQ ID NO:5; or (b) the myosin binding domain of melanophilin (MLPH), which is or comprises SEQ ID NO:7. The encoded amino acid sequence of the motif is preferably (a) the sequence of the cytoplasmic C-terminal segment of NLG-1 which is or comprises, SEQ ID NO:6; or (b) the sequence of the myosin-binding domain of MLPH, which is or comprises SEQ ID NO:8.

Also provided is a recombinant adeno-associated virus expression vector, preferably an AAV2 vector, comprising any of the above nucleic acid molecules. In the vector, the sequence of the nucleic acid molecule is flanked at its 5' end by a 5' inverted terminal repeat (ITR) and at its 3' end by a 3' ITR of the AAV, preferably AAV2. The sequence of these ITR is preferably SEQ ID NO: 17 and SEQ ID NO:18, respectively.

As above, in one embodiment of the expression vector, the sorting motif is one that targets the center of the neuron's receptive field. A preferred nucleotide sequence encoding the motif is (a) the sequence encoding Kv2.1, which is or comprises SEQ ID NO:1; or (b) the sequence encoding the ankyrin binding domain of Nav1.6, which is or comprises SEQ ID NO:3. Preferably, in the expression vector, the amino acid sequence of the encoded motif is (a) the acid sequence of Kv2.1, which is or comprises SEQ ID NO:3; or (b) the sequence of the ankyrin binding domain of Nav1.6, which is or comprises SEQ ID NO:4.

In another embodiment of the expression vector, the sorting motif is one that targets the surround or off-center of the neuron's receptive field. Here, the motif is selected from the group consisting of nucleotide sequence encoding (a) the cytoplasmic C-terminal segment of NLG-1, which is or comprises SEQ ID NO:5; or (b) myosin binding domain of MLPH, which is or comprises SEQ ID NO: 7. Preferably, in the expression vector, the amino acid sequence of the encoded motif is (a) the sequence of the cytoplasmic C-terminal segment NLG-1, which is or comprises SEQ ID NO:6; or (b) the sequence of the myosin-binding domain of MLPH, which is or comprises SEQ ID NO:8.

The above expression vector can have one of the following schematic structures:

(a) 5'-ITR-CAG-ChR2-GFP-{Motif}-WPRE-bGHpolyA-ITR-3'

(b) 5'-ITR-CAG-ChR2-{Motif}-WPRE-bGHpolyA-ITR-3'

(c) 5'-ITR-CAG-HaloR-GFP-{Motif}-WPRE-bGHpolyA-ITR-3'

(d) 5'-ITR-CAG-HaloR-{Motif}-WPRE-bGHpolyA-ITR-3' wherein {Motif} is nucleotide sequence encoding the sorting motif, and wherein, any two or more of ChR2, GFP and Motif or HaloR, GFP and Motif, are linked in-frame.

In the foregoing, vector, the Motif is preferably selected from the group consisting of (i) the nucleotide sequence encoding Kv2.1, which is or comprises SEQ ID NO:1; or (ii) the nucleotide sequence encoding the ankyrin binding domain of Nav1.6, which is or comprises SEQ ID NO:3

(iii) the nucleotide sequence encoding cytoplasmic C-terminal segment of NLG-1, which is or comprises SEQ ID NO:5; or (iv) the nucleotide sequence encoding myosin binding domain of MLPH, which is or comprises SEQ ID NO:7.

A preferred expression vector for targeting ChR2 to the center of the neuron's receptive field has the schematic structure and nucleotide sequence selected from the following group (a) 5'-ITR-CAG-ChR2-GFP-{Kv2.1 Motif}-WPRE-bGHpolyA-ITR-3', SEQ ID NO:31;

(b) 5'-ITR-CAG-ChR2-{Kv2.1 Motif}-WPRE-bGHpolyA-ITR-3', SEQ ID NO:32;

(c) 5'-ITR-CAG-ChR2-GFP-{Nav2.6 Motif}-WPRE-bGHpolyA-ITR-3', SEQ ID NO:33; and (d) 5'-ITR-CAG-ChR2-{Nav2.6 Motif}-WPRE-bGHpolyA-ITR-3', SEQ ID NO:34.

A preferred expression vector for targeting ChR2 to the surround or off-center of the neuron's receptive field has the schematic structure and nucleotide sequence selected from the following group (a) 5'-ITR-CAG-ChR2-GFP-{NLG-1 Motif}—WPRE-bGHpolyA-ITR-3', SEQ ID NO:35;

(b) 5'-ITR-CAG-ChR2-{NLG-1 Motif}-WPRE-bGHpolyA-ITR-3', SEQ ID NO:36;

(c) 5'-ITR-CAG-ChR2-GFP-{MLPH Motif}-WPRE-bGHpolyA-ITR-3', SEQ ID NO:37, and (d) 5'-ITR-CAG-ChR2-{MLPH Motif}-WPRE-bGHpolyA-ITR-3', SEQ ID NO:38.

A preferred expression vector targeting HaloR to the center of the neuron's receptive field has the schematic structure and nucleotide sequence selected from the following group:

(a) 5'-ITR-CAG-HaloR-GFP-{Kv2.1 Motif}-WPRE-bGHpolyA-ITR-3', SEQ ID NO:39;

(b) 5'-ITR-CAG-HaloR-{Kv2.1 Motif}-WPRE-bGH-polyA-ITR-3', SEQ ID NO:40;
(c) 5'-ITR-CAG-HaloR-{Nav2.6 Motif}—WPRE-bGH-polyA-ITR-3', SEQ ID NO:41; and
(d) 5'-ITR-CAG-HaloR-GFP-{Nav2.6 Motif}-WPRE-bGHpolyA-ITR-3', SEQ ID NO:42;

A preferred expression vector for targeting HaloR to the surround or off-center of the neuron's receptive field has the schematic structure and nucleotide sequence selected from the following group
(a) 5'-ITR-CAG-HaloR-GFP-{NLG-1 Motif}—WPRE-bGHpolyA-ITR-3', SEQ ID NO:43;
(b) 5'-ITR-CAG-HaloR-{NLG-1 Motif}-WPRE-bGH-polyA-ITR-3' SEQ ID NO:44;
(c) 5'-ITR-CAG-HaloR-GFP-{MLPH Motif}-WPRE-bGHpolyA-ITR-3', SEQ ID NO:45; and
(c) 5'-ITR-CAG-HaloR-{MLPH Motif}-WPRE-bGH-polyA-ITR-3', SEQ ID NO:46.

The present invention is directed to a method of restoring light sensitivity to a retina, comprising:
(a) delivering to retinal neuron, preferably an RGC, a nucleic acid expression vector that encodes
  (i) a light-gated channel rhodopsin or a light-driven ion pump rhodopsin;
  (ii) a sorting motif that targets (i) to be expressed in selected subcellular regions of the neurons;
  (iii) optionally, a reporter polypeptide; and
  (iv) operatively linked to (i), (ii) and (iii) a promoter sequence, and optionally, transcriptional regulatory sequences; and
(b) expressing the vector in the neurons,
wherein the expression of the sorting motif with the rhodopsin results in selected expression of the rhodopsin and, when present, the reporter polypeptide, in subcellular regions of the RGC for which the motifs are selective, thereby restoring the light sensitivity.

Also provided is a method of selectively expressing a light-gated channel rhodopsin or a light-driven ion pump rhodopsin in a desired subcellular site or sites of a retinal neuron, preferably an RGC, comprising
a) delivering to the RGC a nucleic acid molecule or expression vector that encodes
  (i) a light-gated channel rhodopsin, preferably ChR2, or a light-driven ion pump rhodopsin, preferably HaloR;
  (ii) a sorting motif that targets the rhodopsin to be expressed in the desired site or sites;
  (iii) operatively linked to (i) and (ii) a promoter sequence, and optionally, transcriptional regulatory sequences; and
(b) expressing the vector in the desired sites of the RGC.

In one embodiment of the method, the desired subcellular site is soma, proximal dendritic region, or axon initial segment, where preferably the motif is one that targets the rhodopsin to the center of the RGCs receptive field.

In another embodiment of the method, the desired subcellular site is the somatodendritic region, where preferably the motif is one that targets the surround or off-center of the RGCs receptive field.

In all the above methods, the nucleic acid molecule comprises any of the molecules above and the vector is the any of expression vectors above.

BRIEF DESCRIPTION OF THE DRAWINGS

Figure 2B:
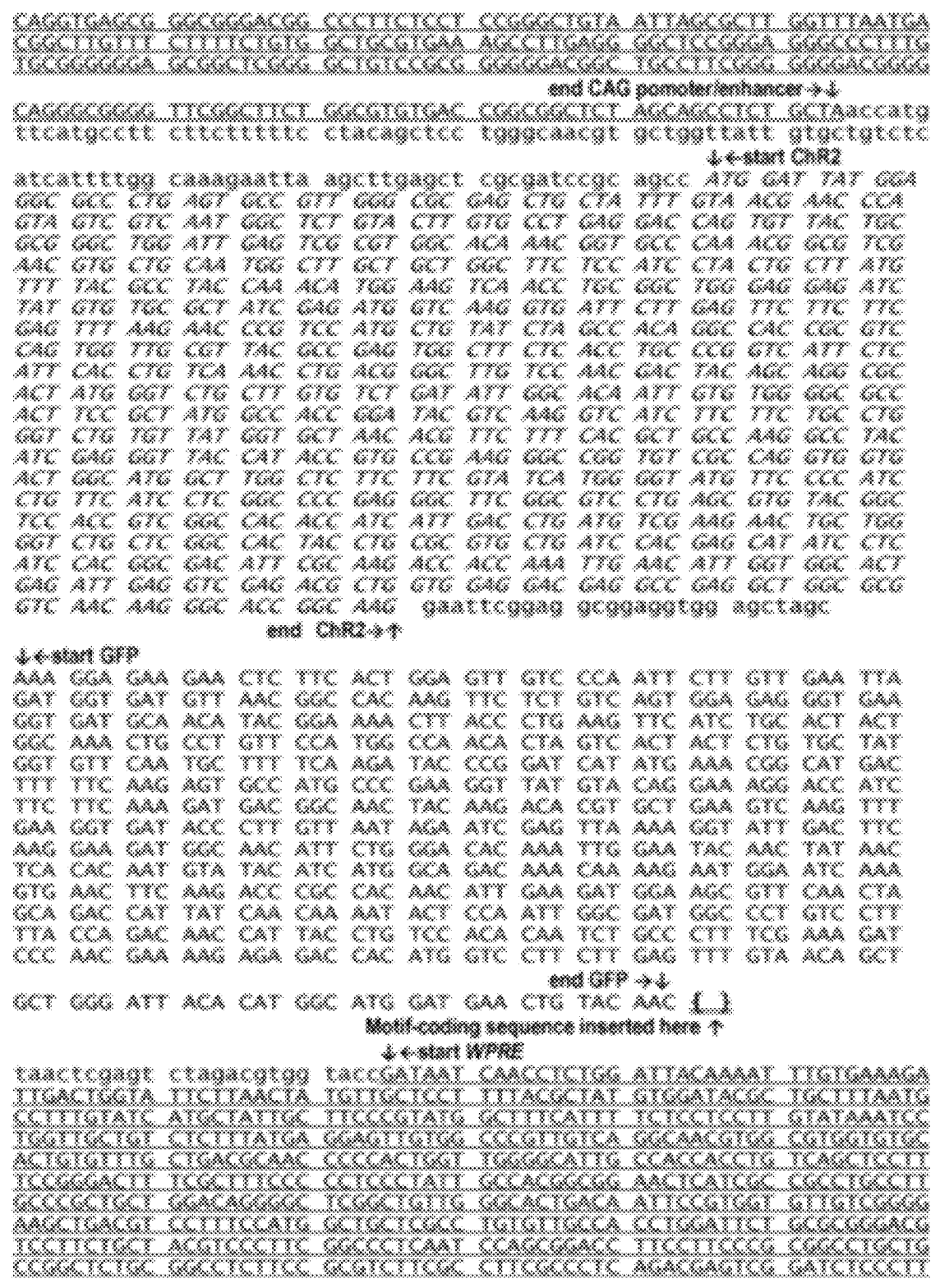

FIGS. 2A-2C shows a schematic of a vector that does not have the Sorting Motif present but is "poised" for insertion of the motif (with the insertion point shown in the sequence). The schematic is followed by a linear vector diagram (SEQ ID NO: 29) ITR-CAG-ChR2-GFP-{insertion site for Sorting Motif}-WPRE-bGHpolyA-ITR' which is annotated as follows:
  ITR's: lower case, bold, italic, underscore
  CAG: UPPERCASE (underscore)
  Chop2/ChR2 (used interchangeably here): UPPERCASE, ITALIC
  GFP: UPPERCASE (nonbold, non-italic)
  Sorting Motif: UPPERCASE (double underscore)
  WPRE: UPPERCASE (underscore)
  bGHpolyA: UPPERCASE (italic)
  intervening vector nucleotides/cloning carryover: lower case (not italic)

FIGS. 3A-3B show a linear vector diagram (SEQ ID NO: 30) annotated as noted above. This vector is the same as the vector depicted in FIG. 2, except without GFP: ITR-CAG-ChR2-{insertion site for Sorting Motif}-WPRE-bGHpolyA-ITR'.

Figure 4B:
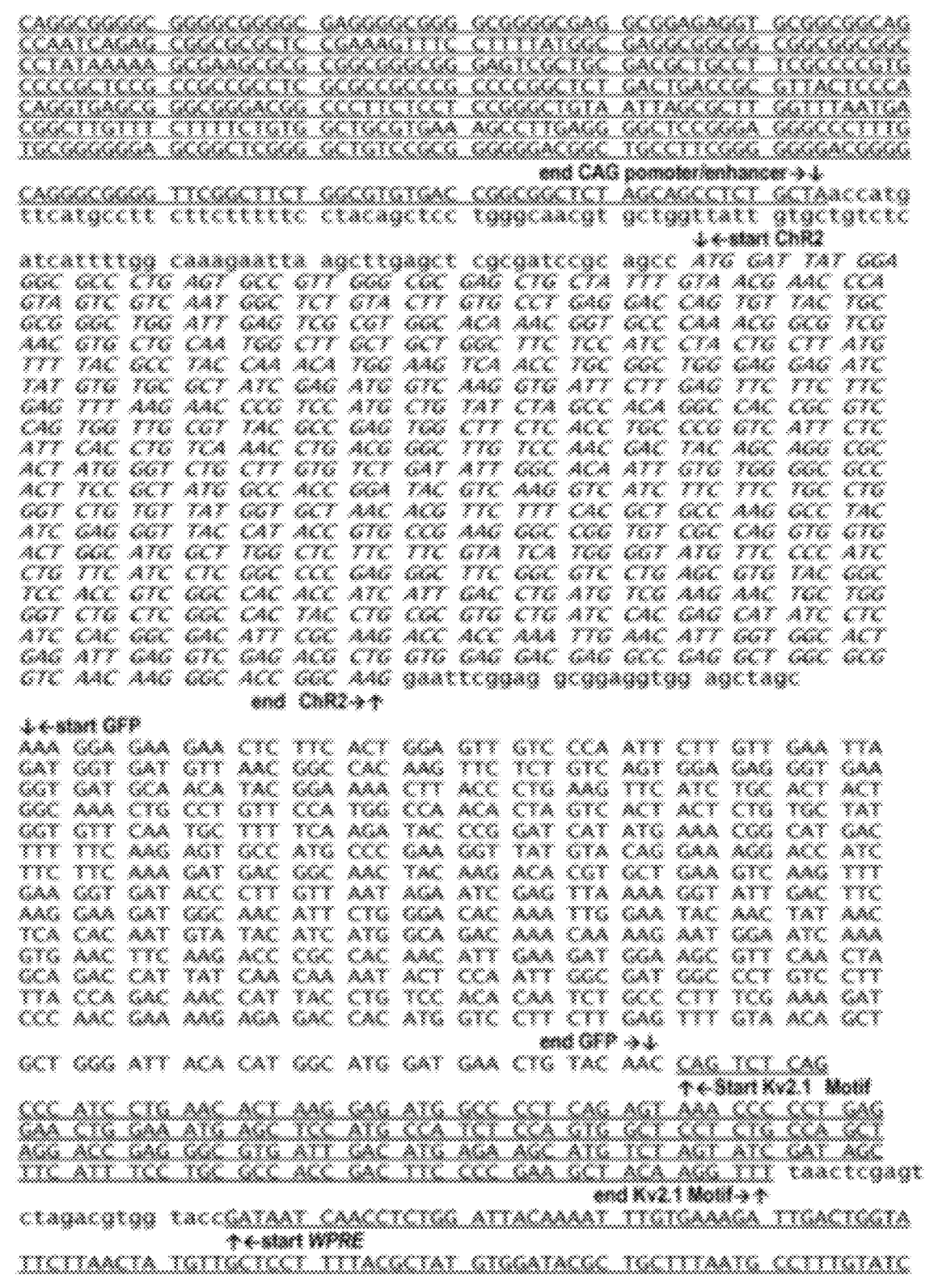

FIGS. 4A-4C shows a schematic followed by an annotated linear vector diagram of the vector represented by SEQ ID NO: 31, 5'-ITR-CAG-ChR2-GFP-{Kv2.1 Motif}-WPRE-bGHpolyA-ITR-3'.

FIGS. 5A-5B shows a schematic followed by an annotated linear vector diagram of the vector represented by SEQ ID NO: 32. This vector is the same as the vector depicted in FIG. 4, except without GFP: 5'-ITR-CAG-ChR2-{Kv2.1 Motif}-WPRE-bGHpolyA-ITR-3'.

Figure 6A:
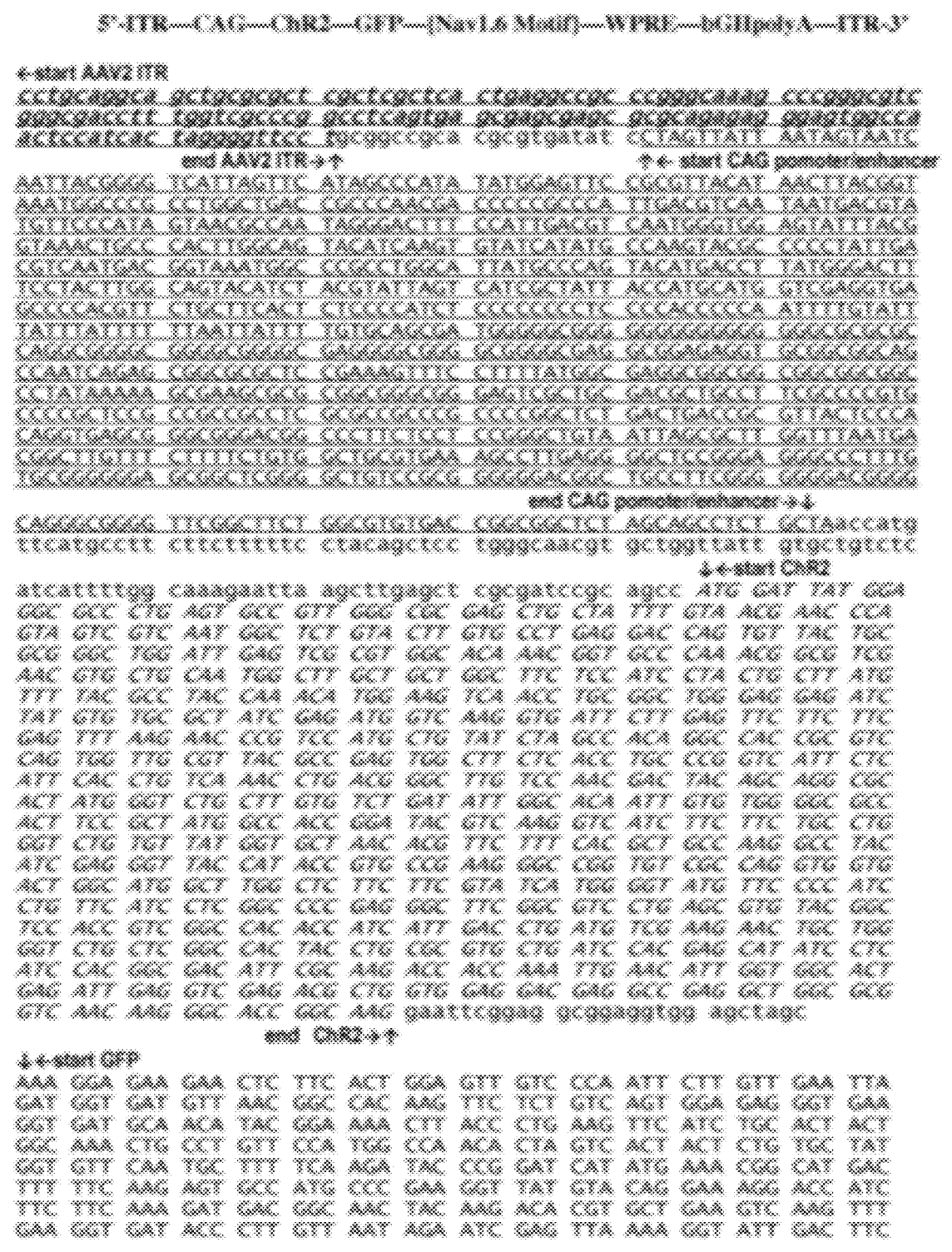

FIGS. 6A-6B shows an annotated linear vector diagram of the vector represented by SEQ ID NO: 33, 5'-ITR-CAG-ChR2-GFP-{Nav1.6 Motif}-WPRE-bGHpolyA-ITR-3'.

Figure 7B:
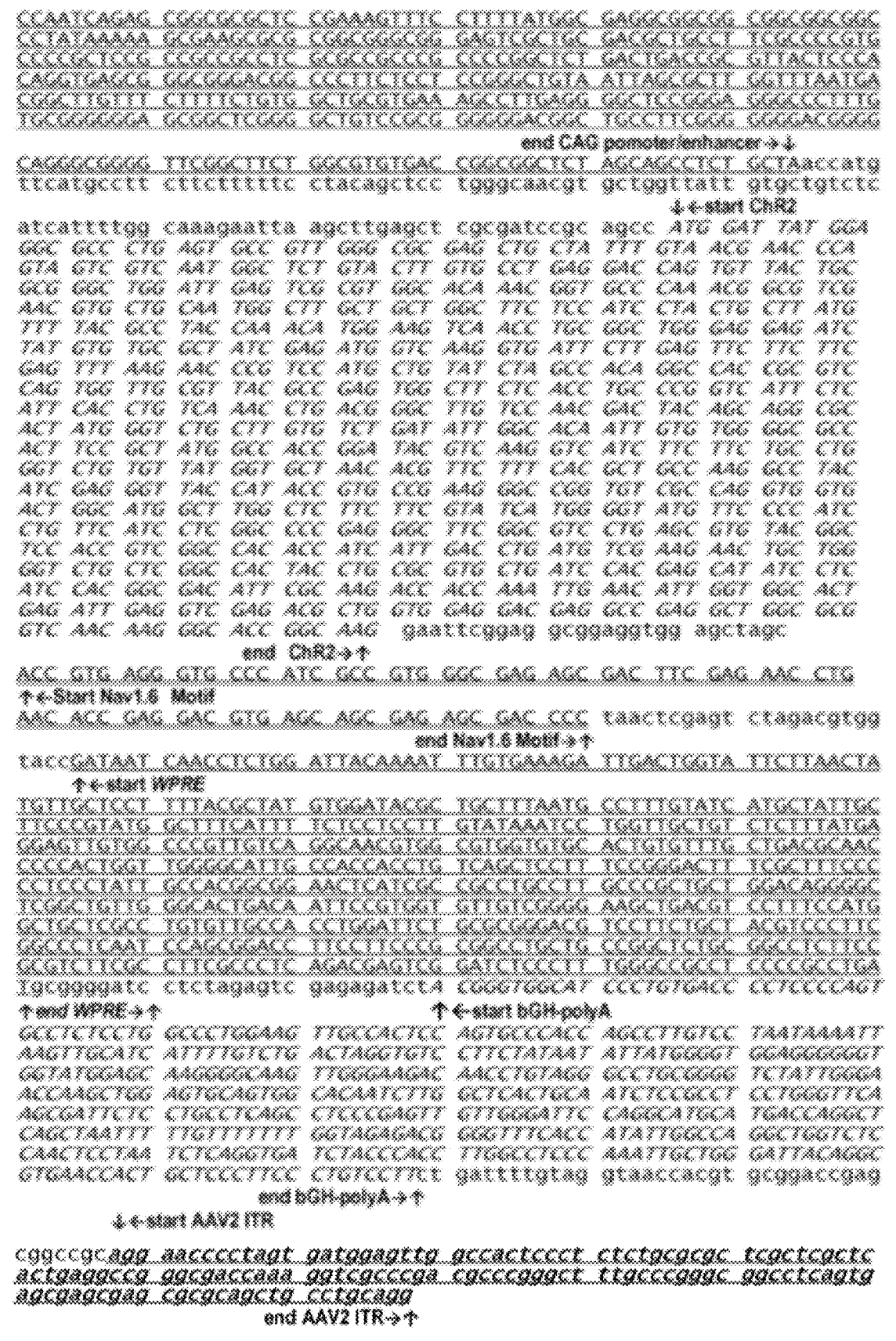

FIGS. 7A-7B shows an annotated linear vector diagram of the vector represented by SEQ ID NO: 34. This vector is the same as the vector depicted in FIG. 6, except without GFP: 5'-ITR-CAG-ChR2-{Nav1.6 Motif}-WPRE-bGHpolyA-ITR-3'.

FIGS. 8A-8B shows an annotated linear vector diagram of the vector represented by SEQ ID NO: 35, 5'-ITR-CAG-ChR2-GFP-{NLG1 Motif}-WPRE-bGHpolyA—ITR-3'.

FIGS. 9A-9B shows an annotated linear vector diagram of the vector represented by SEQ ID NO: 36. This vector is the same as the vector depicted in FIG. 8, except without GFP: 5'-ITR-CAG-ChR2-{NLG1 Motif}-WPRE-bGHpolyA-ITR-3'.

FIGS. 10A-10B shows an annotated linear vector diagram of the vector represented by SEQ ID NO: 37, 5'-ITR-CAG-ChR2-GFP-{MLPH Motif}-WPRE-bGHpolyA-ITR-3'.

FIGS. 11A-11B shows an annotated linear vector diagram of the vector represented by SEQ ID NO: 38. This vector is the same as the vector depicted in FIG. 6A, except without GFP: 5'-ITR-CAG-ChR2-{MLPH Motif}-WPRE-bGHpolyA-ITR-3'.

FIGS. 12A-12B shows a schematic followed by an annotated linear vector diagram of the vector represented by SEQ ID NO: 39, 5'-ITR-CAG-HaloR-GFP-{Kv2.1 Motif}—WPRE-bGHpolyA-ITR-3'.

FIGS. 13A-13B shows a schematic followed by an annotated linear vector diagram of the vector represented by SEQ ID NO: 40. This vector is the same as the vector depicted in FIG. 7A, except without GFP: 5'-ITR-CAG-HaloR-{Kv2.1 Motif}-WPRE-bGHpolyA-ITR-3'.

FIGS. 14A-14C shows an annotated linear vector diagram of the vector represented by SEQ ID NO: 41, 5'-ITR-CAG-HaloR-GFP-{Nav1.6 Motif}-WPRE-bGHpolyA-ITR-3'.

FIGS. 15A-15B shows an annotated linear vector diagram of the vector represented by SEQ ID NO: 42. This vector is the same as the vector depicted in FIG. 8A, except without GFP: 5'-ITR-CAG-HaloR-{Nav1.6 Motif}-WPRE-bGH-polyA-ITR-3'.

FIGS. 16A-16B shows an annotated linear vector diagram of the vector represented by SEQ ID NO: 43, 5'-ITR-CAG-HaloR-GFP-{NGL-1 Motif}-WPRE-bGHpolyA-ITR-3'.

FIGS. 17A-17B shows an annotated linear vector diagram of the vector represented by SEQ ID NO: 44. This vector is the same as the vector depicted in FIG. 9A, except without GFP: 5'-ITR—CAG-HaloR-{NGL-1 Motif}-WPRE-bGHpolyA-ITR-3'.

FIGS. 18A-18B shows an annotated linear vector diagram of the vector represented by SEQ ID NO: 45, 5'-ITR-CAG-HaloR-GFP-{MLPH Motif}-WPRE-bGHpolyA-ITR-3'.

FIGS. 19A-19B shows an annotated linear vector diagram of the vector represented by SEQ ID NO: 46. This vector is the same as the vector depicted in FIG. 10A, except without GFP: 5'-ITR-CAG-HaloR-{MLPH Motif}-WPRE-bGH-polyA-ITR-3'.

DESCRIPTION OF THE PREFERRED EMBODIMENTS

Figure 1:
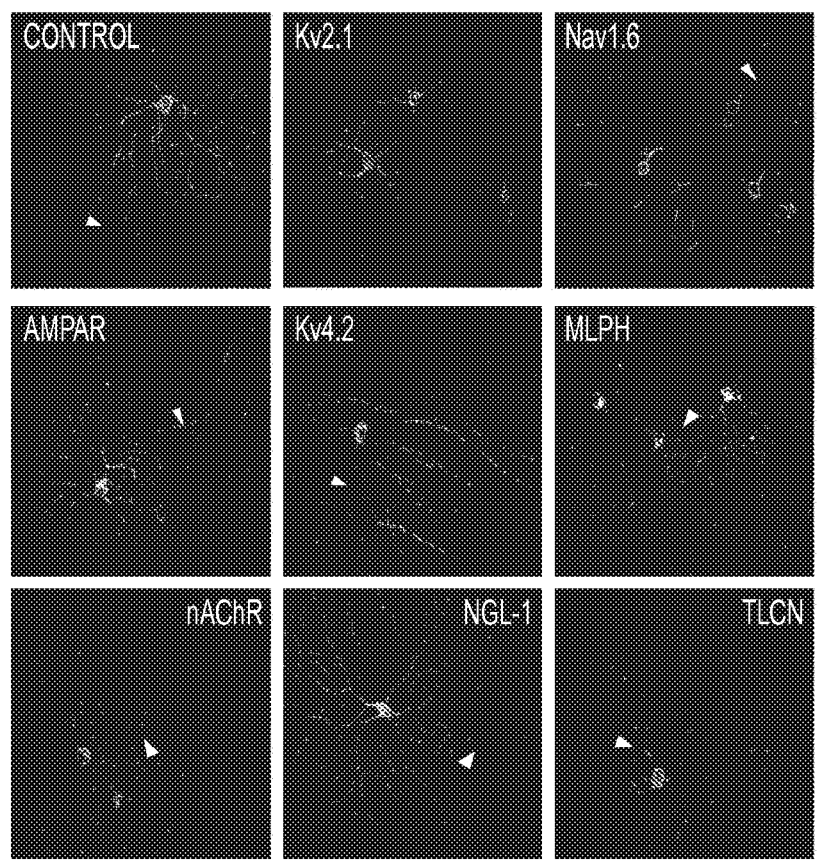
FIG. 1 is a group of photomicrographs comparing fluorescence intensity (originally green, converted to white, on black background) from green fluorescent protein (GFP) encoded in frame with ChR2 with or without (control) a sorting motif. The sorting motifs tested, as indicated in abbreviated form in the panels (described in more detail elsewhere in this document), were: Kv2.1, Nav1.6, AMPAR, Kv4.2, MLPH, nAchR, NGL-1 AND TLCN. The arrowheads in each panel point to the axon of the ChR2-GFP expressing RGCs. The results appear in tabular form in Table 2, below.
Figures 3B, 4A:
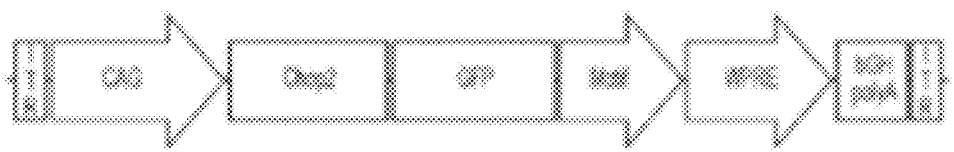
Figures 4C, 5A:
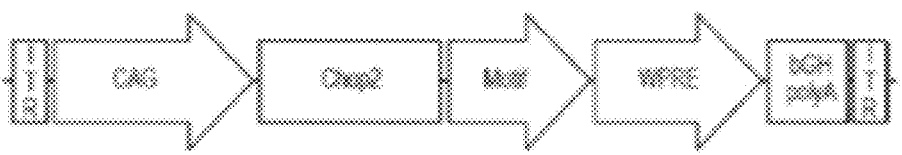

The present inventors discovered that certain protein sorting motifs used in AAV-mediated transduction direct targeted expression of Chop2 or HaloR or, for visualization, a test reporter gene (Green fluorescent protein, GFP) to RGCs results in differential expression of the targeted reporter gene in different compartments or subcellular sites of the RGCs.

The present Examples show differential expression of ubiquitously expressing light sensitive channels, namely ChR2 driven by the CAG promoter and under the influence of various targeting motifs in distinct subcellular regions or sites of retinal ganglion cells.

However, targeting of depolarizing membrane channels, such as ChR2, to the ON-type retinal neurons might result in better useful vision.

In addition, expression of light sensors in more distal retinal neurons, such as bipolar cells, would utilize the remaining signal processing functions of the degenerate retina.

By expressing a depolarizing light sensor, such as ChR2, in ON type retinal neurons (ON type ganglion cells and/or ON type bipolar cells) and expressing a hypopolarizing light sensor, such as HaloR (a chloride pump) (Han, X et al., 2007, PLOS ONE, March 21;2: e299; Zhang, F et al., 2007; Nature 446:633-9; present inventors' results) in OFF type retinal neurons (OFF type ganglion cells and/or OFF type bipolar cells) could create ON and OFF pathways in photoreceptor degenerated retinas.

According to the present invention, the followings approaches used to restore the light sensitivity of inner retinal neurons are enhanced by the use, disclosed herein, of peptide/polypeptide sorting motifs expressed using recombinant vectors in selected subcellular sites/regions of retinal neurons, particularly RGC.

(1) Ubiquitously expressing light sensitive channels, such as ChR2, are employed to produced membrane depolarization in all types of ganglion cells (both ON and OFF ganglion cells), or all types of bipolar cells (rod bipolar cells, and ON and OFF cone bipolar cells). The AAV vector with CAG promoter has already partially achieved this approach in rodent retinas, as exemplified herein.

(2) A depolarizing light sensor, such as ChR2, is targeted to ON type retinal neurons such as ON type ganglion cells or ON type bipolar cells. Fragments of a human gap junctional protein (connexin-36) promoter were found to target GFP in ON-type retinal ganglion cells by using AAV-2 virus vector (Greenberg K P et al., 2007,*ARVO abstract*, 2007). A readily packable shorter version of mGluR6 promoter of (<2.5 kb) would allow targeting of ChR2 to ON type bipolar cells (both rod bipolar cells and ON type cone bipolar cells).

(3) Cell specific promoters are used to target the specific types of retinal neurons. A promoter that could target rod bipolar cells is Pcp2 (L7) promoter (Tomomura, M et al., 2001, *Eur J Neurosci.* 14:57-63). The length of the active promoter is preferably less than 2.5 Kb so it can be packaged into the AAV viral cassette.

(4) A depolarizing light sensor, such as ChR2, is targeted to ON type ganglion cells or ON type cone bipolar cells and a hypopolarizing light sensor, such as halorhodopsin, to OFF type ganglion cells or OFF type cone bipolar cells to create ON and OFF pathways. As described above, an adequately short (packable) version of mGluR6 promoter (<2.5 kb) would allow targeting of ChR2 to ON type bipolar cells. The Neurokinin-3 (NK-3) promoter would be used to target halorhodopsin to OFF cone bipolar cells (Haverkamp, S et al., 2002, *J Compar. Neurol.* 455:463-76.

(5) A depolarizing light sensor, such as ChR2, is targeted to rod bipolar cells and their target AII amacrine cells, an ON type retinal cell (which communicate with ON and OFF cone bipolar cells).

Sorting Motifs

Table 1 describes the sorting peptide/polypeptide motifs examined by the present inventors presenting both the nucleotide and amino acid sequences, and a conclusion about their effects on sorting or targeting of the linked encoded proteins to different subcellular sites.

TABLE 1

Description of Sorting Motifs.

| Name | Source Protein (ref) | Sorting Motif | Subcellular Targeted Site (Receptive Field) |
|---|---|---|---|
| Kv2.1 | Voltage-gated potassium channel 2.1[1] | Cytoplasmic C-terminus | Proximal dendrites, soma (center) |
| | aa sequence: (SEQ ID NO: 2) QSQPILNTKEMAPQSKPPEELEMSSMP SPVAPLPARTEGVIDMRSMSSIDSFIS CATDFPEATRF (65) | nt sequence: (SEQ ID NO: 1) CAG TCT CAG CCC ATC CTG AAC ACT AAG GAG ATG GCC CCT CAG AGT AAA CCC CCT GAG GAA CTG GAA ATG AGC TCC ATG CCA TCT CCA GTG GCT CCT CTG CCA GCT AGG ACC GAG GGC GTG ATT GAC ATG AGA AGC ATG TCT AGT ATC GAT AGC TTC ATT TCC TGC GCC ACC GAC TTC CCC GAA GCT ACA AGG TTT | |
| Nav1.6 | Voltage-gated sodium channel 1.6[2,3] | Ankyrin binding domain | Axon initial segment, soma (center) |
| | aa sequence: (SEQ ID NO: 4) TVRVPIAVGE SDFENLNTED VSSESGP (27) | nt sequence: (SEQ ID NO: 3) ACC GTG AGG GTG CCC ATC GCC GTG GGC GAG AGC GAC TTC GAG AAC CTG AAC ACC GAG GAC GTG AGC AGC GAG GAC CCC | |
| NLG-1 | Neuroligin-1[4] | Cytoplasmic C-terminal | Somatodendrtic (surround = off-center) |
| | aa sequence: (SEQ ID NO: 6) VVLRTACPPDYLTAMRRSPDDVPLMTP NTITM (31) | nt sequence: (SEQ ID NO: 5) GTG GTG CTG AGG ACT GCC TGC CCC CCT GAC TAC ACC CTG GCT ATG AGG AGA AGC CCA GAC GAT GTG CCC CTG ATG ACC CCC AAC ACC ATC ACA ATG | |
| MLPH | Melanophilin[5] | Myosin binding domain | Somatodendritic (surround = off center) |
| | aa sequence: (SEQ ID NO: 8) RDQPLNSKKKKRLLSFRDVDFEEDSD (26) | nt sequence: (SEQ ID NO: 7) AGG GAC CAG CCT CTG AAC AGC AAA AAG AAA AAG AGG CTC CTG AGC TTC AGG GAC GTG GAC TTC GAG GAG GAC AGC GAC | |
| nAchR | Nicotinic acetylcholine receptor α7 subunit[6] | Tyrosine-Dileucine | Somatodendritic (surround = off center) |
| | aa sequence: (SEQ ID NO: 10) GEDKVRPACQHKPRRCALASVELSAGA GPPTSNGNLLYIGFRGLEGM (47) | nt sequence: (SEQ ID NO: 9) GGC GAG GAC AAG GTG CGG CCC GCC TGT CAG CAC AAG CCT CGG CGG TGC AGC CTG GCC AGC GTG GAG CTG AGC GCC GGC GCC GGC CCA CCC ACC AGC AAC GGC AAC CTG CTG TAC ATC GGC TTC AGA GGC CTG GAG GGC ATG | |
| Kv4.2 | Voltage-gated potassium channel 4.2[7] | Dileucine | Somatodendritic (surround = off center) |
| | aa sequence: (SEQ ID NO: 12) FEQQHHHLLH CLEKTT (16) | Nucleotide sequence: (SEQ ID NO: 11) TTC GAG CAG CAG CAC CAC CAC CTG CTG CAC TGC CTG GAG AAG ACC ACC | |
| TLCN | Telencephalin[8] | Phenylalanine-based | Somatodendritic (surround = off center) |
| | aa sequence: (SEQ ID NO: 14) QSTACKKGEYNVQEAESSGEAVCLNGA GGGAGGAAGAEGGPEAAGGAAESPAEG EVFAIQLTSA (65) | Nucleotide sequence: (SEQ ID NO: 13) CAG AGC ACA GCC TGC AAA AAG GGC GAG TAC AAC GTG CAG GAA GCT GAG AGC TCT GGC GAA GCC GTG TGT CTG AAC GGC GCC GGA GGC GGT GCC GGC GGA GCT GCC GGC GCT GAG GGT GGC CCT GAG GCC GCT GGA GGT GCC GCT GAG AGC CCC GCT GAG GGC GAA GTC TTT GCC ATC CAG CTG ACA TCT GCT | |

TABLE 1-continued

Description of Sorting Motifs.

| Name | Source Protein (ref) | Sorting Motif | Subcellular Targeted Site (Receptive Field) |
|------|---------------------|---------------|---------------------------------------------|
| AMPAR | AMPA receptor GluR1 subunit[9]<br>aa sequence: (SEQ ID NO: 16)<br>EFCYKSRSESKRMKGFCLIPQQSINEA<br>IRTSTLPRNSGA (39) | Cytoplasmic C-terminal<br>Nucleotide sequence: (SEQ ID NO: 15)<br>GAG TTC TGC TAC AAG AGC AGG TCC GAA TCT AAG AGA<br>ATG AAA GGC TTT TGT CTG ATC CCC CAG CAG AGC ATC<br>AAC GAG GCC ATT CGG ACC AGT ACA CTG CCT CGC AAT<br>AGC GGA GCT | Somatodendritic<br>(surround = off center) |

(Legend to Table 1)
Name: Each sorting motif was named based on the "source protein" from which it was derived.
Motif: the functional name or location of each motif.
Subcellular targeted site: the reported site of preferential subcellular targeting.
Receptive Field: the central vs. surround (off-center or peripheral) region of the cell
Superscripted numbers refer to the following references:
[1]Lim S T, et al. Neuron. 25: 385-97 (2000).
[2]Garrido, J. et al. Science 300: 2091 (2003).
[3]Boiko, T. et al., J. Neurosci. 232306-2313 (2003).
[4]Rosales, C. et al. Eur. J. Neurosci. 22, 2381-2386 (2005).
[5]Lewis, T. et al. Nat. Neurosci. 12, 5680576 (2009).
[6]Xu, J. et al. J. Neurosci. 26: 9780-9793 (2006).
[7]Rivera, J. et al. Nat. Neurosci. 6: 23-250 (2003).
[8]Mutsui, S. et al., J. Neurosci. 25: 1122-1131 (2005).
[9]Dotti, F. et al., J. Neurosci. 20: 1-5 (2000).
Name: Each sorting motif was named based on the protein from which it was derived.

The functional consequence of expressing ubiquitously expressing light sensitive channels, namely ChR2, in RGC by CAG promoter, coupled with the targeting to selected subcellular sites suggest that this will contribute to restoring useful vision. However, targeting of depolarizing membrane channels, such as ChR2, to ON-type retinal neurons might result in better useful vision. By expressing a depolarizing light sensor, such as ChR2, in the desired subcellular regions of ON type retinal neurons (ON type RGC and/or ON type bipolar cells) and expressing a hypopolarizing light sensor, such as HaloR in selected subcellular sites of OFF type retinal neurons (OFF type RGC and/or OFF type bipolar cells) could create even more useful ON and OFF pathways in photoreceptor degenerated retinas that is possible without the selective targeting mediated by the sorting motifs described here. A preferred embodiment would be:

(1) By employing a "center-targeting" motif, such as Kv2.1 or Nav1.6, target ChR2 to the center receptive field of ON RGC, while targeting HaloR to the surround (=off-center) of such cells using motifs such as NLG-1 or MLPH. Activation by light of such cells would result in depolarization (stimulation) of the center and hypopolarization (inhibition) of the surround.

(2) By employing a "center-targeting" motif, such as Kv2.1 or Nav1.6, target HaloR to the center receptive field of OFF RGC, while targeting ChR2 to the surround of such cells using motifs such as NLG-1 or MLPH. Activation by light of such cells would result in inhibition of the center and stimulation of the surround.

Such combined treatment would enhance not only signal transmission but contrast and hence visual resolution in such molecularly enhanced or modified cells. This more closely resembles the physiological effects of signals transmitted to these cells by retinal photoreceptors in a normal vision state. Such specificity and selectivity would be aided by the use of ON cell-specific promoters and OFF cell-specific promoters compared to the ubiquitous promoters exemplified here. Once such promoters are identified, they would be inserted into the various vectors described here in place of CAG. Use of the present composition and methods Vectors According to the various embodiments of the present invention, a variety of known nucleic acid vectors may be used in these methods, e.g., recombinant viruses, such as recombinant adeno-associated virus (rAAV), recombinant adenoviruses, recombinant retroviruses, recombinant poxviruses, and other known viruses in the art, as well as plasmids, cosmids and phages, etc. Many publications well-known in the art discuss the use of a variety of such vectors for delivery of genes. See, e.g., Ausubel et al., *Current Protocols in Molecular Biology*, John Wiley & Sons, New York, latest edition; Kay, M A. et al., 2001, *Nat. Med.*, 7:33-40; and Walther W et al., 2000, *Drugs* 60:249-71). Methods for assembly of the recombinant vectors are well-known. See, for example, WO00/15822 and other references cited therein, all of which are incorporated by reference. There are advantages and disadvantages to the various viral vector systems. The limits of how much DNA can be packaged is one determinant in choosing which system to employ. rAAV tend to be limited to about 4.5 kb of DNA, whereas lentivirus (e.g., retrovirus) system can accommodate 4-5 kb.

AAV Vectors

Adeno-associated viruses are small, single-stranded DNA viruses which require a helper virus for efficient replication (Berns, K I, *Parvoviridae: the viruses and their replication*, p. 1007-1041 (vol. 2), in Fields, B N et al., *Fundamental Virology*, 3rd Ed., (Lippincott-Raven Publishers, Philadelphia (1995)). The 4.7 kb genome of AAV has two inverted terminal repeats (ITR) and two open reading frames (ORFs) which encode the Rep proteins and Cap proteins, respectively. The Rep reading frame encodes four proteins of molecular weights 78, 68, 52 and 40 kDa. These proteins primarily function in regulating AAV replication and rescue and integration of the AAV into the host cell chromosomes. The Cap reading frame encodes three structural proteins of molecular weights 85 (VP1), 72 (VP2) and 61 (VP3) kDa which form the virion capsid (Berns, supra). VP3 comprises >80% of total AAV virion proteins.

Flanking the rep and cap ORFs at the 5' and 3' ends are 145 bp ITRs, the first 125 bps of which can form Y- or T-shaped duplex structures. The two ITRs are the only cis elements essential for AAV replication, rescue, packaging and integration of the genome. Two conformations of AAV ITRs called "flip" and "flop" exist (Snyder, R O et al., 1993, *J Virol.,* 67:6096-6104; Berns, K I, 1990 *Microbiol Rev,* 54:316-29). The entire rep and cap domains can be excised and replaced with a transgene such as a reporter or therapeutic transgene (Carter, BJ, in Handbook of Parvoviruses, P. Tijsser, ed., CRC Press, pp. 155-68 (1990)).

AAVs have been found in many animal species, including primates, canine, fowl and human (Murphy, F A et al., *The Classification and Nomenclature of Viruses: Sixth Rept of the Int'l Comm on Taxonomy of Viruses,* Arch Virol, Springer-Verlag, 1995). Six primate serotypes are known (AAV1, AAV2, AAV3, AAV4, AAV5 and AAV6) (and more are known that infect other classes of mammals).

The AAV ITR sequences and other AAV sequences employed in generating the minigenes, vectors, and capsids, and other constructs used in the present invention may be obtained from a variety of sources. For example, the sequences may be provided by any of the above 6 AAV serotypes or other AAV serotypes or other densoviruses, including both presently known human AAV and yet to yet-to-be-identified serotypes. Similarly, AAVs known to infect other animal species may be the source of ITRs used in the present molecules and constructs. Capsids from a variety of serotypes of AAV may be combined in various mixtures with the other vector components (e.g., WO01/83692 (Hildiger et al.; U.S. Pat. No. 7,056,502; US Pat Pub. 2003/0013189 (Wilson et al). Indeed there are advantages to various virion types related to their vulnerability to pre-existing immunity in humans, the efficiency of transduction, and/or duration of expression. Thus it may be preferable to use pseudotyped, rAAV virions wherein the rAAV2 ITRs described herein are combined with AAV5 capsid proteins. Such constructs may be advantageous because humans are less likely to have been pre-exposed to AAV5 vs. AAV2, and therefore are less likely to have immunological memory (e.g., circulating antibodies or capsid-specific T lymphocytes). For other descriptions of the use of various of these rAAV virions, see, for example, WO2005/021768 (Tak et al.); Adriaansen, J et al., *Ann Rheum Dis* 2005, 64:1677-1684; US Pat. Pub. 2004-072351 (Womer et al.); U.S Pat. Pub. 2005/0255089 (Chiorini et al.), Adriaansen, J et al., *Ann Rheum Dis* 2005, 64:1677-1684, all of these references concerning rAAV are incorporated by reference in their entirety. In general, while rAAV vectors have been exemplified herein, the present invention includes AAV2 ITR's combined with capsid proteins of any of 6 known primate AAV serotypes. It is also known in the art that certain mutations in capsid proteins can enhance transfection efficiency, and it would within the ordinary skill of the art to test and select appropriate mutations for use in the present invention. Many of these viral strains or serotypes are available from the American Type Culture Collection (ATCC), Manassas, VA., or are available from a variety of other sources (academic or commercial).

It may be desirable to synthesize sequences used in preparing the vectors and viruses of the invention using known techniques, based on published AAV sequences, e.g., available from a variety of databases. The source of the sequences utilized to prepare the present constructs is not considered to be limiting. Similarly, the selection of the AAV serotype and species (of origin) is within the skill of the art and is not considered limiting.

The rAAV Minigene or Cassette

As used herein, the rAAV construct (e.g., a minigene or cassette) is packaged into a rAAV virion. At minimum, the rAAV minigene is formed by AAV ITRs and a heterologous nucleic acid molecule for delivery to a host cell. Most suitably, the minigene comprises ITRs, most preferably AAV2 ITRs, located 5' and 3' to the heterologous sequence (rhodopsin protein and targeting sequence) being expressed. Vectors comprising 5' ITR and 3' ITR sequences arranged in tandem, e.g., 5' to 3' or a head-to-tail, or in another configuration may also be useful. Other embodiments include a minigene with multiple copies of the ITRs, or one in which 5' ITRs (or conversely, 3' ITRs) are located both 5' and 3' to the heterologous sequence. The ITRs sequences may be located immediately upstream and/or downstream of the heterologous sequence; intervening sequences may be present. As noted, the preferred ITRs are from AAV2, but they may also originate from AAV5 or from any other AAV serotype. Moreover, the present construct or minigene may include 5' ITRs from one serotype and 3' ITRs from another.

The AAV sequences used are preferably the 140145 by cis-acting 5' and 3' ITR sequences (e.g., Carter, BJ, supra). Preferably, the entire ITR sequence is used, although minor modifications are permissible. The most ITR's used in the present examples are

```
5' ITR:
                                                  (SEQ ID NO: 17)
cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac taggggttcc t                                       141

3' ITR:
                                                  (SEQ ID NO: 18)
aggaacccct agtgatggag ttggccactc cctctctgcg cgctcgctcg ctcactgagg
ccgggcgacc aaaggtcgcc cgacgcccgg gctttgcccg gqcqgcctca gtgagcgagc
gagcgcgcag ctgcctgcag g                                       141
```

Methods for modifying these ITR sequences are well-known (e.g., Sambrook, J. et al., *Molecular Cloning: A Laboratory Manual,* 3rd Edition, Cold Spring Harbor Press, Cold Spring Harbor, NY, 2001; Brent, R et al., eds., *Current Protocols in Molecular Biology,* John Wiley & Sons, Inc., 2003; Ausubel, F M et al., eds., *Short Protocols in Molecular Biology,* 5th edition, *Current Protocols,* 2002; Carter et al., supra; and Fisher, K et al., 1996 J Virol. 70:520-32). It is conventional to engineer the rAAV virus using known methods (e.g., Bennett, J et al. 1999, supra).

An example of such a molecule employed in the present invention is a "cis-acting" plasmid containing the heterologous sequence, preferably the ChR2 (any of SEQ ID NO:29-38) or HaloR sequence (any of SEQ ID NO:39-46, with or without an in-frame GFP sequence, with an in-frame sorting motif, promoter/regulatory sequences, all flanked by the 5' and 3' AAV ITR sequences.

The heterologous sequence encodes a protein or polypeptide which is desired to be delivered to and expressed in a cell and a targeting motif that differentially targets the polypeptide to particular subcellular regions of the cell, preferably an RGC.

The Transgene(s) being Targeted and Expressed

In a most preferred embodiment, the heterologous sequence is a nucleic acid molecule that functions as a transgene. The term "transgene" as used herein refers to a nucleic acid sequence heterologous to the AAV sequence, and encoding a desired product, preferably ChR2 or HaloR plus the sorting motif, and the regulatory sequences which direct or modulate transcription and/or translation of this nucleic acid in a host cell, enabling expression in such cells of the encoded product. Preferred polypeptide products are those that can be delivered to the eye, particularly to retinal neurons, most preferably to RGC.

The transgene/targeting sequence is delivered and differentially expressed in selected subcellular sites as directed by the sorting motif, in order to treat or otherwise improve the vision status of a subject with an ocular disorder. The targeted ocular cells are preferably retinal neurons, namely, bipolar cells and most preferably, RGC.

Based on the studies reported in WO2007/131180, the brightness of the light needed to stimulate evoked potential in transduced mouse retinas, indicates that a channel opsin with increased light sensitivity may be more desirable. This can be achieved by selection of a suitable naturally occurring opsin, for example other microbial-type rhodopsins, or by modifying the light sensitivity of ChR2 as well as its other properties, such as ion selectivity and spectral sensitivity, to produce diversified light-sensitive channels to better fit the need for vision restoration.

Different transgenes may be used to encode separate subunits of a protein being delivered, or to encode different polypeptides the co-expression of which is desired. If a single transgene includes DNA encoding each of several subunits, the DNA encoding each subunit may be separated by an internal ribozyme entry site (IRES), which is preferred for short subunit-encoding DNA sequences (e.g., total DNA, including IRES is <5 kB). Other methods which do not employ an IRES may be used for co-expression, e.g., the use of a second internal promoter, an alternative splice signal, a co-or post-translational proteolytic cleavage strategy, etc., all of which are known in the art.

The coding sequence or non-coding sequence of the present nucleic acids, including all domains to be expressed preferably are codon-optimized for the species in which they are to be expressed, particularly mammals and humans. Such codon-optimization is routine in the art.

While a preferred transgene encodes a full length polypeptide, preferably ChR2, the present invention is also directed to vectors that encode a biologically active fragment of ChR2 (nucleotides: SEQ ID NO:19; amino acids: SEQ ID NO:20) or a (preferably conservative) amino acid substitution variant or mutant of ChR2, or a full length HaloR (nucleotide SEQ ID NO:23; amino acid SEQ ID NO:24) or a biologically active fragment, variant, mutant, or fusion/chimeric nucleic acid encoding a fusion protein. A preferred point mutation named CatCh (calcium translocating channelrhodopsin (mutation at L132C) mediates an accelerated response time and a voltage response that is ~70-fold more light sensitive than that of wild-type ChR2; these properties stem from enhanced Ca2+ permeability.

(Kleinlogel, S et al., Nature *Neuroscience* 14:513-518 (2011)). Such variants, mutants and fragments of any other polypeptide of the invention to be expressed in retinal neurons are within the scope of this invention. When a fragment or variant of the full length and native coding sequence is expressed by the targets cells being transformed and is able to endow such cells with light sensitivity that is functionally equivalent to that of the full length or substantially full length polypeptide having a native, rather than variant, amino acid sequence. A biologically active fragment or variant is a "functional equivalent"—a term that is well understood in the art and is further defined in detail herein. The requisite biological activity of the encoded fragment or variant, using any method disclosed herein or known in the art to establish activity of a channel opsin, has the following activity relative to the wild-type native polypeptide: about 50%, about 55%, about 60%, about 65%, about 70%, about 75%, about 80%, about 85%, about 90%, about 95%, about 99%, and any range derivable therein, such as, for example, from about 70% to about 80%, and more preferably from about 81% to about 90%; or even more preferably, from about 91% to about 99%.

It should be appreciated that any variations in the coding sequences of the present nucleic acids and vectors that, as a result of the degeneracy of the genetic code, express a polypeptide of the same sequence, are included within the scope of this invention.

The amino acid sequence identity of the encoded polypeptide variants of the present invention are determined using standard methods, typically based on certain mathematical algorithms. In a preferred embodiment, the percent identity between two amino acid sequences is determined using the Needleman and Wunsch (J. Mol. Biol. 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg-.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers and Miller (CABIOS, 4:11-17 (1989)) which has been incorporated into the ALIGN program (version 2.0), using a PAM120 weight residue table, a gap length penalty of 12 and a gap penalty of 4. The nucleotide and amino acid sequences of the present invention can further be used as a "query sequence" to perform a search against public databases, for example, to identify other family members or related sequences. Such searches can be performed using the NBLAST and XBLAST programs (Altschul et al. (1990) J. Mol. Biol. 215:403-10). BLAST nucleotide searches can be performed with the NBLAST program, score=100, wordlength=12 to obtain nucleotide sequences homologous to, e.g., DAN encoding Chop2 of *C. reinhardtii*. BLAST protein searches can be performed with the XBLAST program, score=50, wordlength=3 to obtain amino acid sequences homologous to the appropriate reference protein such as Chop2. To obtain gapped alignments for comparison purposes, Gapped BLAST can be utilized (Altschul et al. (1997) *Nucleic Acids Res.* 25:3389-3402). When utilizing BLAST and Gapped BLAST programs, the default parameters of the respective programs (e.g. XBLAST and NBLAST) can be used. See World Wide Web URL ncbi.nlm.nih.gov.

The preferred amino acid sequence variant has the following degrees of sequence identity with the native, full length channel opsin polypeptide, preferably Chop2 from *C. reinhardtii* (SEQ ID NO: 21) or with a fragment thereof: about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, from about 70% to about 80%, and more preferably from about 81% to about 90%; or even more preferably, from about 91% to about 99% identity. A preferred biologically active fragment comprises or consists of SEQ ID NO:3, which corresponds to residues 1-315 of the full length SEQ ID NO:6, or comprises or consists of SEQ ID NO:8.

Any of a number of known recombinant methods are used to produce a DNA molecule encoding the fragment or variant. For production of a variant, it is routine to introduce mutations into the coding sequence to generate desired amino acid sequence variants of the invention. Site-directed mutagenesis is a well-known technique for which protocols and reagents are commercially available (e.g., Zoller, M J et al., 1982, *Nucl Acids Res* 10:6487-6500; Adelman, J P et al., 1983, *DNA* 2:183-93). These mutations include simple deletions or insertions, systematic deletions, insertions or substitutions of clusters of bases or substitutions of single bases.

In terms of functional equivalents, it is well understood by those skilled in the art that, inherent in the definition of a "biologically functional equivalent" protein, polypeptide, gene or nucleic acid, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, the shorter the length of the polypeptide, the fewer amino acids changes should be made. Longer fragments may have an intermediate number of changes. The full length polypeptide protein will have the most tolerance for a larger number of changes. It is also well understood that where certain residues are shown to be particularly important to the biological or structural properties of a polypeptide residues in a binding regions or an active site, such residues may not generally be exchanged. In this manner, functional equivalents are defined herein as those poly peptides which maintain a substantial amount of their native biological activity.

For a detailed description of protein chemistry and structure, see Schulz, G E et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIGS. 3-9 of Creighton (supra). Based on such an analysis, conservative substitutions are defined herein as exchanges within one of the following five groups:

| 1 | Small aliphatic, nonpolar or slightly polar residues | Ala, Ser, Thr (Pro, Gly); |
|---|---|---|
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

The hydropathy index of amino acids may also be considered in selecting variants. Each amino acid has been assigned a hydropathy index on the basis of their hydrophobicity and charge characteristics, these are: Ile (+4.5); Val (+4.2); Leu (+3.8); Phe (+2.8); Cys (+2.5); Met (+1.9); Ala (+1.8); Glycine (−0.4); Thr (−0.7); Ser (−0.8); Trp (−0.9); Tyr (−1.3); Pro (−1.6); His (−12); Glu (−3.5); Gln (−3.5); Asp (−3.5); Asn (−3.5); Lys (−3.9); and Arg (−4.5). The importance of the hydropathy index in conferring interactive biological function on a proteinaceous molecule is generally understood in the art (Kyte and Doolittle, 1982, *J. Mol. Biol.* 157:105-32). It is known that certain amino acids may be substituted for other amino acids having a similar hydropathy index or score and still retain a similar biological activity. In making changes based upon the hydropathy index, the substitution of amino acids whose hydropathy indices are within +2 is preferred, those which are within +1 are particularly preferred, and those within +0.5 are even more particularly preferred. It is also understood in the art that the substitution of like amino acids can be made effectively on the basis of hydrophilicity, particularly where the biological functional equivalent polypeptide thereby created is intended for use in certain of the present embodiments. U.S. Pat. No. 4,554,101, discloses that the greatest local average hydrophilicity of a proteinaceous molecule, as governed by the hydrophilicity of its adjacent amino acids, correlates with a biological property of the molecule. See U.S. Pat. No. 4,554,101 for a hydrophilicity values. In making changes based upon similar hydrophilicity values, the substitution of amino acids whose hydrophilicity values are within +2 is preferred, those which are within +1 are particularly preferred, and those within +0.5 are even more particularly preferred.

Vector Components and Their Sequences.
Promoters/Regulatory Sequences

The expression vector of the present invention includes appropriate sequences operably linked to the coding sequence(s) or ORF(s) to promote its expression in a targeted host cell. "Operably linked" sequences include both expression control sequences such as. promoters that are contiguous with the coding sequences and expression control sequences that act in trans or distally to control the expression of the polypeptide product.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance protein processing and/or secretion. Many varied expression control sequences, including native and non-native, constitutive, inducible and/or tissue-specific, are known in the art and may be utilized herein, depending upon the type of expression desired.

Expression control sequences for eukaryotic cells typically include a promoter, an enhancer, such as one derived from an immunoglobulin gene, SV40, CMV, etc., and a polyadenylation sequence which may include splice donor and acceptor sites. The polyadenylation (polyA) sequence generally is inserted 3' to the coding sequence and 5' to the 3' ITR sequence. The polyA from bovine growth hormone (bGH) is a suitable sequence and is abbreviated "bGH-polyA" (SEQ ID NO: 28).

The regulatory sequences useful herein may also contain an intron, such as one located between the promoter/enhancer sequence and the coding sequence. One useful intron sequence is derived from SV40, and is referred to as the SV40 T intron sequence. Another includes the woodchuck hepatitis virus post-transcriptional element. (See, for example, Wang L and Verma, I, 1999, *Proc Nat'l Acad Sci USA*, 96:3906-10).

An IRES sequence, or other suitable system as discussed above, may be used to produce more than one polypeptide from a single transcript. An exemplary IRES is the poliovirus IRES which supports transgene expression in photoreceptors, RPE and ganglion cells. Preferably, the IRES is located 3' to the coding sequence in the present vector, preferably an rAAV vector.

The promoter may be selected from a number of constitutive or inducible promoters that can drive expression of the selected transgene in an ocular setting, preferably in retinal neurons. A preferred promoter is "cell-specific", meaning that it is selected to direct expression of the selected transgene in a particular ocular cell type, such as photoreceptor cells.

A preferred constitutive promoters include the exemplified hybrid cytomegalovirus (CMV) immediate early enhancer/chicken β-actin promoter-exon 1-intron 1 element (together abbreviated as "CAG" SEQ ID NO:26, herein) used along with woodchuck hepatitis virus posttranscriptional regulatory element (abbreviated herein as "WPRE"; SEQ ID NO:27 herein). However, for human safety, other posttranscriptional regulatory elements known in the art can readily be substituted for WPRE.

Other useful promoters include RSV LTR promoter/enhancer, the SV40 promoter, the CMV promoter, the dihydrofolate reductase (DHFR) promoter, and the phosphoglycerol kinase (PGK) promoter. Additional useful promoters are disclosed in W.W. Hauswirth et al., 1998, WO98/48027 and A. M. Timmers et al., 2000, WO00/15822. Promoters that were found to drive RPE cell-specific gene expression in vivo include (1) a 528-bp promoter region (bases 1-528 of a murine 11-cis retinol dehydrogenase (RDH) gene (Driessen, C A et al., 1995, *Invest. Ophthalmol. Vis. Sci.* 36:1988-96; Simon, A. et al., 1995, *J. Biol. Chem* 270:1107-12, 1995; Simon, A. et al., 1996, *Genomics* 36:424-3) Genbank Accession Number X97752); (2) a 2274-bp promoter region) from a human cellular retinaldehyde-binding protein (CRALBP) gene (Intres, R et al., 1994, *J. Biol. Chem.* 269:25411-18; Kennedy, B N et al., 1998, *J. Biol. Chem.* 273:5591-8, 1998), Genbank Accession Number L34219); and (3) a 1485-bp promoter region from human RPE65 (Nicoletti, A et al., 1998, *Invest. Ophthalmol. Vis. Sci.* 39, 637-44, Genbank Accession Number U20510). These three promoters in WO00/15822 promoted RPE-cell-specific expression of GFP. It is envisioned that minor sequence variations in the various promoters and promoter regions discussed herein-whether additions, deletions or mutations, whether naturally occurring or introduced in vitro, will not affect their ability to drive expression in the cellular targets of the coding sequences of the present invention. Furthermore, the use of other promoters, even if not yet discovered, that are characterized by abundant and/or specific expression in retinal cells, particularly in bipolar or ganglion cells, is specifically included within the scope of this invention.

Another useful promoter is from a mGluR6 promoter-region of the Grm6 gene (GenBank accession number BC041684), a gene that controls expression of metabotropic glutamate receptor 6 ((Ueda Y et al., 1997, *J Neurosc.* 17:3014-23). The genomic sequence is shown in GenBank accession number-AL627215. A preferred example of this promoter region sequence from the above GenBank record consists of 11023 nucleotides. The original Umeda et al., study employed a kb promoter, but the actual length of the promoter and the sequence that comprises control elements of Grm6 can be adjusted by increasing or decreasing the fragment length. It is a matter of routine testing to select and verify the action of the optimally sized fragment from the Grm6 gene that drives transgenic expression of a selected coding sequence, preferably ChR2 or HaloR, in the desired target cells, preferably in bipolar cells which are rich in glutamate receptors, particularly the "on" type bipolar cells, which are the most bipolar cells in the retina (Nakajima, Y., et al., 1993, *J Biol Chem* 268:11868-73). Use of such a large promoter is not compatible with the packaging capabilities of rAAV virions, so would require a different delivery vector system known in the art, or identification of a shorter sequence (<2.5 kb) that could be packaged in an rAAV vector of the present invention.

Another promoter is the Pcp2 (L7) promoter (Tomomura, M et al., 2001, *Eur J Neurosci.* 14:57-63). Again, the length of the active promoter is preferably less than 2.5 Kb so it can be packaged into the rAAV viral cassette.

The neurokinin-3 (NK-3) promoter could be used to target HalorR to OFF cells (Haverkamp, S et al., 2002, *J Comparative Neurology*, 455:463-76.

An inducible promoter is used to control the amount and timing of production of the transgene product in an ocular cell. Such promoters can be useful if the gene product has some undesired, e.g., toxic, effects in the cell if it accumulates excessively. Inducible promoters include those known in the art, such as the Zn-inducible sheep metallothionine (MT) promoter, the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any inducible promoter the action of which is tightly regulated and is specific for the particular target ocular cell type, may be used. Other useful types of inducible promoters are ones regulated by a specific physiological state, e.g., temperature, acute phase, a cell's replicating or differentiation state.

Selection of the various vector and regulatory elements for use herein are conventional, well-described, and readily available. See, e.g., Sambrook et al., supra; and Ausubel et al., supra. It will be readily appreciated that not all vectors and expression control sequences will function equally well to express the present transgenes Chop2 or HaloR. Clearly, the skilled artisan may apply routine selection among the known expression control sequences without departing from the scope of this invention and based upon general knowledge as well as the guidance provided herein. One skilled in the art can select one or more expression control sequences, operably link them to the coding sequence being expressed to make a minigene, insert the minigene or vector into an AAV vector, preferably rAAV2, and cause packaging of the vector into infectious particles or virions following one of the known packaging methods for rAAV.

Production of the rAAV

The rAAV2 used in the present invention may be constructed and produced using the materials and methods described herein and those well-known in the art. The methods that are preferred for producing any construct of this invention are conventional and include genetic engineering, recombinant engineering, and synthetic techniques, such as those set forth in reference cited above.

Briefly, to package an rAAV construct into an rAAV virion, a sequences necessary to express AAV rep and AAV cap or functional fragments thereof as well as helper genes essential for AAV production must be present in the host cells. See, for example U.S. Pat. Pub. 2007/0015238, which describes production of pseudotyped rAAV virion vectors encoding AAV Rep and Cap proteins of different serotypes and AdV transcription products that provide helper functions. For example, AAV rep and cap sequences may be introduced into the host cell in any known manner including, without limitation, transfection, electroporation, liposome delivery, membrane fusion, biolistic deliver of DNA-coated pellets, viral infection and protoplast fusion. Devices specifically adapted for delivering DNA to specific regions within and around the eye for the purpose of gene therapy have been described (for example, U.S. Pat. Pub. 2005/0277868, incorporated by reference) are used within the scope of this invention. Such devices utilize electroporation and electromigration, providing, e.g., two electrodes on a flexible support that can be placed behind the retina. A third electrode is part of a hollow support, which can also be used to inject the molecule to the desired area. The electrodes can be positioned around the eye, including behind the retina or within the vitreous.

These sequences may exist stably in the cell as an episome or be stably integrated into the cell's genome. They may also be expressed more transiently in the host cell. As an example, a useful nucleic acid molecule comprises, from 5' to 3', a promoter, an optional spacer between the promoter and the start site of the rep sequence, an AAV rep sequence, and an AAV cap sequence.

The rep and cap sequences, along with their expression control sequences, are preferably provided in a single vector, though they may be provided separately in individual vectors. The promoter may be any suitable constitutive, inducible or native promoter. The delivery molecule that provides the Rep and Cap proteins may be in any form, preferably a plasmid which may contain other non-viral sequences, such as those to be employed as markers. This molecule typically excludes the AAV ITRs and packaging sequences. To avoid the occurrence of homologous recombination, other viral sequences, particularly adenoviral sequences, are avoided. This plasmid is preferably one that is stably expressed.

Conventional genetic engineering or recombinant DNA techniques described in the cited references are used. The rAAV may be produced using a triple transfection method with either the calcium phosphate (Clontech) or Effectene™ reagent (Qiagen) according to manufacturer's instructions. See, also, Herzog et al., *Nat. Med.* 5:56-63 (1999).

The rAAV virions are produced by culturing host cells comprising a rAAV as described in Bi et al., supra, and WO2007/131180, which includes a rAAV construct to be packaged into a rAAV virion, an AAV rep sequence and an AAV cap sequence, all under control of regulatory sequences directing expression.

Suitable viral helper genes, such as adenovirus E2A, E4Orf6 and VA, may be added to the culture preferably on separate plasmids. Thereafter, the rAAV virion which directs expression of the transgene is isolated in the absence of contaminating helper virus or wild type AAV.

It is conventional to assess whether a particular expression control sequence is suitable for a given transgene, and choose the one most appropriate for expressing the transgene. For example, a target cell may be infected in vitro, and the number of copies of the transgene in the cell monitored by Southern blots or quantitative PCR. The level of RNA expression may be monitored by Northern blots quantitative RT-PCR. The level of protein expression may be monitored by Western blot, immunohistochemistry, immunoassay including enzyme immunoassay (EIA) such as enzyme-linked immunosorbent assays (ELISA), radioimmunoassays (RIA) or by other methods. Specific embodiments are described below.

Preferred Vectors of the Invention

This section lists a number of vectors useful in the present invention that comprise the following nucleotide sequences encoding (a) Light Sensor: ChR2 coding sequence (preferably SEQ ID NO:21) or HaloR coding sequence (SEQ ID NO:23)

(b) Optionally, a reporter "gene" preferably GFP (SEQ ID NO:25)

(c) 5' and 3' ITRs from AAV2, SEQ ID NO:17 and 18, respectively.

(d) CAG Promoter/Regulatory sequence (SEQ ID NO:26)

(e) Posttranscriptional Regulatory element WPRE (SEQ ID NO:27)

(f) Polyadenylation sequence (SEQ ID NO:28)

In addition to the foregoing, the vector preferably contains (g) the rAAV2 backbone sequences located 3' from the 3' ITR.

Schematics and annotated sequences of preferred vectors are given in FIG. 2A-2C, FIG. 3A-3B, FIG. 4A-4C, FIG. 5A-5B, FIG. 6A-6B, FIG. 7A-7B, FIG. 8A-8B, FIG. 9A-9B, FIG. 10A-10B, FIG. 11A-11B, FIG. 12A-12B, FIG. 13A-13B, FIG. 14A-14C, FIG. 15A-15B, FIG. 16A-16B, FIG. 17A-17B, FIG. 18A-18B, and FIG. 19A-19B.

Pharmaceutical Compositions and Methods of the Invention

The vectors that comprises the ChR2 or HaloR transgene and the targeting motifs disclosed herein for use to target retinal neurons as described above should be assessed for contamination using conventional methods and formulated into a sterile or aseptic pharmaceutical composition for administration by, for example, subretinal injection.

Such formulations comprise a pharmaceutically and/or physiologically acceptable vehicle, diluent, carrier or excipient, such as buffered saline or other buffers, e.g., HEPES, to maintain physiologic pH. For a discussion of such components and their formulation, see, generally, Gennaro, AE., *Remington: The Science and Practice of Pharmacy*, Lippincott Williams & Wilkins Publishers; 2003 or latest edition). See also, WO00/15822. For prolonged storage, the preparation may be frozen, for example, in glycerol.

The pharmaceutical composition described above is administered to a subject having a visual or blinding disease by any appropriate route, preferably by intravitreal or subretinal injection, depending on the retinal layer being targeted.

Disclosures from Bennett and colleagues (cited herein) concern targeting of retinal pigment epithelium—the most distal layer from the vitreal space. According to the present invention, the DNA construct is targeted to either retinal ganglion cells or bipolar cells. The ganglion cells are reasonably well-accessible to intravitreal injection. Intravitreal and/or subretinal injection can provide the necessary access to the bipolar cells, especially in circumstances in which the photoreceptor cell layer is absent due to degeneration-which is the case in certain forms of degeneration that the present invention is intended to overcome.

To test for the vector's ability to express the transgene, specifically in mammalian retinal neurons, preferably RGC, by AAV-mediated delivery, a combination of a preferred promoter sequence linked to a reporter gene such as GFP or LacZ can be packaged into rAAV virus particles, concentrated, tested for contaminating adenovirus and titered for rAAV. The right eyes of a number of test subjects, preferably inbred mice, are injected sub-retinally with about 1 µl of the rAAV preparation (e.g., greater than about 1010 infectious units ml). Two weeks later, the right (test) and left (control) eyes of half the animals are removed, fixed and stained with an appropriate substrate or antibody or other substance to reveal the presence of the reporter gene. A majority of the test retinas in injected eyes will exhibited a focal stained region, e.g., blue for LacZ/Xgal, or green for GFP consistent with a subretinal bleb of the injected virus creating a localized retinal detachment. All control eyes are negative for the reporter gene product. Reporter gene expression examined in mice sacrificed at later periods is detected for at least 10 weeks post-injection, which suggests persistent expression of the reporter transgene.

An effective amount of rAAV virions carrying a nucleic acid sequence according to this invention encoding the ChR2 or HaloR and targeting motif under the control of the promoter of choice, preferably CAG or a cell-specific promoter such as mGluR6, is preferably in the range of between about 1010 to about 1013 rAAV infectious units in a volume of between about 150 and about 800 µl per injection. The rAAV infectious units can be measured according to McLaughlin, S K et al., 1988, *J Virol* 62:1963. More preferably, the effective amount is between about 1010 and about $10^{12}$ rAAV infectious units and the injection volume is preferably between about 250 and about 500 µl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Ocular Disorders

The ocular disorders for which the present methods are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, EI, ed., *Genetic Diseases of the Eye*, Oxford University Press, NY, 1998).

In particular, this method is useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by this method. Thus, the particular ocular disorder treated by this method may include the above-mentioned disorders and a number of diseases which have yet to be so characterized.

Visual information is processed through the retina through two pathways: an ON pathway which signals the light ON, and an OFF pathway which signals the light OFF (Wässle, supra). It is generally believed that the existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells are hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cell) to ON an OFF cone bipolar cell.

Electrical/Visual activity Recording and Measurement
Patch-Clamp Recordings

Dissociated retinal cells and retinal slice are prepared, e.g., as described by Pan, Z.-H. *J. Neurophysiol.* 83 513-527 (2000); J. Cui, Y P et al., *J. Physiol.* 553:895-909 (2003). Recordings with patch electrodes in the whole-cell configuration can be made by an EPC-9 amplifier and PULSE software (Heka Electronik, Lambrecht, Germany). Recordings are preferably made in Hanks' solution containing (in mM): NaCl, 138; NaHCO$_3$, 1; Na$_2$HPO$_4$, 0.3; KCl, 5; KH$_2$PO$_4$, 0.3; CaCl$_2$), 1.25; MgSO$_4$, 0.5; MgCl$_2$, 0.5; HEPES-NaOH, 5; glucose, 22.2; with phenol red, 0.001% v/v; adjusted to pH 7.2 with 0.3 N NaOH. The electrode solution contains (in mM): K-gluconate, 133; KCl, 7; $MgCl_2$, 4; EGTA, 0.1; HEPES, 10; Na-GTP, 0.5; and Na-ATP, 2; pH adjusted with KOH to 7.4. The resistance of the electrode is about 13 to 15 MΩ. The recordings are performed at room temperature.

Multielectrode Array Recordings

The multielectrode array recordings are on the procedures reported by Tian, N. et al., Neuron 39:85-96 (2003). Briefly, retinas are dissected and placed photoreceptor side down on a nitrocellulose filter paper strip. The mounted retina is placed in the MEA-60 multielectrode array recording chamber of 30 μm diameter electrodes spaced 200 μm apart (Multi Channel System MCS GmbH, Reutlingen, Germany), with the ganglion cell layer facing the recording electrodes. The retina is continuously perfused in oxygenated extracellular solution at 34° C. The extracellular solution preferably contains (in mM): NaCl, 124; KCl, 2.5; $CaCl_2$, 2; $MgCl_2$, 2; $NaH_2PO_4$, 1.25; $NaHCO_3$, 26; and glucose, 22 (pH 7.35 with 95% $O_2$ and 5% $CO_2$). Recordings are usually started 60 min after the retina is positioned in the recording chamber. The interval between onsets of each light stimulus is generally 10-15 s. The signals are filtered between 200 Hz (low cut off) and 20 kHz (high cut off). The responses from individual neurons are analyzed using, e.g., Offline Sorter software (Plexon, Inc., Dallas, TX).

Visual-Evoked Potential Recordings

Visual-evoked potential recordings are carried out, for example, in wild-type mice of the C57BL/6 and 129/Sv strains aged 4-6 months and in rdl/rdl mice aged 6-11 months. Recordings are performed 2-6 months after viral vector injection. After general anesthesia, animals are mounted in a stereotaxic apparatus. Body temperature may be unregulated or maintained at 34° C. with a heating pad and a rectal probe. Pupils are dilated with 1% atropine and 2.5% accu-phenylephrine. A small portion of the skull (~1.5×1.5 mm) centered about 2.5 mm from the midline and 1 mm rostral to the lambdoid suture is drilled and removed. Recordings are made from visual cortex (area V1) by a glass micropipette (resistance ~0.5 M after filling with 4 M NaCl) advanced 0.4 mm beneath the surface of the cortex at the contralateral side of the stimulated eye. The stimuli are 20 ms pluses at 0.5 Hz. Responses are amplified (1,000 to 10,000), band-pass filtered (0.3-100 Hz), digitized (1 kHz), and averaged over 30-250 trials.

Light Stimulation

For dissociated cell and retinal slice recordings, light stimuli are generated by a 150 W xenon lamp-based scanning monochromator with bandwidth of 10 nm (TILL Photonics, Germany) and coupled to the microscope with an optical fiber. For multielectrode array recordings, light responses are evoked by the monochromator or a 175 W xenon lamp-based illuminator (Lambda LS, Sutter Instrument) with a band-pass filter of 400-580 nm and projected to the bottom of the recording chamber through a liquid light guider. For visual evoked potential, light stimuli are generated by the monochromator and projected to the eyes through the optical fiber. The light intensity is attenuated by neutral density filters. The light energy is measured by a thin-type sensor (TQ82017) and an optical power meter (e.g., Model: TQ8210, Advantest, Tokyo, Japan).

Restoration or Improvement of Light Sensitivity and Vision

Both in vitro and in vivo studies to assess the various parameters of the present invention may be used, along with any recognized animal model of a blinding human ocular disorder. Large animal models of human retinopathy, e.g., childhood blindness, are useful. The examples provided herein allow one of skill in the art to readily appreciate that this method may be used similarly to treat a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters. Behavioral measures can be obtained using known animal models and tests, for example performance in a water maze, wherein a subject in whom vision has been preserved or restored to varying extents will swim toward light (Hayes, J M et al., 1993, Behav Genet 23:395-403).

In models in which blindness is induced during adult life or in congenital blindness that develops slowly enough for the individual to experience vision before its loss, training in various tests may be done. When these tests are re-administered after visual loss to test the efficacy of the present compositions and methods for their vision-restorative effects, animals do not have to learn the tasks de novo while in a blind state. Other behavioral tests do not require learning and rely on instinctiveness of certain behaviors. An example is the optokinetic nystagmus test (Balkema G W et al., 1984, Invest Ophthal Vis Sci. 25:795-800; Mitchiner J C et al., 1976, Vision Res. 16:1169-71).

As is exemplified herein, the transfection of retinal neurons with DNA encoding Chop2 provides residual retinal neurons, principally bipolar cells and ganglion cells, with photosensitive membrane channels. Thus, it was possible to measure, with a strong light stimulus, the transmission of a visual stimulus to the animal's visual cortex, the area of the brain responsible for processing visual signals; this therefore constitutes a form of vision, as intended herein. Such vision may differ from forms of normal human vision and may be referred to as a sensation of light, also termed "light detection" or "light perception."

Thus, the term "vision" as used herein is defined as the ability of an organism to usefully detect light as a stimulus for differentiation or action. Vision is intended to encompass:

1. Light detection or perception—the ability to discern whether or not light is present
2. Light projection—the ability to discern the direction from which a light stimulus is coming;
3. Resolution—the ability to detect differing brightness levels (i.e., contrast) in a grating or letter target;
4. Recognition—the ability to recognize the shape of a visual target by reference to the differing contrast levels within the target.

Thus, "vision" includes the ability to simply detect the presence of light. This opens the possibility to train an affected subject who has been treated according to this invention to detect light, enabling the individual to respond remotely to his environment however crude that interaction might be. In one example, a signal array is produced to which a low vision person can respond to that would enhance the person's ability to communicate by electronic means remotely or to perform everyday tasks. In addition such a person's mobility would be dramatically enhanced if trained to use such a renewed sense of light resulting from "light detection." The complete absence of light perception leaves a person with no means (aside from hearing and smell) to discern anything about objects remote to himself.

The methods of the present invention that result in light perception, even without full normal vision, also improve or support normally regulated circadian rhythms which control many physiological processes including sleep-wake cycles and associated hormones. Although some blind individuals with residual RGCs can mediate their rhythms using RGC melanopsin, it is rare for them to do so. Thus, most blind persons have free-running circadian rhythms. Even when they do utilize the melanopsin pathway, the effect is very weak. The methods of the present invention are thus expected to improve health status of blind individuals by enabling absent light entrainment or improving weakened (melanopsin-mediated) light entrainment of circadian rhythms which leads to better overall health and well-being.

In addition to rhythms, the present invention provides a basis to improve deficits in other light-induced physiological phenomena. Photoreceptor degeneration may result in varying degrees of negative masking, or suppression, of locomotor activity during the intervals in the circadian cycle in which the individual should be sleeping. Suppression of pineal melatonin may occur. Both contribute to the entrainment process. Thus, improvement in these responses/activities in a subject in whom photoreceptors are or have degenerated contributes, independently of vision per se, to appropriate sleep/wake cycles that correspond with the subject's environment in the real world.

Yet another benefit of the present invention is normalization of pupillary light reflexes because regulation of pupil size helps modulate the effectiveness of light stimuli in a natural feed back loop. Thus, the present invention promotes re-establishment of this natural feedback loop, making vision more effective in subject treated as described herein.

In certain embodiments, the present methods include the measurement of vision before, and preferably after, administering the present vector. Vision is measured using any of a number of methods well-known in the art or ones not yet established. Most preferred are:

(1) A light detection response by the subject after exposure to a light stimulus—in which evidence is sought for a reliable response of an indication or movement in the general direction of the light by the subject individual when the light is turned on.

(2) a light projection response by the subject after exposure to a light stimulus in which evidence is sought for a reliable response of indication or movement in the specific direction of the light by the individual when the light is turned on.

(3) light resolution by the subject of a light vs. dark patterned visual stimulus, which measures the subject's capability of resolving light vs dark patterned visual stimuli as evidenced by:
  (a) the presence of demonstrable reliable optokinetically produced nystagmoid eye movements and/or related head or body movements that demonstrate tracking of the target (see above) and/or
  (b) the presence of a reliable ability to discriminate a pattern visual stimulus and to indicate such discrimination by verbal or non-verbal means, including, for example pointing, or pressing a bar or a button; or (4) electrical recording of a visual cortex response to a light flash stimulus or a pattern visual stimulus, which is an endpoint of electrical transmission from a restored retina to the visual cortex. Measurement may be by electrical recording on the scalp surface at the region of the visual cortex, on the cortical surface, and/or recording within cells of the visual cortex.

It is known in the art that it is often difficult to make children who have only light perception appreciate that they have this vision. Training is required to get such children to react to their visual sensations. Such a situation is mimicked in the animal studies exemplified below. Promoting or enhancing light perception, which the compositions and methods of the present invention will accomplish, is valuable because patients with light perception not only are trainable to see light, but they can usually be trained to detect the visual direction of the light, thus enabling them to be trained in mobility in their environment. In addition, even basic light perception can be used by visually impaired individuals, including those whose vision is improved using the present compositions and methods, along with specially engineered electronic and mechanical devices to enable these individuals to accomplish specific daily tasks. Beyond this and depending on their condition, they may even be able to be trained in resolution tasks such as character recognition and even reading if their impairment permits. Thus it is expected that the present invention enhances the vision of impaired subjects to such a level that by applying additional training methods, these individuals will achieve the above objectives.

Low sensitivity vision may emulate the condition of a person with a night blinding disorder, an example of which is Retinitis Pigmentosa (RP), who has difficulty adapting to light levels in his environment and who might use light amplification devices such as supplemental lighting and/or night vision devices.

Thus, the visual recovery that has been described in the animal studies described below would, in human terms, place the person on the low end of vision function. Nevertheless, placement at such a level would be a significant benefit because these individuals could be trained in mobility and potentially in low order resolution tasks which would provide them with a greatly improved level of visual independence compared to total blindness.

The mice studied in the present Examples were rendered completely devoid of photoreceptors; this is quite rare, even in the worst human diseases. The most similar human state is RP. In most cases of RP, central vision is retained till the very end. In contrast, in the studied mouse model, the mouse becomes completely blind shortly after birth.

Common disorders encountered in low vision are described by J. Tasca and E. A. Deglin in Chap. 6 of *Essentials of Low Vision Practice*, R. L. Brilliant, ed., Butterworth Heinemann Publ., 1999, which is incorporated by reference in its entirety. There is reference to similar degenerative conditions, but these references show form vision that is measurable as visual acuity. Ganglion cell layers are not retained in all forms of RP, so the present approach will not work for such a disorder.

When applying the present methods to humans with severe cases of RP, it is expected that central vision would be maintained for a time at some low level while the peripheral retina degenerated first. It is this degenerating retina that is the target for re-activation using the present invention. In essence, these individuals would be able to retain mobility vision as they approached blindness gradually.

Subjects with macular degeneration, characterized by photoreceptor loss within the central "sweet spot" of vision (Macula Lutea), are expected to benefit by treatment in accordance with the present invention, in which case the resolution capability of the recovered vision would be expected to be higher due to the much higher neuronal density within the human macula.

While it is expected that bright illumination of daylight and artificial lighting that may be used by a visually impaired individual will suffice for many visual activities that are performed with vision that has recovered as a result of the present treatments. It is also possible that light amplification devices may be used, as needed, to further enhance the affected person's visual sensitivity. The human vision system can operate over a 10 log unit range of luminance. On the other hand, microbial type rhodopsins, such as ChR2, operate over up to a 3 log unit range of luminance. In addition, the light conditions the patient encounters could fall outside of the operating range of the light sensor. To compensate for the various light conditions, a light pre-amplification or attenuation device could be used to expand the operation range of the light conditions. Such device would contain a camera, imaging processing system, and microdisplays, which can be assembled from currently available technologies, such as night vision goggles and/or 3D adventure and entertainment system. (See, for example the following URL on the Worldwide web-emagin.com/.)

The present invention may be used in combination with other forms of vision therapy known in the art. Chief among these is the use of visual prostheses, which include retinal implants, cortical implants, lateral geniculate nucleus implants, or optic nerve implants. Thus, in addition to genetic modification of surviving retinal neurons using the present methods, the subject being treated may be provided with a visual prosthesis before, at the same time as, or after the molecular method is employed.

The effectiveness of visual prosthetics can be improved with training of the individual, thus enhancing the potential impact of the ChR2 or HaloR transformation of patient cells as discussed herein. An example of an approach to training is found in US 2004/0236389 (Fink et al.), incorporated by reference. The training method may include providing a non-visual reference stimulus to a patient having a visual prosthesis based on a reference image. The non-visual reference stimulus is intended to provide the patient with an expectation of the visual image that the prosthesis will induce. Examples of non-visual reference stimuli are a pinboard, Braille text, or a verbal communication. The visual prosthesis stimulates the patient's nerve cells, including those cells whose responsiveness has been improved by expressing ChR2 and/or HaloR as disclosed herein, with a series of stimulus patterns attempting to induce a visual perception that matches the patient's expected perception derived from the non-visual reference stimulus. The patient provides feedback to indicate which of the series of stimulus patterns induces a perception that most closely resembles the expected perception. The patient feedback is used as a "fitness function" (also referred to as a cost function or an energy function). Subsequent stimuli provided to the patient through the visual prosthesis are based, at least in part, on the previous feedback of the patient as to which stimulus pattern(s) induce the perception that best matches the expected perception. The subsequent stimulus patterns may also be based, at least in part, on a fitness function optimization algorithm, such as a simulated annealing algorithm or a genetic algorithm.

Thus, in certain embodiments of this invention, the method of improving or restoring vision in a subject further comprises training of that subject, as discussed above. Preferred examples of training methods are:
(a) habituation training characterized by training the subject to recognize (i) varying levels of light and/or pattern stimulation, and/or (ii) environmental stimulation from a common light source or object as would be understood by one skilled in the art; and
(b) orientation and mobility training characterized by training the subject to detect visually local objects and move among said objects more effectively than without the training.

In fact, any visual stimulation techniques that are typically used in the field of low vision rehabilitation are applicable here.

The remodeling of inner retinal neurons triggered by photoreceptor degeneration has raised a concerns about retinal-based rescue strategies after the death of photoreceptors (Strettoi and Pignatelli 2000, *Proc Natl Acad Sci USA.* 97:11020-5; Jones, B W et al., 2003, *J Comp Neurol* 464:1-16; Jones, B W and Marc, R E, 2005, *Exp Eye Res.* 81:123-37; Jones, B W et al., 2005, *Clin Exp Optom.* 88:282-91). Retinal remodeling is believed to result from deafferentation, the loss of afferent inputs from photoreceptors—in other words, the loss of light induced activities. So after death of rods and cones, there is no light evoked input to retinal bipolar cells and ganglion cells, and through them to higher visual centers. In response to the loss of such input, the retina and higher visual network are triggered to undergo remodeling, in a way seeking other forms of inputs. Said otherwise, the retina needs to be used to sense light in order to maintain its normal network, and with the loss of light sensing, the network will deteriorate via a remodeling process. This process is not an immediate consequence of photoreceptor death; rather it is a slow process, providing a reasonably long window for intervention.

Thus, an additional utility of restoring light sensitivity to inner retinal neurons in accordance with the present invention is the prevention or delay in the remodeling processes in the retina, and, possibly, in the higher centers. Such retinal remodeling may have undesired consequences such as corruption of inner retinal network, primarily the connection between bipolar and RGCs. By introducing the light-evoked activities in bipolar cells or RGCs, the present methods would prevent or diminish the remodeling due to the lack of input; the present methods introduce this missing input (either starting from bipolar cells or ganglion cells), and thereby stabilize the retinal and higher visual center network. Thus, independently of its direct effects on vision, the present invention would benefit other therapeutic approaches such as photoreceptor transplantation or device implants.

Having now generally described the invention, the same will be more readily understood through reference to the following examples which are provided by way of illustration, and are not intended to be limiting of the present invention, unless specified.

Example I

Trans2ene Expression in Different Cellular Sites or Compartments

A. Materials and Methods

Viral vectors: Adeno-associated virus serotype 2 (rAAV2) cassette carrying a channelopsin-2 and GFP (Chop2-GFP) fusion construct (Bi, A. et al. Neuron 50:23-33 (2006); WO2007/131180) were modified by inserting subcellular sorting motifs at the 3' end of GFP (or, if no reporter is present, at the 3' end of ChR2 or HaloR. As described above, viral vectors carrying the transgene of ChR2-GFP—(motif) with a hybrid CMV early enhancer/chicken (β-actin) promoter (CAG) were packaged and affinity purified at the Gene Transfer Vector Core of the University of Iowa. Design of the vectors was is described above.

Animal and viral vector injection: 3-4 adult C57BL/6J mice aged 1-2 months per construct were used for the study. The mice were anesthetized by intraperitoneal injection of ketamine (120 mg/kg) and xylazine (15 mg/kg). Under a dissecting microscope, a small perforation was made with a needle in the sclera region posterior to the limbus, and 1.0 µl of viral vector suspension at a concentration of >1×10$^{12}$ gv/ml was injected into the intravitreal space of each eye. Four weeks after viral vector injection, animals were sacrificed by $CO_2$ asphyxiation followed by decapitation and enucleation. Histology: Enucleated eyes were fixed in 4% paraformaldehyde in phosphate buffer (PB) for 20 minutes and the dissected retina flat mounted onto a microscope slide for histological studies. The flat mounts were examined under a Zeiss Apotome microscope and Zstack images were taken at ~562 ms exposure time at optical sections of 1 µm apart in order to capture the axon, soma, and entire depth of the dendritic tree of each RGC.

Image analysis and fluorescence intensity ratio calculations: Intensity profiles of axon, soma, and dendrites for each RGC were measured in ImageJ (obtained from NIH) by applying lines of width of 5 pixels. For each RGC, axon intensity profile was obtained by averaging 3 measurements, somatic intensity profile was obtained by averaging 3 measurements, and dendritic intensity profile was obtained by averaging 9 measurements (3 proximal, 3 intermediate, and 3 distal). Dendrite/axon (D/A) and soma/axon (S/A) intensity ratios were then calculated from the average values for each RGC.

Statistical analysis of fluorescence intensity ratios: A one-way analysis of variance (ANOVA) was conducted with Bonferroni correction. $P<0.05$ is considered significantly different for somatic fluorescence intensity (Soma F. I.) measurements, dendrite to axon (D/A) ratios and soma to axon (S/A) ratios between groups.

B. Results

Results are shown in FIG. 1 and in Table 2 below.

TABLE 2

Comparison of Transduced CFP Expression in Different Cellular Sites or Compartments Mediated by Different Motifs:

| Sorting Motif | n[†] | Fluorescence Intensity at subcellular site Mean ± SE | | | Conclusion: targeted site (receptivce field) |
|---|---|---|---|---|---|
| | | Soma | Dendrite | Axon | |
| Control | 29 | 146.0 ± 8.3 | 65.2 ± 4.2 | 36.6 ± 1.9 | |
| Kv2.1 | 24 | 117.7 ± 6.0 | 2.31 ± 0.88[†] | 18.8 ± 1.4[†] | Soma, proximal dendritic (center) |
| Nav1.6 | 24 | 74.7 ± 8.2[†] | 10.6 ± 3.3 | 25.3 ± 1.6[†] | Axon initial segment, soma (center) |
| MLPH | 25 | 128.7 ± 9.3 | 73.5 ± 4.6 | 20.8 ± 1.9[†] | Somatodendritic (surroung-off center) |
| NLG-1 | 25 | 133.2 ± 7.2 | 76.2 ± 3.1 | 23.2 ± 1.9[†] | Somatodendritic (surroung-off center) |
| AMPAR | 23 | 143.2 ± 8.8 | 81.5 ± 3.8 | 47.9 ± 3.0[†] | No selective targeting in this experiment |
| Kv4.2 | 26 | 142.0 ± 8.9 | 76.6 ± 4.8 | 41.1 ± 2.9 | |
| nAChR | 29 | 120.0 ± 4.8 | 67.3 ± 3.3 | 31.8 ± 1.8 | |
| TLCN | 19 | 157.3 ± 15.9 | 53.4 ± 5.5 | 31.2 ± 3.4 | | n = number of cells analyzed
[†]Difference from control significant at $p<0.05$

Use of the Kv2.1 motif and targeted ChR2, and would similarly target HaloR, to soma and proximal dendritic regions (the center of receptive field) of RGCs. Use of Nav1.6 motif targets to soma and axon initial segments (the center of the receptive field). Kv2.1 appears to achieve such targeting more effectively than does Nav1.6.

Use of NLG-1 and MLPH sorting motifs targeted ChR2 (and would target HaloR) to distal dendritic regions (the surround of the receptive field) because, compared to control, they are more biased to distal dendritic regions. NLG appears to do this better.

Use of Kv2.1, Nav1.6, NLG-1 and MLPH reduces expression of the ChR2 or HaloR in the axons of retinal ganglion cells. Although not shown directly in FIG. 1 or Table 2, the ankyrin binding domain of Nav1.6 preferentially targeted Chop2-GFP to the axon initial segments as well as decreased expression in the dendrites of RGCs with D/A ratio 4.5 fold less than control. However the overall fluorescence intensity was lower for Nav1.6 compared to the control which contributed to the lack of significant difference in the S/A ratio compared to control. A previous (preliminary) study reported use of Anbthe ankyrin binding domain to target Chop2 to the somata of rabbit retinal ganglion cells via biolistic gene transfer (Greenberg, K. P. et al. *Invest. Ophthal.* Vis Sci 2009 (abstract) 2009).

Motifs from nAchR, KV4.2, TLCN, and AMPAR did not show statistically significant differences from the control group in somatic fluorescence, D/A ratio, and S/A ratio in this study. However, it is believed that with varying conditions, further modified vectors, etc., these too are useful as sorting motifs for targeting of, and spatially selective expression of transduced ChR2 or HaloR in RGC.

Example II

Physiological Responses of Cells Expressing ChR2

Studies were conducted (data not shown) in which the RGCs transduced by vectors comprising ChR2 and the Kv2.1 motif (center-targeting), which indeed showed enhanced expression in the center (Soma, proximal dendritic, were tested for electrical responses to light stimuli. A light slit was used to move a light along the cell, and recordings were made where the cell responded by depolarization. The responsiveness of such cells were enhanced compared to those of controls (transduced with vector not containing the sorting motif) indicating a close correlation between the histological evidence for site-specific expression of a transgene (GFP) and spatial organization of a transgene similarly introduced (ChR2). These results confirm the utility of this approach to evoking improved light responsiveness with organization reflective of normal retinal function (spatial specificity) in cells treated using the present methods.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A polynucleotide molecule comprising a nucleic acid sequence encoding a rhodopsin for expression in subcellular regions of a retinal neuron, comprising:
   (a) a first nucleotide sequence encoding a light-gated channel rhodopsin or a light-driven ion pump rhodopsin;
   (b) linked in frame to (a), a second nucleotide sequence encoding a peptide or polypeptide sorting motif, wherein the second nucleotide sequence is selected from the group consisting of:
      (1) a nucleotide sequence encoding nicotinic acetylcholine receptor α7 subunit (nAchR) comprising SEQ ID NO:9,
      (2) a nucleotide sequence encoding voltage-gated potassium channel 4.2 (Kv4.2) comprising SEQ ID NO:11,
      (3) a nucleotide sequence encoding telencephalin (TLCN) comprising SEQ ID NO:13, and
      (4) a nucleotide sequence encoding AMPA receptor GluR1 subunit comprising SEQ ID NO:15;
   (c) operatively linked to (a) and (b), a promoter sequence; and
   (d) a polyadenylation sequence.

2. The polynucleotide molecule of claim 1, wherein the promoter sequence is a cytomegalovirus enhancer/chicken β-actin promoter (CAG), and wherein the polyadenylation sequence is selected from:
   (i) a polyadenylation sequence from bovine growth hormone (bGHpoly A), and
   (ii) a SV40-derived polyadenylation sequence.

3. The polynucleotide molecule of claim 1, wherein (c) further comprises a transcriptional regulatory sequence, and wherein the transcriptional regulatory sequence is woodchuck hepatitis virus posttranscriptional regulatory element (WPRE).

4. The polynucleotide molecule of claim 1, further comprising, linked in frame with (a) and (b), a third nucleotide sequence encoding a reporter polypeptide.

5. The polynucleotide molecule of claim 1, wherein any one of the sorting motifs targets the rhodopsin to a surround or off-center region of a receptive field of the retinal neuron.

6. The polynucleotide molecule of claim 1, wherein any one of the sorting motifs targets the rhodopsin to a somatodendritic region of the retinal neuron.

7. A method of restoring light sensitivity to a retina, comprising:
(a) delivering to a retinal neuron the polynucleotide molecule of claim 1 comprising a nucleic acid sequence encoding a rhodopsin of claim 1, and
(b) expressing the polynucleotide molecule in the retinal neuron,
wherein expression of the polynucleotide molecule results in expression of a rhodopsin in selected subcellular regions of the retinal neuron, thereby restoring light sensitivity.

8. A method of selectively expressing a light-gated channel rhodopsin or a light-driven ion pump rhodopsin in a desired subcellular site or sites of a retinal ganglion cell (RGC), comprising:
(a) delivering to the RGC the polynucleotide molecule of claim 1; and
(b) expressing the polynucleotide molecule in the desired sites of the RGC.

9. A recombinant adeno-associated virus-2 (rAAV2) expression vector comprising a nucleic acid molecule encoding a rhodopsin for expression in subcellular regions of a retinal neuron comprising:
(a) a first nucleotide sequence encoding a light-gated channel rhodopsin or a light-driven ion pump rhodopsin;
(b) linked in frame to (a), a second nucleotide sequence encoding a peptide or polypeptide sorting motif, wherein the second nucleotide sequence is selected from the group consisting of:
(1) a nucleotide sequence encoding nicotinic acetylcholine receptor a7 subunit (nAchR) comprising SEQ ID NO: 9, (2) a nucleotide sequence encoding voltage-gated potassium channel 4.2 (Kv4.2) comprising SEQ ID NO: 11, (3) a nucleotide sequence encoding telencephalin (TLCN) comprising SEQ ID NO: 13, and (4) a nucleotide sequence encoding AMPA receptor GluR1 subunit comprising SEQ ID NO: 15:
(c) operatively linked to (a) and (b), a promoter sequence; and
(d) a polyadenylation sequence,
wherein the nucleic acid molecule is flanked at its 5' end by a 5' inverted terminal repeat (ITR) of AAV2 and at its 3' end by a 3' ITR of AAV2, wherein a nucleotide sequence of the 5'-ITR is set forth in SEQ ID NO: 17, and wherein a nucleotide sequence of the 3'-ITR is set forth in SEQ ID NO: 18.

10. The rAAV2 expression vector of claim 7, wherein the promoter sequence is a cytomegalovirus enhancer/chicken β-actin promoter (CAG), and wherein the polyadenylation sequence is selected from:
(i) a polyadenylation sequence from bovine growth hormone (bGHpoly A), and
(ii) a SV40-derived polyadenylation sequence.

11. The rAAV2 expression vector of claim 7, further comprising a transcriptional regulatory sequence, and wherein the transcriptional regulatory sequence is woodchuck hepatitis virus posttranscriptional regulatory element (WPRE).

12. The rAAV2 expression vector of claim 7, further comprising, linked in frame with (a) and (b), a third nucleotide sequence encoding a reporter polypeptide.

13. A method of restoring light sensitivity to a retina, comprising:
(a) delivering to a retinal neuron the rAAV2 expression vector of claim 9, and
(b) expressing the rAAV2 expression vector in the retinal neuron, wherein expression of the rAAV2 expression vector results in expression of a rhodopsin in selected subcellular regions of the retinal neuron, thereby restoring light sensitivity.

14. A method of selectively expressing a light-gated channel rhodopsin or a light-driven ion pump rhodopsin in a desired subcellular site or sites of a retinal ganglion cell (RGC), comprising:
(a) delivering to the RGC the rAAV2 expression vector of claim 7; and
(b) expressing the rAAV2 expression vector in the desired sites of said RGC.

15. A recombinant adeno-associated virus-2 (rAAV2) expression vector comprising a schematic structure selected from:
(a) 5'-ITR-CAG-ChR2-GFP-{Motif}-WPRE-bGHpoly A-ITR-3',
(b) 5'-ITR-CAG-ChR2-{Motif}-WPRE-bGHpoly A-ITR-3',
(c) 5'-ITR-CAG-HalOR-GFP-{Motif}-WPRE-bGH-polyA-ITR-3', and
(d) 5'-ITR-CAG-HaloR-{Motif}-WPRE-bGHpoly A-ITR-3';
wherein:
ITR is a AAV2 inverted terminal repeat,
CAG is a cytomegalovirus enhancer/chicken β-actin promoter,
ChR2 is a nucleotide sequence encoding channelrhodopsin-2,
GFP is a nucleotide sequence encoding a green fluorescent protein,
Motif is a nucleotide sequence encoding a sorting motif selected from the group consisting of:
(1) a nucleotide sequence encoding nicotinic acetylcholine receptor a7 subunit (nAchR) comprising SEQ ID NO:9,
(2) a nucleotide sequence encoding voltage-gated potassium channel 4.2 (Kv4.2) comprising SEQ ID NO:11,
(3) a nucleotide sequence encoding telencephalin (TLCN) comprising SEQ ID NO: 13, and
(4) a nucleotide sequence encoding AMPA receptor GluR1 subunit comprising SEQ ID NO: 15,
WPRE is a woodchuck hepatitis virus posttranscriptional regulatory element,
bGHpolyA is a polyA sequence from bovine growth hormone,
and
wherein any two or more of the ChR2, GFP, and Motif, or of the HaloR, GFP, and Motif, are linked in frame.

16. The rAAV2 expression vector of claim 15, wherein the rAAV2 expression vector comprises a nucleotide sequence set forth in SEQ ID NO:30 or 31.

17. A method of restoring light sensitivity to a retina, comprising:
 (a) delivering to a retinal neuron the rAAV2 expression vector of claim 15, and
 (b) expressing the rAAV2 expression vector in the retinal neuron,
 wherein the expression of the rAAV2 expression vector results in expression of a rhodopsin in selected subcellular regions of the retinal neuron, thereby restoring light sensitivity.

18. A method of selectively expressing a light-gated channel rhodopsin or a light-driven ion pump rhodopsin in a desired subcellular site or sites of a retinal ganglion cell (RGC), comprising:
 (a) delivering to the RGC the rAAV2 expression vector of claim 12; and
 (b) expressing the rAAV2 expression vector in the desired sites of said RGC.

\* \* \* \* \*